(12) United States Patent
Hughett, Sr. et al.

(10) Patent No.: US 9,282,973 B2
(45) Date of Patent: Mar. 15, 2016

(54) CLIP DEPLOYMENT TOOL AND ASSOCIATED METHODS

(75) Inventors: James David Hughett, Sr., Liberty Township, OH (US); Keith Edward Martin, Mason, OH (US); Kenneth Lance Miller, Hamilton, OH (US); Michael Dolgin, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 870 days.

(21) Appl. No.: 13/355,169

(22) Filed: Jan. 20, 2012

(65) Prior Publication Data

US 2013/0190777 A1   Jul. 25, 2013

(51) Int. Cl.
*A61B 17/128* (2006.01)
*A61B 17/122* (2006.01)
*A61B 17/00* (2006.01)
*A61B 17/29* (2006.01)

(52) U.S. Cl.
CPC ......... *A61B 17/1285* (2013.01); *A61B 17/1227* (2013.01); *A61B 2017/00867* (2013.01); *A61B 2017/2946* (2013.01)

(58) Field of Classification Search
CPC ........... A61B 17/1227; A61B 17/1285; A61B 2017/00867; A61B 17/128
USPC .......................................... 606/139, 142, 157
See application file for complete search history.

(56) References Cited

U.S. PATENT DOCUMENTS

| | | | |
|---|---|---|---|
| 2,060,724 A | 11/1936 | Carroll | |
| 2,371,978 A | 3/1945 | Perham | |
| 3,032,039 A | 5/1962 | Beaty | |
| 3,496,932 A | 2/1970 | Prisk et al. | |
| 3,682,180 A | 8/1972 | McFarlane | |
| 3,854,482 A | 12/1974 | Laugherty et al. | |
| 3,856,016 A | 12/1974 | Davis | |
| 3,856,017 A | 12/1974 | Perisse et al. | |

(Continued)

FOREIGN PATENT DOCUMENTS

| | | |
|---|---|---|
| EP | 1 600 108 A3 | 3/2006 |
| WO | WO 98/18389 | 5/1998 |

(Continued)

OTHER PUBLICATIONS

Lynch et al, Recanalization of the Left Atrial Appendage Demonstrated by Transesophageal Echocardiography, Ann Torac Surg, 1997; 63:1774-5, Published by Elsevier Science Inc., © 1997 The Society of Thoracic Surgeons, USA.

(Continued)

*Primary Examiner* — Jonathan W Miles
*Assistant Examiner* — Lucas Paez
(74) *Attorney, Agent, or Firm* — Porter Wright Morris & Arthur LLP; Ryan Willis

(57) ABSTRACT

A laparoscopic device comprising: (a) a housing operatively coupled to a first control and a second control; (b) an end effector operatively coupled to the first control, the end effector comprising a first component and a second component selectively repositionable with respect to one another within an X-Y plane, the end effector also including a third component selectively repositionable with respect to the second component within an Y-Z plane; (c) a laparoscopic conduit extending between the housing and the end effector; and, (d) an occlusion clip deployment device operatively coupled to the end effector and the second control.

18 Claims, 36 Drawing Sheets

(56) References Cited

U.S. PATENT DOCUMENTS

| | | |
|---|---|---|
| 3,856,018 A | 12/1974 | Perisse et al. |
| 3,954,108 A | 5/1976 | Davis |
| 4,226,239 A | 10/1980 | Polk et al. |
| 4,274,415 A | 6/1981 | Kanamoto et al. |
| 4,493,319 A | 1/1985 | Polk et al. |
| 4,552,128 A | 11/1985 | Haber |
| 4,788,966 A | 12/1988 | Yoon |
| 4,791,707 A | 12/1988 | Tucker |
| 4,869,268 A | 9/1989 | Yoon |
| 4,917,677 A | 4/1990 | McCarthy |
| 4,950,284 A | 8/1990 | Green et al. |
| 5,026,379 A | 6/1991 | Yoon |
| 5,100,416 A | 3/1992 | Oh et al. |
| 5,119,804 A | 6/1992 | Anstadt |
| 5,171,250 A | 12/1992 | Yoon |
| 5,217,030 A | 6/1993 | Yoon |
| 5,217,473 A | 6/1993 | Yoon |
| 5,258,000 A | 11/1993 | Gianturco |
| 5,282,829 A | 2/1994 | Hermes |
| 5,290,299 A | 3/1994 | Fain et al. |
| 5,306,234 A | 4/1994 | Johnson |
| 5,309,927 A | 5/1994 | Welch |
| 5,334,209 A | 8/1994 | Yoon |
| 5,336,252 A | 8/1994 | Cohen |
| 5,342,373 A | 8/1994 | Stefanchik et al. |
| 5,366,459 A | 11/1994 | Yoon |
| 5,425,740 A | 6/1995 | Hutchinson, Jr. |
| 5,439,156 A | 8/1995 | Grant et al. |
| 5,445,167 A | 8/1995 | Yoon et al. |
| 5,452,733 A | 9/1995 | Sterman et al. |
| 5,540,706 A * | 7/1996 | Aust et al. ................. 606/170 |
| 5,549,628 A | 8/1996 | Cooper et al. |
| 5,582,616 A | 12/1996 | Bolduc et al. |
| 5,609,599 A | 3/1997 | Levin |
| 5,620,452 A | 4/1997 | Yoon |
| 5,643,291 A * | 7/1997 | Pier et al. ................. 606/143 |
| 5,665,100 A | 9/1997 | Yoon |
| 5,667,518 A | 9/1997 | Pannell |
| 5,681,330 A | 10/1997 | Hughett et al. |
| 5,683,405 A | 11/1997 | Yacoubian et al. |
| 5,728,121 A | 3/1998 | Bimbo et al. |
| 5,758,420 A | 6/1998 | Schmidt et al. |
| 5,762,255 A | 6/1998 | Chrisman et al. |
| 5,782,397 A | 7/1998 | Koukline |
| 5,782,844 A | 7/1998 | Yoon et al. |
| 5,810,851 A | 9/1998 | Yoon |
| 5,810,882 A | 9/1998 | Bolduc et al. |
| 5,824,008 A | 10/1998 | Bolduc et al. |
| 5,830,221 A | 11/1998 | Stein et al. |
| 5,833,700 A | 11/1998 | Fogelberg et al. |
| 5,843,121 A | 12/1998 | Yoon |
| 5,865,791 A | 2/1999 | Whayne et al. |
| 5,893,863 A | 4/1999 | Yoon |
| 5,919,202 A | 7/1999 | Yoon |
| 5,921,997 A * | 7/1999 | Fogelberg et al. ............ 606/158 |
| 5,922,001 A | 7/1999 | Yoon |
| 5,922,002 A | 7/1999 | Yoon |
| 5,964,772 A | 10/1999 | Bolduc et al. |
| 5,984,917 A | 11/1999 | Fleischman et al. |
| 5,984,938 A | 11/1999 | Yoon |
| 5,984,939 A | 11/1999 | Yoon |
| 6,042,563 A | 3/2000 | Morejohn et al. |
| 6,074,418 A | 6/2000 | Buchanan et al. |
| 6,088,889 A | 7/2000 | Luther et al. |
| 6,096,052 A | 8/2000 | Callister et al. |
| 6,099,550 A | 8/2000 | Yoon |
| 6,152,144 A | 11/2000 | Lesh et al. |
| 6,165,183 A | 12/2000 | Kuehn et al. |
| 6,231,561 B1 | 5/2001 | Frazier et al. |
| 6,270,516 B1 | 8/2001 | Tanner et al. |
| 6,280,415 B1 | 8/2001 | Johnson |
| 6,290,674 B1 | 9/2001 | Roue et al. |
| 6,296,656 B1 | 10/2001 | Bolduc et al. |
| 6,299,612 B1 | 10/2001 | Ouchi |
| 6,312,447 B1 | 11/2001 | Grimes |
| 6,330,964 B1 | 12/2001 | Kayan et al. |
| 6,387,105 B1 | 5/2002 | Gifford, III et al. |
| 6,402,765 B1 | 6/2002 | Monassevitch et al. |
| 6,416,554 B1 | 7/2002 | Alferness et al. |
| 6,428,548 B1 | 8/2002 | Durgin et al. |
| 6,436,088 B2 | 8/2002 | Frazier et al. |
| 6,447,542 B1 | 9/2002 | Weadock |
| 6,450,391 B1 | 9/2002 | Kayan et al. |
| 6,485,407 B2 | 11/2002 | Alferness et al. |
| 6,488,689 B1 | 12/2002 | Kaplan et al. |
| 6,491,701 B2 | 12/2002 | Tierney et al. |
| 6,491,706 B1 | 12/2002 | Alferness et al. |
| 6,506,149 B2 | 1/2003 | Peng et al. |
| 6,508,829 B1 | 1/2003 | Levinson et al. |
| 6,514,265 B2 | 2/2003 | Ho et al. |
| 6,578,585 B1 | 6/2003 | Stachowski et al. |
| 6,579,304 B1 | 6/2003 | Hart et al. |
| 6,584,360 B2 | 6/2003 | Francischelli et al. |
| 6,607,504 B2 | 8/2003 | Haarala et al. |
| 6,607,542 B1 | 8/2003 | Wild |
| 6,610,074 B2 | 8/2003 | Santilli |
| 6,638,297 B1 * | 10/2003 | Huitema ................. 606/219 |
| 6,645,196 B1 | 11/2003 | Nixon et al. |
| 6,652,515 B1 | 11/2003 | Maguire et al. |
| 6,676,684 B1 | 1/2004 | Morley et al. |
| 6,746,461 B2 | 6/2004 | Fry |
| 6,770,081 B1 | 8/2004 | Cooper et al. |
| 6,793,664 B2 | 9/2004 | Mazzocchi et al. |
| 6,849,075 B2 | 2/2005 | Bertolero et al. |
| 6,849,078 B2 | 2/2005 | Durgin et al. |
| 6,896,684 B2 | 5/2005 | Monassevitch et al. |
| 6,911,032 B2 | 6/2005 | Jugenheimer et al. |
| 6,955,643 B2 | 10/2005 | Gellman et al. |
| 6,981,628 B2 * | 1/2006 | Wales ................. 227/178.1 |
| 7,008,401 B2 | 3/2006 | Thompson et al. |
| 7,113,831 B2 | 9/2006 | Hooven |
| 7,118,582 B1 | 10/2006 | Wang et al. |
| 7,169,164 B2 | 1/2007 | Borillo et al. |
| 7,226,458 B2 | 6/2007 | Kaplan et al. |
| 7,318,829 B2 | 1/2008 | Kaplan et al. |
| 7,344,543 B2 | 3/2008 | Sra |
| 7,424,965 B2 * | 9/2008 | Racenet et al. ............ 227/180.1 |
| 7,644,848 B2 | 1/2010 | Swayze et al. |
| 7,645,285 B2 * | 1/2010 | Cosgrove et al. ............. 606/151 |
| 7,896,895 B2 * | 3/2011 | Boudreaux et al. ............ 606/157 |
| 8,172,870 B2 * | 5/2012 | Shipp ................. 606/205 |
| 8,795,325 B2 * | 8/2014 | Taylor et al. ................. 606/205 |
| 2001/0005787 A1 | 6/2001 | Oz et al. |
| 2001/0039434 A1 | 11/2001 | Frazier et al. |
| 2001/0039435 A1 | 11/2001 | Roue et al. |
| 2002/0013605 A1 | 1/2002 | Bolduc et al. |
| 2002/0022860 A1 | 2/2002 | Borillo et al. |
| 2002/0026214 A1 | 2/2002 | Tanner |
| 2002/0026216 A1 | 2/2002 | Grimes |
| 2002/0032454 A1 | 3/2002 | Durgin et al. |
| 2002/0035374 A1 | 3/2002 | Borillo et al. |
| 2002/0049457 A1 | 4/2002 | Kaplan et al. |
| 2002/0055750 A1 | 5/2002 | Durgin et al. |
| 2002/0058967 A1 | 5/2002 | Jervis |
| 2002/0062130 A1 | 5/2002 | Jugenheimer et al. |
| 2002/0065524 A1 | 5/2002 | Miller et al. |
| 2002/0077660 A1 | 6/2002 | Kayan et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111641 A1 | 8/2002 | Peterson et al. |
| 2002/0111647 A1 | 8/2002 | Khairkhahan et al. |
| 2002/0169377 A1 | 11/2002 | Khairkhahan et al. |
| 2002/0177859 A1 | 11/2002 | Monassevitch et al. |
| 2002/0177862 A1 | 11/2002 | Aranyi et al. |
| 2003/0009441 A1 | 1/2003 | Holsten et al. |
| 2003/0018362 A1 | 1/2003 | Fellows et al. |
| 2003/0023248 A1 | 1/2003 | Parodi |
| 2003/0023266 A1 | 1/2003 | Borillo et al. |
| 2003/0055422 A1 | 3/2003 | Lesh |
| 2003/0158464 A1 | 8/2003 | Bertolero |
| 2004/0030335 A1 | 2/2004 | Zenati et al. |
| 2004/0064138 A1 | 4/2004 | Grabek |
| 2004/0073241 A1 | 4/2004 | Barry et al. |

(56) References Cited

U.S. PATENT DOCUMENTS

| | | |
|---|---|---|
| 2004/0097982 A1 | 5/2004 | Jugenheimer et al. |
| 2004/0215216 A1 | 10/2004 | Gannoe et al. |
| 2005/0085808 A1 | 4/2005 | Nakao |
| 2005/0149068 A1 | 7/2005 | Williams et al. |
| 2005/0149069 A1 | 7/2005 | Bertolero et al. |
| 2005/0203561 A1 | 9/2005 | Palmer et al. |
| 2006/0020271 A1 | 1/2006 | Stewart et al. |
| 2006/0084974 A1 | 4/2006 | Privitera et al. |
| 2006/0161147 A1 | 7/2006 | Privitera et al. |
| 2006/0161149 A1 | 7/2006 | Privitera et al. |
| 2007/0108252 A1* | 5/2007 | Racenet et al. ............ 227/176.1 |
| 2007/0149988 A1 | 6/2007 | Michler et al. |
| 2008/0033457 A1 | 2/2008 | Francischelli et al. |
| 2008/0125795 A1 | 5/2008 | Kaplan et al. |
| 2009/0012545 A1 | 1/2009 | Williamson, IV et al. |
| 2009/0069823 A1 | 3/2009 | Foerster et al. |
| 2009/0253961 A1 | 10/2009 | Le et al. |
| 2010/0004663 A1 | 1/2010 | Murphy et al. |
| 2010/0204716 A1 | 8/2010 | Stewart et al. |
| 2011/0152922 A1 | 6/2011 | Jeong |
| 2012/0035622 A1 | 2/2012 | Kiser et al. |

FOREIGN PATENT DOCUMENTS

| | | |
|---|---|---|
| WO | WO 99/62409 A1 | 12/1999 |
| WO | WO 01/35832 A2 | 5/2001 |
| WO | WO 01/97696 A1 | 12/2001 |
| WO | WO 03/011150 A1 | 2/2003 |
| WO | WO 03/096881 A2 | 11/2003 |
| WO | WO 2007/009099 A2 | 1/2007 |
| WO | PCT/US2006/027553 | 1/2008 |
| WO | PCT/US2012/051002 | 8/2012 |
| WO | PCT/US2012/051002 | 10/2012 |
| WO | PCT/US13/22600 | 4/2013 |

OTHER PUBLICATIONS

Hoit et al, Altered Left Atrial Compliance After Atrial Appendectomy, AHA Circulation Research, vol. 72, No. 1, Jan. 1993, pp. 167-175, From University of Cincinnati Medical Center, Department of Internal Medicine, Cincinnati, Ohio, USA.

Landymore, et al, Staple Closure of the Left Atrial Appendage, The Canadian Journal of Surgery, vol. 27, No. 2, Mar. 1984, pp. 144-145, From Victoria General Hospital, Dept. of Surgery,Div. of Cardiovascular Surgery, Halifax, NS.

Robin et al, Strangulation of the Left Atrial Appendage through a Congenital Partial Pericardial Defect, CHEST, 67:3, Mar. 1975, pp. 354-355, From Dept. of Cariology, Hutzel Hospital Medical Unit, Wayne State University, Detroit, MI, USA.

Tabata, et al, Role of Left Atrial Appendage in Left Atrial Reservoir Function as Evaluated by Left Atrial Appendage Clamping During Cardiac Surgery, American Journal of Cardiology, vol. 81, Feb. 1, 1998, pp. 327-332, © 1998 Excerpta Medica, Inc., USA.

Aytac, et al, Intrapericardial aneurysm of the left atrial appendix, J. Cardiovas. Surg., 21, 1980, pp. 509-511, USA.

Lindsay, M.D., Bruce D., Obliteration of the Left Atrial Appendage: A Concept Worth Testing, AnnThorac Surg 1996;61:515, © 1996 The of Society Thoracic Surgeons, Published by Elsevier Science, Inc. ,USA.

Landymore, M.D., R. W., Stapling of Left Atrial Appendage, To the Editor: , Ann Thorac Surg 1989;47:794, © 1989 The Society of Thoracic Surgeons, USA.

Disesa, et al, Ligation of the Left Atrial Appendage Using an Automatic Surgical Stapler, Accepted for publication Jul. 26, 1988, Div. of Cardiac Surgery, Brigham and Women's Hospital, Boston, MA.

Wakabayashi, MD., Akio, Expanded applications of diagnostic and therapeutic thoracoscopy, J. Thorac Cardiovasc Surg 1991;102:721-3, from Dept. of Surgery, University of Californaia, Irvine, Irvine, CA.

Thomas, TV, Left atrial appendage and valve replacement, Am Heart Journal, vol. 84, No. 6, Dec. 1972, pp. 838-839, USA.

Coselli, et al, Congenital Intrapericardial Aneurysmal Dilatation of the Left Atrial Appendage, Case Reports: The Annals of Thoracic Surgery, vol. 39, No. 5, May 1985, pp. 466-468, From Dept. of Surgery, Baylor College of Medicine, Houston TX.

Coffin, M.D., Laurence H., Use of the Surgical Stapler to Obliterate the Left Atrial Appendage, Surgery, Gynecology & Obsterics, Jun. 1985, vol. 160, pp. 565-566, From Div., of Thoracic and Cardiac Surgery, Univ of Vermont College of Medicine, Burlington, VT.

Katz, et al, Surgical Left Atrial Appendage Ligation is Frequently Incomplete: A Transesophageal Echocardiographic Study, J Am College of Cardiology, vol. 36, No. 2, pp. 468-471, Aug. 2000, © 2000 American College of Cardiology, Published by Elsevier Science, Inc., USA.

Ganeshakrishnan, et al, Congenital Intrapericardial Aneurysm of the Left-Atrial Appendage, Case Report: Thorac. cardiovasc. Surgeon 40 (1992), 382-384, © Georg Thieme Verlag Stuttgart, New York, USA.

Unknown, surgical procedure report to track prior art with regards to a minimimally invasive left atrial appendage exclusion, Jan. 1, 2007, USA.

Stollberger, et. al, Elimination of the Left Atrial Appendage to Prevent Stroke or Embolism?, Opinions/Hypotheses, CHEST/ 124 / 6/ Dec. 2003, pp. 2356-2362, © American College of Chest Physicians, USA.

Cox, et al, Five-Year Experience with the Maze Procedure for Atrial Fibrillation, Ann Thorac Surg 1993; 56:814-24, Presented at the Twenty-ninth Annual Meeting of The Society of Thoracic Surgeons, San Antonio, TX, Jan. 25-27, 1993, © 1993 The Society of Thoracic Surgeons, USA.

Stollberger, et al, Is left atrial appendage occlusion useful for prevention of stroke or embolism in atrial fibrillation?, Z Kardiol 91:376-379 (2002), © Steinkopff Verlag 2002, Germany.

Riley, et al, Mitral Valve Repair, CTSNET Experts' Techniques, doc 5729, pp. 1-7, © 2004 Cardiothoracic Surgery Network, USA.

Johnson, et al, The left atrial appendage: our most lethal human attachment! Surgical implications, EU J Cardio-thor Surg 17 (2000) 718-722, Presented at the 13th Annual Meeting of the European Association for Cardio-thor Surg 17 (2000) 718-722, Presented at the 13th Annual Meeting of The European Association for Cardio-thoracic Surgery, Glasgow, Scotland, UK, Sep. 5-8, 1999, © 2000 Elsevier Science B.V.

Blackshear, et al, Thoracoscopic Extracardiac Obliteration of the Left Atrial Appendage for Stroke Risk Reduction in Atrial Fibrillation, JACC, vol. 42, No. 7, 2003, Oct. 1, 2003:1249-52, © 2003 American College of Cardiology Foundation, Published by Elsevier Inc., USA.

Odell, et al, Thoracoscopic Obliteration of the Left Atrial Appendage: Potential for Stroke Reduction?, Ann Thorac Surg 1996;61:565-9, © 1996 The Society of Thoracic Surgeons, Published by Elsevier Science Inc., USA.

Blackshear, et al, Appendage Obliteration to Reduce Stroke in Cardiac Surgical Patients with Atrial Fibrillation, Ann Thorac Surg 1996;61:755-9, © 1996 The Society of Thoracic Surgeons, Published by Elsevier Science Inc., USA.

Gillinov, et al, Stapled excision of the left atrial appendage, J Thorac Cardiovasc Surg 2005;129:679-80, © 2005 The American Association for Thoracic Surgery, USA.

Stollberger, et al, Stroke Prevention by Means of Left Atrial Appendage Strangulation?, To the Editor:, J Thorac Cardiovasc Surg 2010, p. 732, USA.

Kamohara et al, Evaluation of a novel device for left atrial appendage exclusion: The second-generation atrial exclusion device, J Thorac Cardiov Surg 2006;132:340-46, © 2006 American Association for Thoracic Surgery, USA.

Kamohara et al, A novel device for left atrial appendage exclusion, J Thorac Cardiov Surg 2005;130:1639-44, © 2005 American Association for Thoracic Surgery, USA.

Stollberger et al, Leave the left atrial appendage untouched for stroke prevention!, To the Editor:, J Thorac Cardiov Surg, vol. 134, No. 2, Aug. 2007, pp. 549-550, © 2007 American Association for Thoracic Surgery, USA.

Wudel et al, Video-Assisted Epicardial Ablation and Left Atrial Appendage Exclusion for Atrial Fibrillation: Extended Follow-up,

(56) References Cited

OTHER PUBLICATIONS

Ann Thorac Surg, Aug. 14, 2007, pp. 1-5, © 2007 The Society of Thoracic Surgeons, Published by Elsevier Inc., USA.

Salzberg, et al, Surgical left atrial appendage occulsion: evaluation of a novel device with magnetic resonance imaging, EU J Cardio-thor Surg 34 (2008) 766-770, © 2008 European Association for Cardio-Thoracic Surgery, Published by Elsevier B.V.

Salzberg, et al, Left atrial appendage clip occlusion: Early clinical results, J Thorac Cardiov Surg, vol. 139, No. 5, pp. 1269-1274, © 2010 The American Association for Thoracic Surgery, USA.

Unknown, Endowrist Instruments and Accessories Catalog, Intuitive Surgical, Sunnyvale, California, Sep. 2005.

Kamohara et al, Impact of left atrial appendage exclusion on left atrial function, J Thorac Cardiov Surg 2007;133:174-81, © 2007 American Association for Thoracic Surgery, USA.

Fumoto et al, A novel device for left atrial appendage exclusion: The third-generation atrial exclusion device, J Thorac Cardiov Surg 2008;136:1019-27, © 2008 American Association for Thoracic Surgery, USA.

Lipkin et al, Aneurysmal dilation of left atrial appendage diagnosed by cross sectional echocardiography and surgically removed, Br Heart J 1985; 53:69-71, National Heart Hospital, London, UK.

Cohn et al, Right thoracotomy, femorofemoral bypass, and deep hypothermia for re-replacement of the mitral valve, Ann Thorac Surg 1989;48:69-71, © 1989 Society of Thoracic Surgeons, USA.

Al-Saady et al, Left atrial appendage: structure, function, and role in thrombo-boembolism, Heart 1999;82:547-555, St. George's Hosp Med School, London UK.

Kaymaz et al, Location, Size and Morphological Characteristics of Left Atrial Thrombi as Assessed by Echocardiography in Patients with Rheumatic Mitral Valve Disease, Eur. J Echocardiography, vol. 2, Issue 4, Dec. 2001, pp. 270-276, © 2001 The European Society of Cardiology.

Rosenzweig et al, Thromboembolus from a Ligated Left Atrial Appendage, J Am Soc Echocardiography, vol. 14, pp. 396-398, May 2001, © 2001 American Society of Echocardiography, USA.

Hondo et al, The Role of the Left Atrial Appendage; A Volume Loading Study in Open-chest Dogs, Jpn Heart J, Mar. 1995, pp. 225-234, Japan.

Veinot et al, Anatomy of the Normal Left Atrial Appendage: A Quantitative Study of Age-Related Changes . . . , ahajournals 1997; 96: 3112-3115, USA.

Halperin et al, Obliteration of the Left Atrial Appendage for Prevention of Thromboembolis, J Am Coll of Cardiol, 2003;42:1259-1261, USA.

Unknown, Transesophageal Echocardiographic Correlates of Thromboembolism in High Risk Patients with Nonvalvular Atrial Fibrillation, The American College of Physicians, Apr. 1998, pp. 639-647, © 1998 American College of Physicians, USA.

Omari et al, Effect of right atrial appendectomy on the release of atrial natriuretic hormone, J Thorac Cardiovasc Surg 1991; 102:272-279, USA.

Mole et al, Desmoid Tumour in Thoractomy Scar 5 Years After Excision of a Left Giant Atrial Appendage Aneurysm in Female with a Family History of Gardner's Syndrome, Thorac Cardiovasc Surg 40 (1991) pp. 300-302, © 1992 Georg Thieme Verlag Stuttgart, New York.

Crystal et al, Left Atrial Appendage Occlusion Study (LAAOS): A randomized clinical trial of left atrial appendage occlusion during routine coronary artery bypass graft surgery for long-term stroke prevention, Am Heart J 2003; 145:174-178, © 2003 Mosby, Inc., USA.

Garcia-Fernadez et al, Role of left atrial appendage obliteration in stroke reduction in patients with mitral valve prosthesis: A transeophageal echocardiographic study, J Am Coll Cardiol 2003;42:1253-1258, © 2003 American College of Cardioldgy Foundation, USA.

Burke et al, Improved Surgical Approach to Left Atrial Appendage Aneurysm, J Cardi Surg, 1992, vol. 7, No. 2, pp. 104-107, USA.

Fisher et al, Large Gradient Across a Partially Ligated Left Atrial Appendage, J Am Soc Echocardiography, vol. 11, No. 12, pp. 1163-1165, © 1998 American Society of Echocardiography, USA.

Grundeman et al, Experimental videothoracoscopic cannulation of the left atrial appendix, Surg Endosc (1993) 7:511-513, © 1993 Springer-Verlag New York, Inc., USA.

* cited by examiner

CLIP DEPLOYMENT TOOL AND ASSOCIATED METHODS

FIELD OF THE INVENTION

The present disclosure relates to deployment of an occlusion clip and, more specifically, to devices and methods utilized to deploy an occlusion clip using a handheld device.

INTRODUCTION TO THE INVENTION

The exemplary embodiments disclosed herein include one or more active or passive repositioning mechanisms. As will be discussed in more detail hereafter, an active repositioning mechanism provides for infinite adjustments as the user is physically operating a control to directly manipulate the repositioning of an end effector or a device mounted to an end effector. In contrast, a passive repositioning mechanism can be thought of as acting similar to a light switch, either off or on. In this manner, the passive repositioning mechanism either allows or disallows repositioning of the end effector or a device mounted to the end effector, but is not responsible for actively manipulating the aspect ultimately repositioned. Put another way, the passive repositioning system allows for free movement of the end effector or a device mounted to the end effector within the relevant range of motion when the mechanism is in the "on" position, but locks movement when the mechanism is in the "off" position. In exemplary form, a laparoscopic device may incorporate passive repositioning mechanisms to control movements in different directions, such as pitch and yaw.

It is a first aspect of the present invention to provide a laparoscopic device comprising: (a) a housing operatively coupled to a first control and a second control; (b) an end effector operatively coupled to the first control, the end effector comprising a first component and a second component selectively repositionable with respect to one another within an X-Y plane, the end effector also including a third component selectively repositionable with respect to the second component within an Y-Z plane; (c) a laparoscopic conduit extending between the housing and the end effector; and, (d) an occlusion clip deployment device operatively coupled to the end effector and the second control.

In a more detailed embodiment of the first aspect, the handle housing is operatively coupled to a third control, the third control is operatively coupled to the occlusion clip and the occlusion clip deployment device, and the third control controls disengagement of the occlusion clip from the occlusion clip deployment device. In yet another more detailed embodiment, the first control includes a first passive constraint and a second passive constraint, the first passive constraint in an unlocked position allows free motion between the first component and the second component within the X-Y plane, the first passive constraint in a locked position retards free motion between the first component and the second component within the X-Y plane, the second passive constraint in an unlocked position allows free motion between the second component and the third component within the Y-Z plane, and the second passive constraint in a locked position retards free motion between the second component and the third component within the Y-Z plane. In a further detailed embodiment, the first passive constraint includes at least one connection wire in tension that is operatively coupled to the second component and to the housing, and the second passive constraint includes at least one connection wire in tension that is operatively coupled to the third component and to the housing. In still a further detailed embodiment, the first control includes a repositionable button selectively coupled to a first reel and a second reel, where the button is repositionable between a locked and an unlocked position, where the locked position retards rotation of the first reel and the second reel, and where the unlocked position allows rotation of the first reel and the second reel, the first reel is operatively coupled to a first connection line operatively coupled to the first component, the second reel is operatively coupled to a second connection line operatively coupled to the second component, and wherein the first reel is independently repositionable with respect to the second reel.

In yet another more detailed embodiment of the first aspect, the second control includes a lever operatively coupled and selectively repositionable with respect to the housing, the lever being operatively coupled to a first connection line operatively coupled to the occlusion clip deployment device so that movement of the lever is operative to reposition at least a portion of the occlusion clip deployment device, the lever is repositionable between a locked and an unlocked position, the unlocked position allows the lever to be repositioned, and the locked position retards the lever from being repositioned. In still another more detailed embodiment, the laparoscopic device further includes a third control operatively coupled to the housing, wherein the third control is operatively coupled to a first connection line operatively coupled to the occlusion clip deployment device so that movement of the third control is operative to reposition at least a portion first connection line with respect to the occlusion clip deployment device. In a further detailed embodiment, the third control includes a plug detachable from the housing, the plug is repositionable from an attached position coupled to the housing to a detached position decoupled from the housing, and repositioning the plug from the attached position to the detached position causes more of the first connection line to be drawn into the housing and further away from the occlusion clip deployment device. In still a further detailed embodiment, the laparoscopic device further includes an occlusion clip operatively coupled to the clip deployment device using the first connection line. In a more detailed embodiment, the end effector includes a robotic grasping feature to facilitate grasping and repositioning of the end effector by a robotic grasper.

It is a second aspect of the present invention to provide a laparoscopic device comprising: (a) a housing operatively coupled to a first control; (b) an end effector operatively coupled to the first control, the end effector comprising a clevis selectively repositionable with respect to a dual pivot joint within an X-Y plane, the dual pivot joint selectively repositionable with respect to a yoke within an Y-Z plane; (c) a laparoscopic conduit extending between the housing and the end effector.

In a more detailed embodiment of the second aspect, the first control includes a first line and a second line extending along the laparoscopic conduit concurrently coupled to the dual pivot joint, the first line impacting movement of the dual pivot joint with respect to the clevis in a first direction within the X-Y plane, the second line impacting movement of the dual pivot joint with respect to the clevis in a second direction, generally opposite the first direction, within the X-Y plane, and the first control includes a third line and a fourth line extending along the laparoscopic conduit concurrently coupled to the yoke, the third line impacting movement of the yoke with respect to the dual pivot joint in a third direction within the Y-Z plane, the fourth line impacting movement of the yoke with respect to the dual pivot joint in a fourth direction, generally opposite the third direction, within the Y-Z plane. In yet another more detailed embodiment, the first line and the second line are coupled to a first actuator mounted to the housing, the first actuator is repositionable and operative to reposition the first line and the second line in order to create movement between the clevis and dual pivot joint, the third line and the fourth line are coupled to a second actuator mounted to the housing, the second actuator is repositionable and operative to reposition the third line and the fourth line in order to create movement between the yoke and dual pivot joint. In a further detailed embodiment, the first actuator comprises a first reel upon which at least a portion of the first line and the second line are wound, the second actuator comprises a second reel upon which at least a portion of the third line and the fourth line are wound, repositioning of the first reel is operative to distally reposition one of the first line and the second line, while repositioning of the first reel is operative to proximally reposition the other of the first line and the second line, repositioning of the second reel is operative to distally reposition one of the third line and the fourth line, while repositioning of the second reel is operative to proximally reposition the other of the third line and the fourth line.

In yet another more detailed embodiment of the second aspect, the first control includes a brake that may be selectively applied to the first actuator and the second actuator to retard movement of the dual pivot joint with respect to the clevis within the X-Y plane and movement of the yoke with respect to the dual pivot joint within the Y-Z plane. In still another more detailed embodiment, the brake comprises a spring biased button operatively coupled to a series of teeth, the first reel includes a series of teeth, the second reel includes a series of teeth, and engagement between at least one of the series of teeth operatively coupled to the spring biased button and at least one of the series of teeth of the first reel and least one of the series of teeth of the second reel is operative to retard movement of the dual pivot joint with respect to the clevis within the X-Y plane and movement of the yoke with respect to the dual pivot joint within the Y-Z plane. In a further detailed embodiment, the laparoscopic device further includes an occlusion clip deployment device operatively coupled to the end effector and to a second control, where the housing is operatively coupled to the second control, and the second control includes a clip repositioning line extending along the laparoscopic conduit, the clip repositioning line impacting movement of the occlusion clip deployment device between a first position and a second position. In still a further detailed embodiment, the second control includes a lever operatively coupled and selectively repositionable with respect to the housing, the lever being operatively coupled to the clip repositioning line so that movement of the lever is operative to reposition the occlusion clip deployment device, the lever is repositionable between a locked and an unlocked position, the unlocked position allows the lever to be repositioned, and the locked position retards the lever from being repositioned. In a more detailed embodiment, the laparoscopic device further includes a deployment control operatively coupled to the housing, the deployment control including a deployment line extending along the laparoscopic conduit and concurrently mounted to a deployment plug removably fastened to the housing. In a more detailed embodiment, the laparoscopic device further includes an occlusion clip operatively coupled to the occlusion clip deployment device using the deployment line. In another more detailed embodiment, the occlusion clip includes a first jaw opposing a second jaw, a first retainer loop at least partially circumscribes the first jaw, at least a portion of the occlusion clip deployment device, and at least a portion of the deployment line, a second retainer loop at least partially circumscribes the second jaw, at least a portion of the occlusion clip deployment device, and at least a portion of the deployment line. In yet another more detailed embodiment, the end effector includes a robotic grasping feature to facilitate grasping and repositioning of the end effector by a robotic grasper.

It is a third aspect of the present invention to provide a laparoscopic device comprising: (a) a laparoscopic handle; (b) a laparoscopic conduit operatively coupled to the laparoscopic handle; (c) a laparoscopic end effector operatively coupled to the laparoscopic conduit; (d) a passive control allowing repositioning of an end effector with respect to the laparoscopic conduit within an X-Y plane and a Y-Z plane when the passive control is disengaged and retarding repositioning of the end effector with respect to the laparoscopic conduit within the X-Y plane and the Y-Z plane when the passive control is engaged.

DETAILED DESCRIPTION

The exemplary embodiments of the present disclosure are described and illustrated below to encompass surgical equipment and, more specifically, to surgical equipment that may be used in minimally invasive procedures. The disclosure also relates to surgical equipment to facilitate the positioning and deployment of an atrial appendage occlusion device. In addition, the disclosure relates to surgical equipment that is adapted to accommodate or work in tandem with flexible endoscopes. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Figure 1:
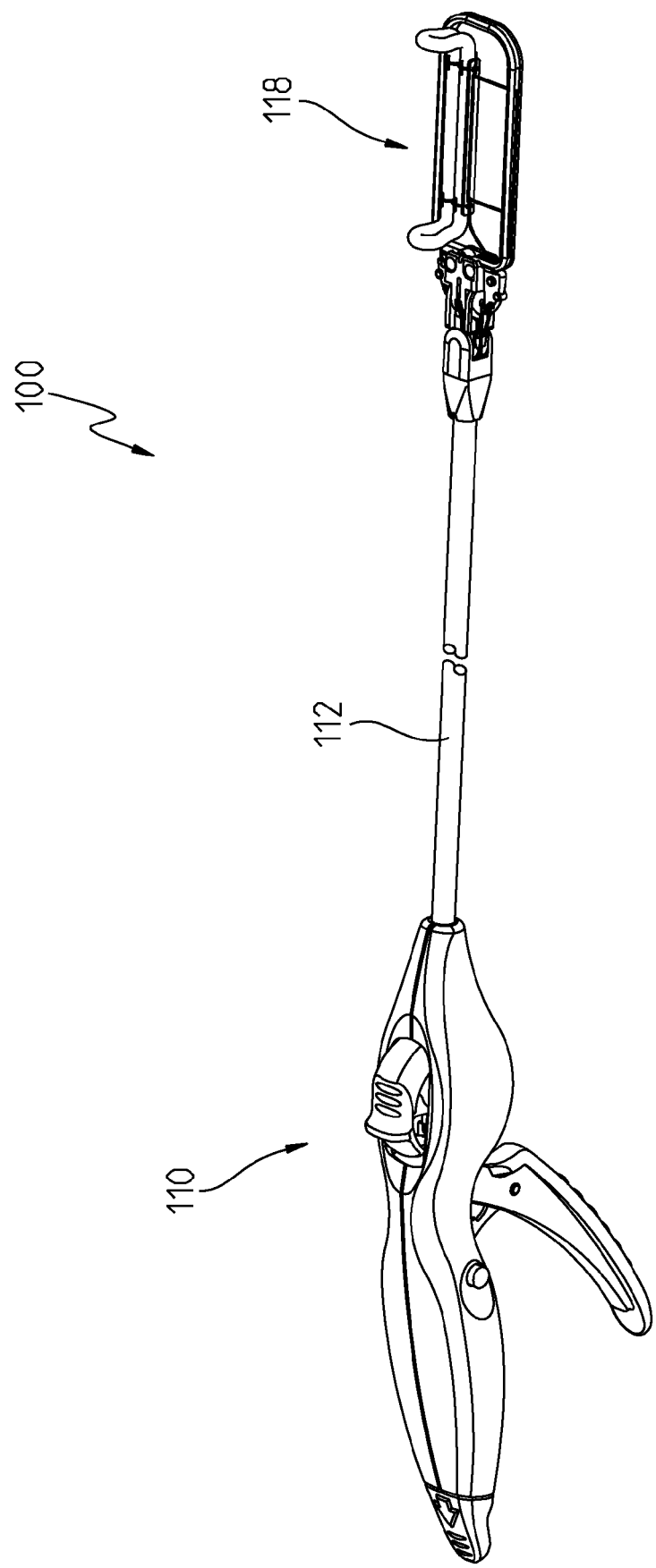
FIG. 1 is an elevated perspective view of an exemplary laparoscopic device in accordance with the instant disclosure.
Figure 2:
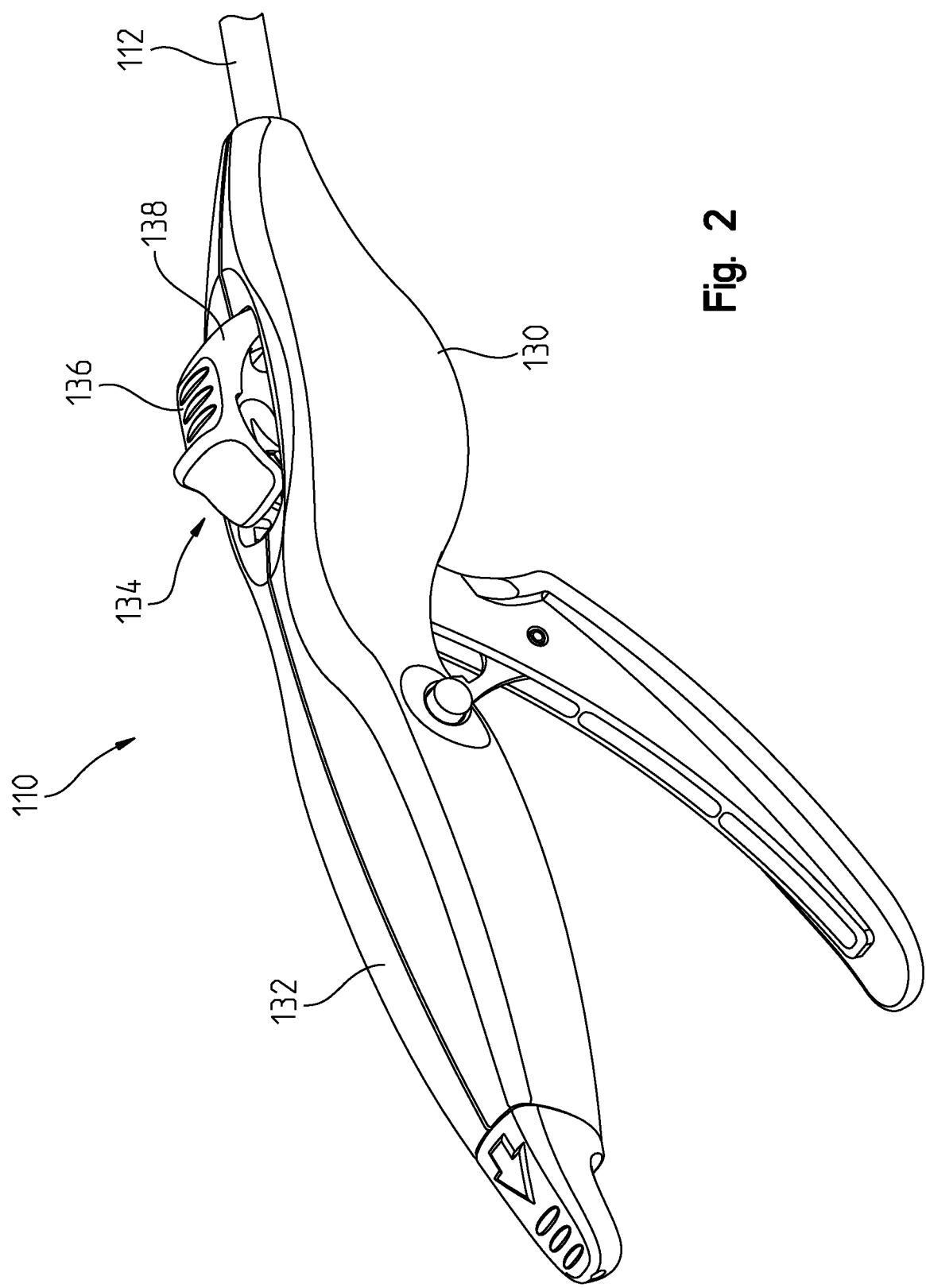
FIG. 2 is an elevated perspective view of the proximal end of the exemplary laparoscopic device of FIG. 1.
Figure 3:
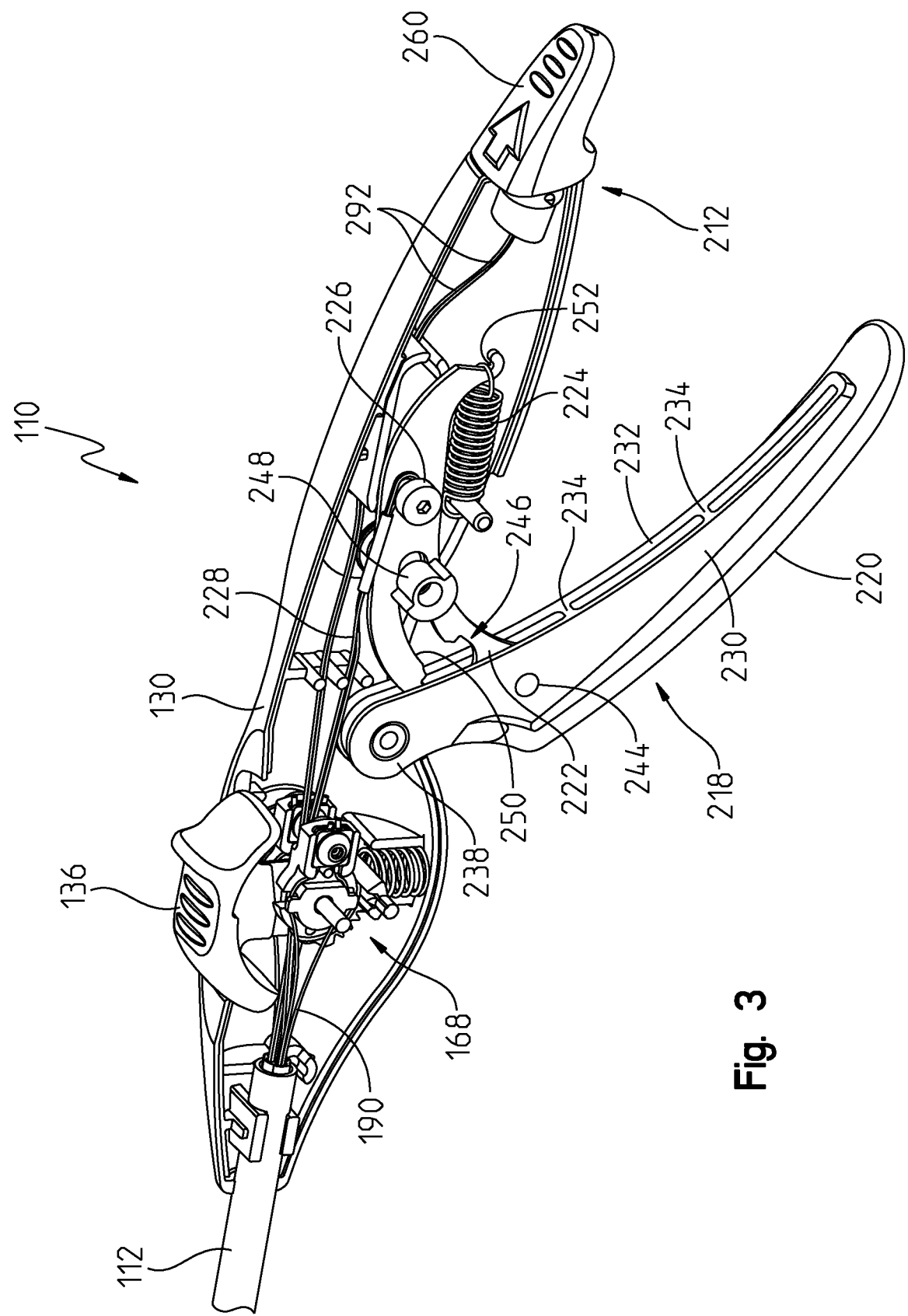
FIG. 3 is an elevated perspective view of the proximal end of the exemplary laparoscopic device of FIG. 2, without the left side housing.
Figure 4:
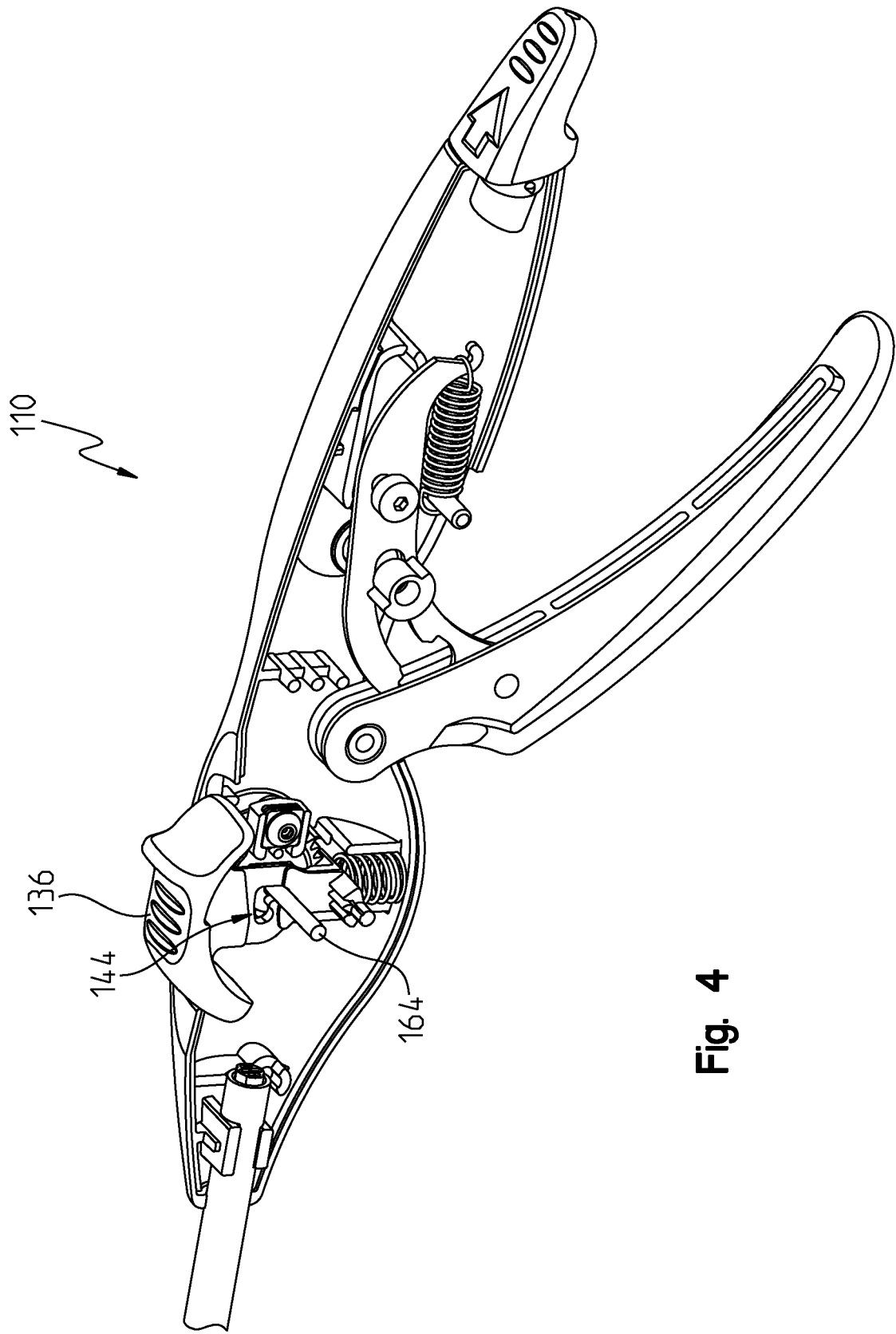
FIG. 4 is a profile view of the proximal end of the exemplary laparoscopic device of FIG. 2, without the left side housing and without some of the internal components in order to show the axle in a distal portion of a through hole in the repositionable button.
Figure 5:
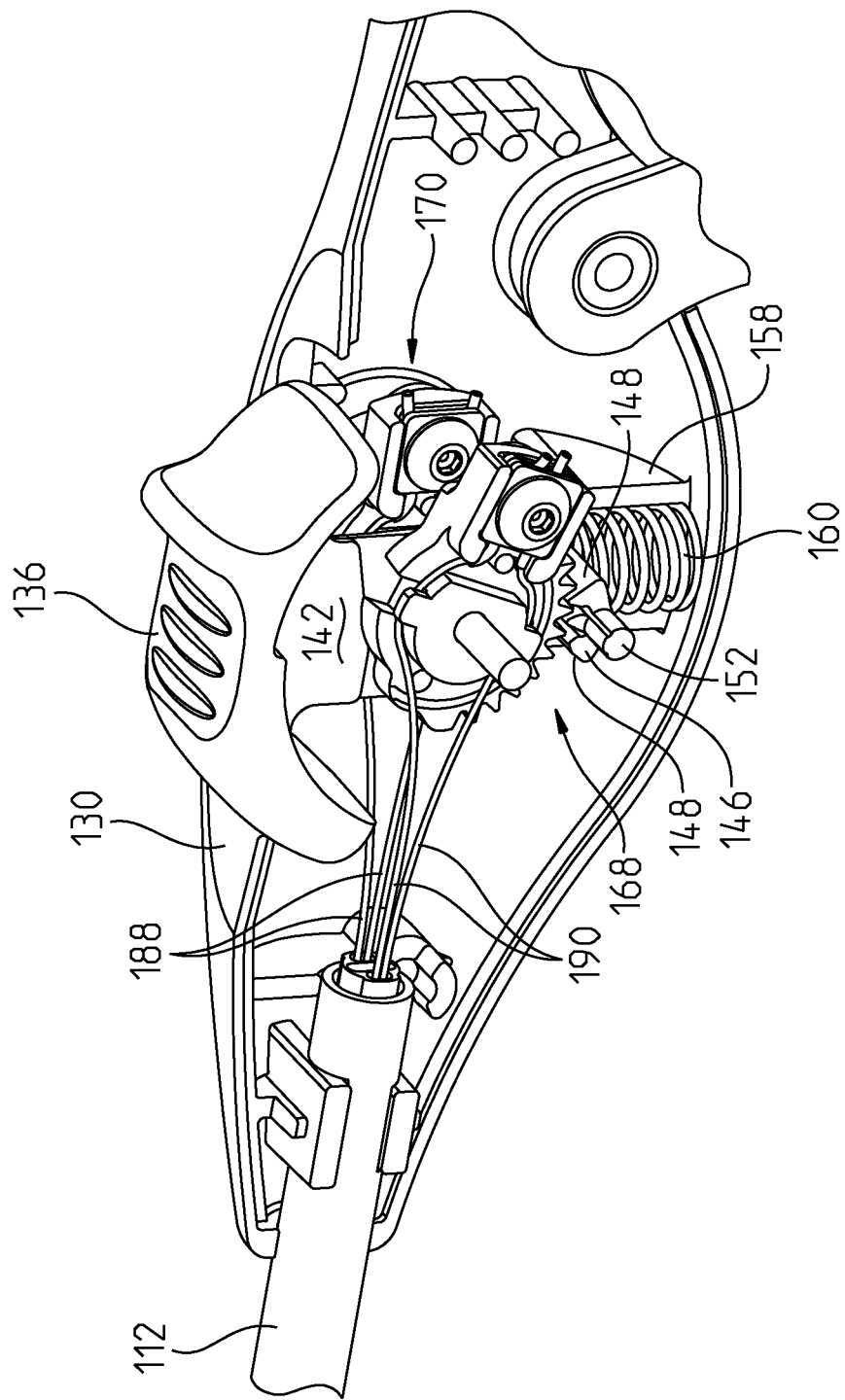
FIG. 5 is an elevated perspective view of a distal portion of the proximal end of the exemplary laparoscopic device of FIG. 2, without the left side housing and without the clip release wires and the draw wires, and with the pitch and yaw controls in an unlocked position.

Referring to FIG. 1, an exemplary clip deployment apparatus 100 comprises a controller 110 mounted to a proximal portion of a rigid or semi-rigid conduit 112 that is relatively linear. The controller 110 includes various controls in order to manipulate a repositionable mechanism operatively coupled to an end effector 118, where the repositionable mechanism is mounted to a distal portion of the conduit 112. In this exemplary embodiment, the repositionable mechanism is coupled to an end effector comprising a clip deployment device 118. But as will be discussed in more detail hereafter, the end effector 118 may comprise any number of devices such as, without limitation, forceps, ablation rails, jaws, linear cutters, ablation pens, ablation clamps, illuminated dissectors, and non-illuminated dissectors.

The exemplary repositionable mechanism incorporates a dual passive mechanism. The first passive mechanism is operative to control the pitch (i.e., up and down) of the end effector 118, while the second passive mechanism is operative to control the yaw (i.e., side to side) of the end effector.

Referencing FIGS. 1-10, the controller 110 is coupled to the conduit 112 in order to manipulate a repositionable mechanism operatively coupled to the end effector 118. The controller 110 comprises a right side housing 130 and a left side housing 132 that cooperatively define an internal cavity and corresponding openings to accommodate throughput of certain controls. A first of these openings is a dorsal opening 134 that accommodates throughput of a repositionable button 136. As will be discussed in more detail hereafter, the repositionable button 136 may be manipulated vertically to lock and unlock the repositionable mechanisms, as well as forward-to-rearward to lock and unlock the position of the button itself, in order to provide for or constrain lateral and vertical adjustability of the end effector 118.

The repositionable button 136 comprises a proximal-to-distal arcuate top 138 that includes bumps and a proximal ridge to accommodate the thumb of a user being positioned on top of the button. The medial-to-lateral width of the arcuate top 138 is generally constant and overlaps a vertical, planar appendage 142 that extends from the underside of the arcuate top. This vertical appendage 142 has a relatively constant and minimal medial-to-lateral dimension, but includes a proximal-to-lateral dimension that tapers from a maximum where the appendage extends from the arcuate top, to a minimum where the appendage ends. Extending through this vertical appendage 142 is a U-shaped through hole 144 that is partially occupied by an axle 164. This U-shaped through hole 144 allows the button 136 to be vertically repositioned with respect to the axle 164 so that active pressure is required to maintain a depressed button position when the axle is in a distal portion of the through hole. Instead of having to maintain pressure upon the button 136 to sustain it in a depressed position, the user may choose to rotate the button with respect to the axle 164 in order to seat the axle in a proximal portion of the through hole 144, thus effectively locking the button in the depressed position. In order to unlock the button 136, a user simply rotates or pushes the button proximally to cause the axle 164 into the distal portion of the through hole 144.

At the end of the appendage 142, a pair of tooth receivers 146 extend outward in the medial and lateral directions from opposing sides of the appendage. The tooth receivers 146 each include a series of longitudinal pyramidal shapes 148 that are in parallel and radially arranged in order to define a series of corresponding longitudinal pyramidal cavities 150. At the medial end of the medial tooth receiver 146 and at the lateral end of the lateral tooth receiver 146 is a cylindrical projection 152 that is received within corresponding vertical, oblong grooves 154 on the interior of the housings 130, 132. These grooves 154 inhibit significant medial-to-lateral and proximal-to-distal travel of the tooth receivers 146 as the tooth receivers are vertically repositioned. In other words, as the button 136 is depressed vertically, the toothed receivers 146 are vertically repositioned in a corresponding vertical manner. In this way, the movement of the toothed receivers 146 is directly attributable to the movement of the button 136 as the toothed receivers are indirectly mounted to the button via the appendage 142.

Figure 6:
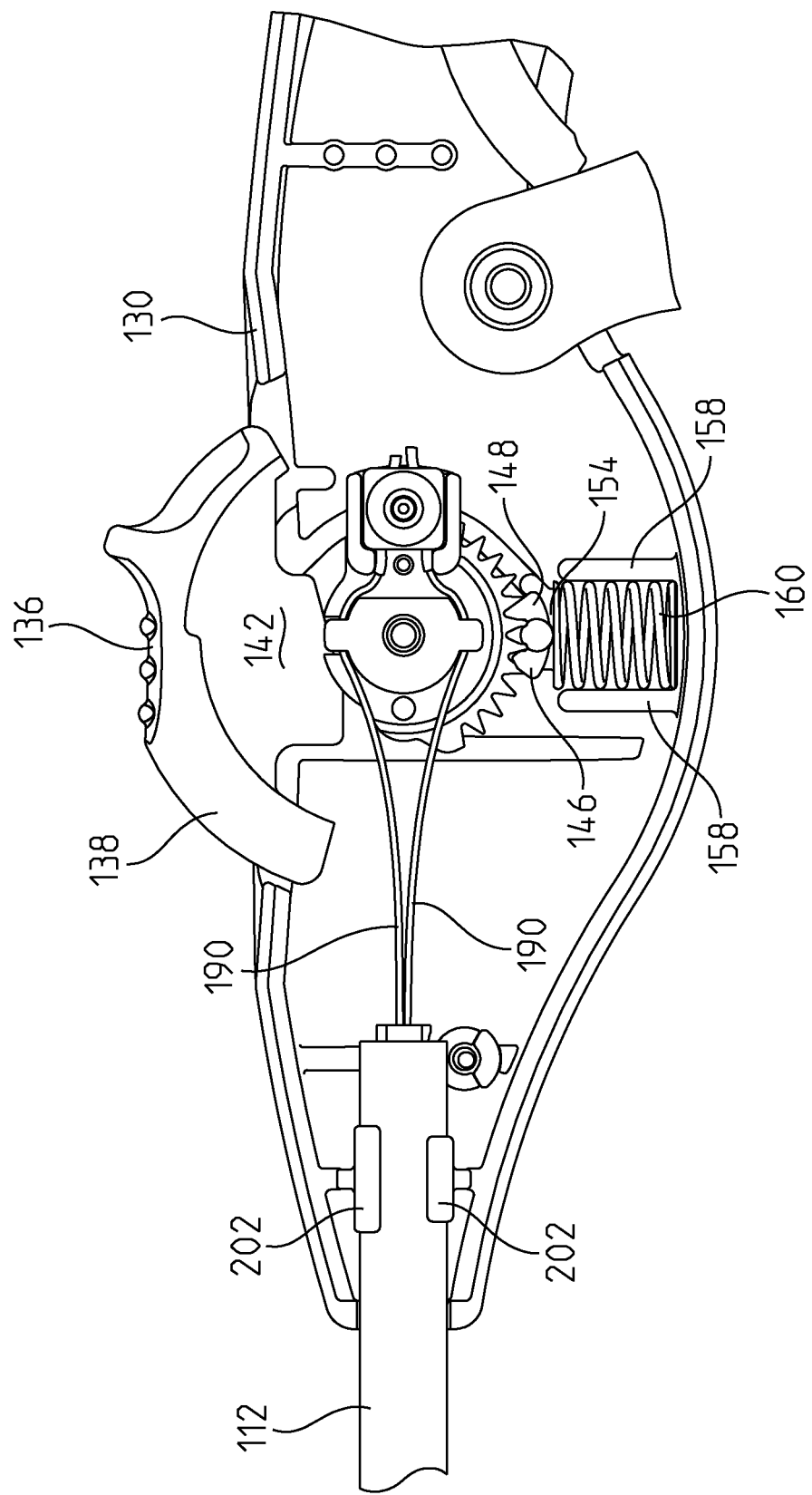
FIG. 6 is a profile view of a distal portion of the proximal end of the exemplary laparoscopic device of FIG. 2, without the left side housing and without the clip release wires and the draw wires, and with the pitch and yaw controls in a locked position.
Figure 7:
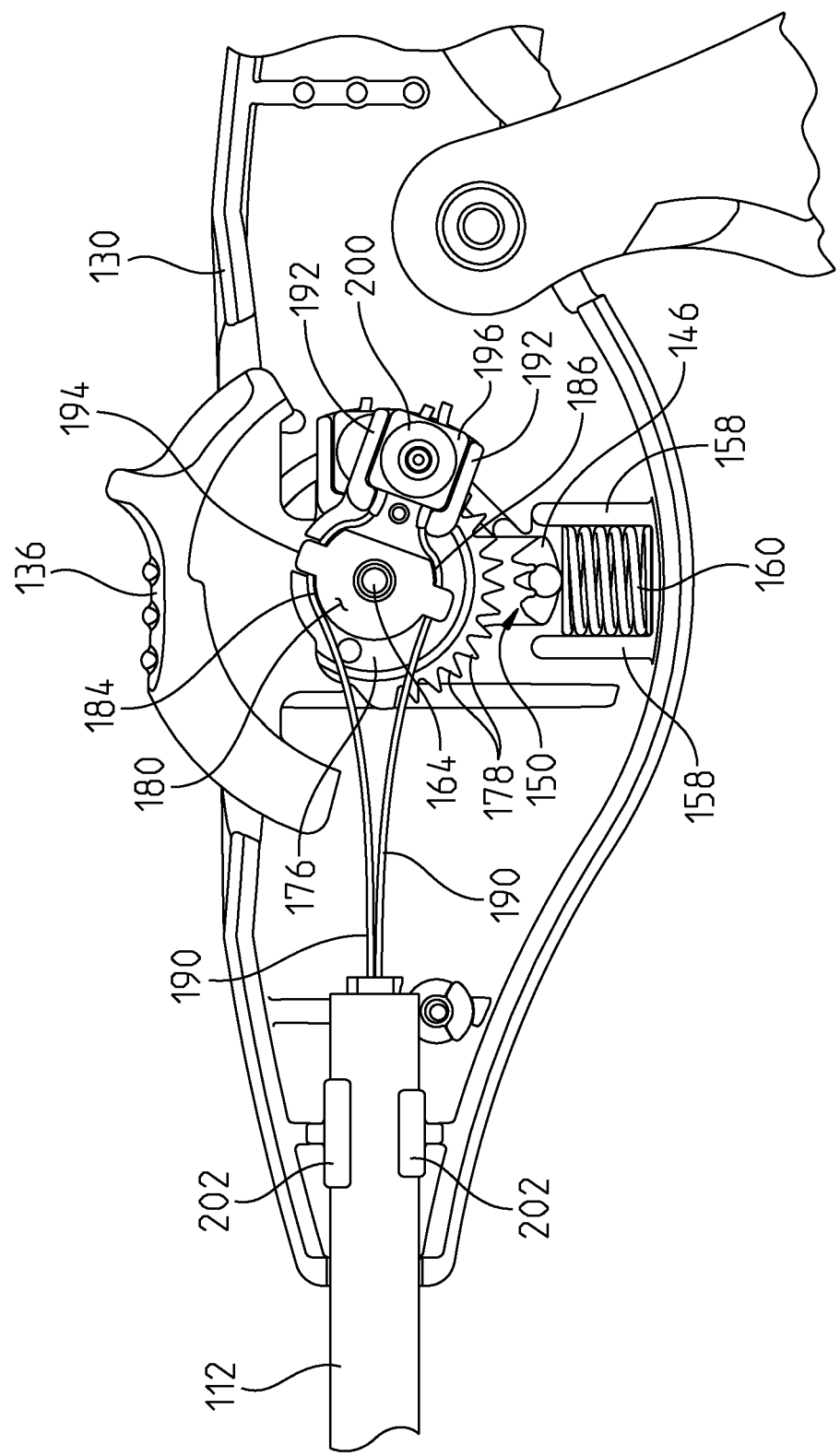
FIG. 7 is a profile view of a distal portion of the proximal end of the exemplary laparoscopic device of FIG. 2, without the left side housing and without the clip release wires and the draw wires, and with the pitch and yaw controls in the unlocked position.
Figure 8:
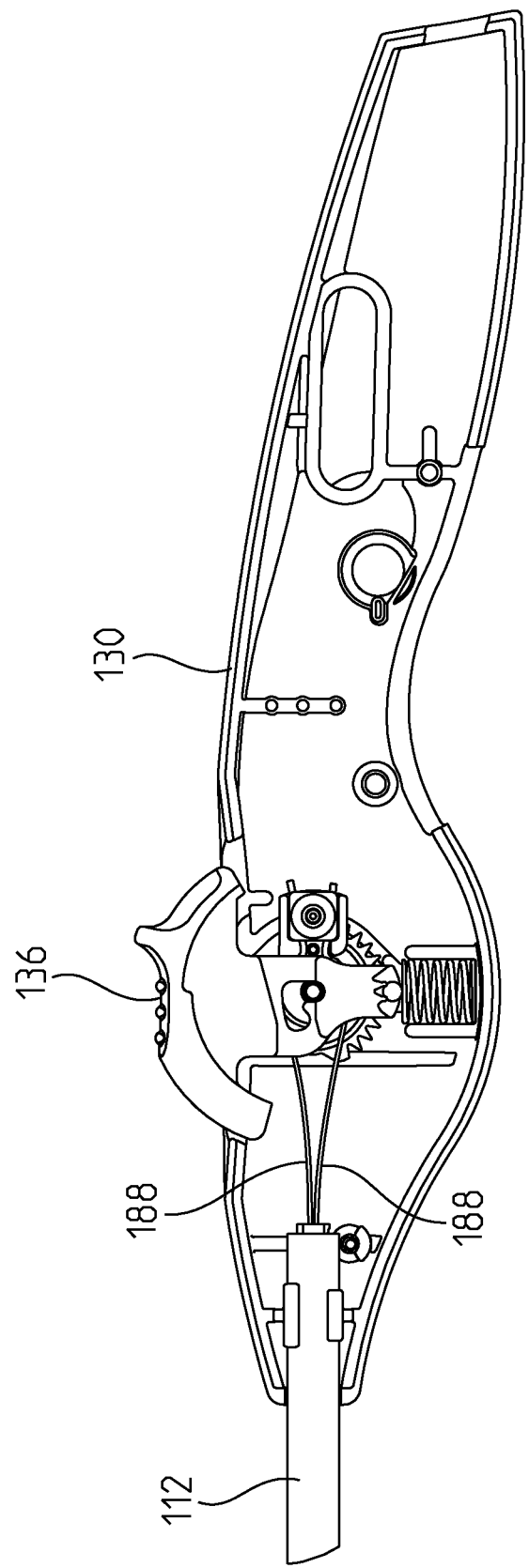
FIG. 8 is a profile view of a distal portion of the proximal end of the exemplary laparoscopic device of FIG. 2, without the left side housing, the clip release wires, the draw wires, and the yaw control.
Figure 9:
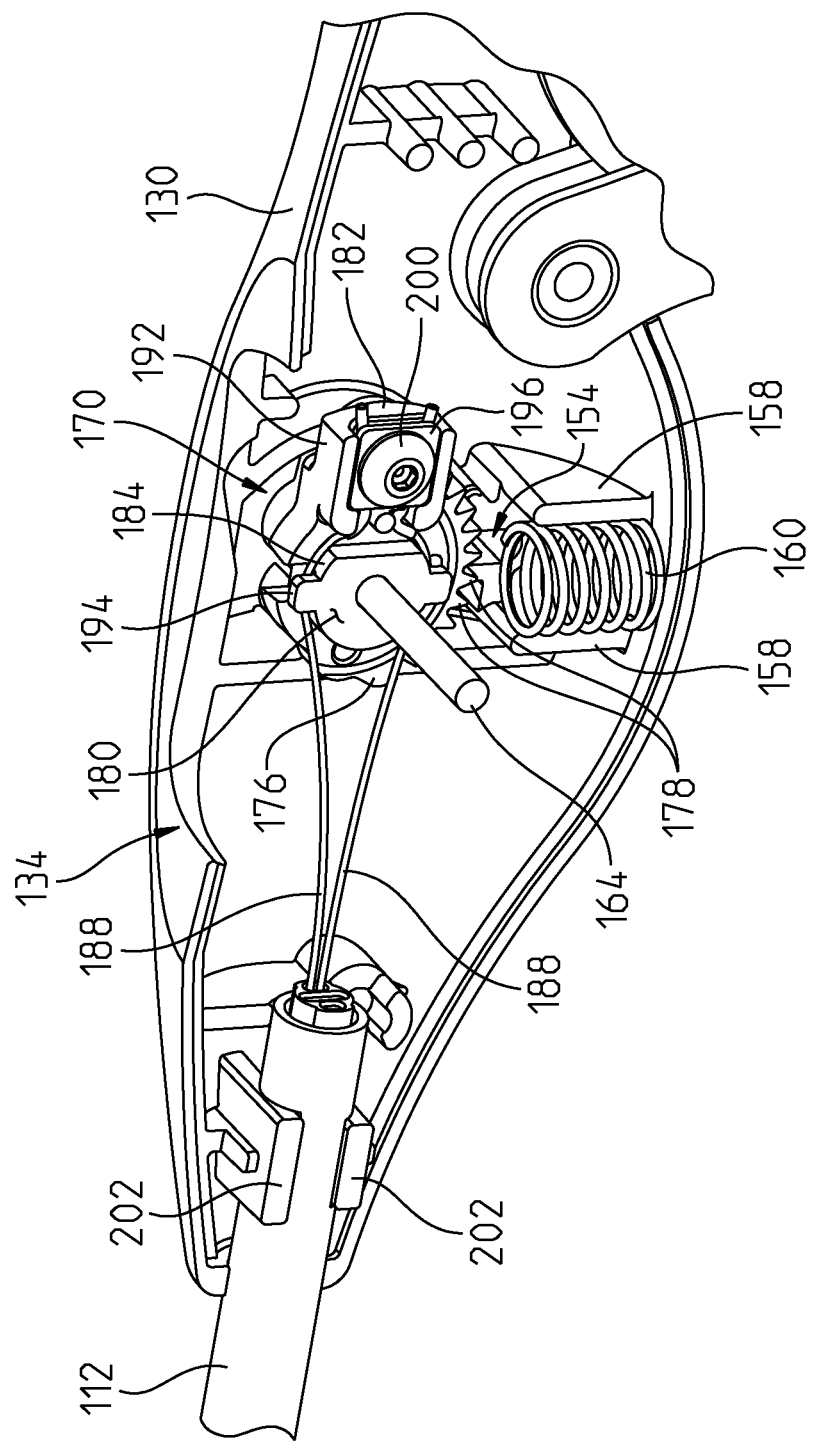
FIG. 9 is an elevated perspective view of a distal portion of the proximal end of the exemplary laparoscopic device of FIG. 2, without the left side housing, the clip release wires, the draw wires, and the yaw control.
Figure 10:
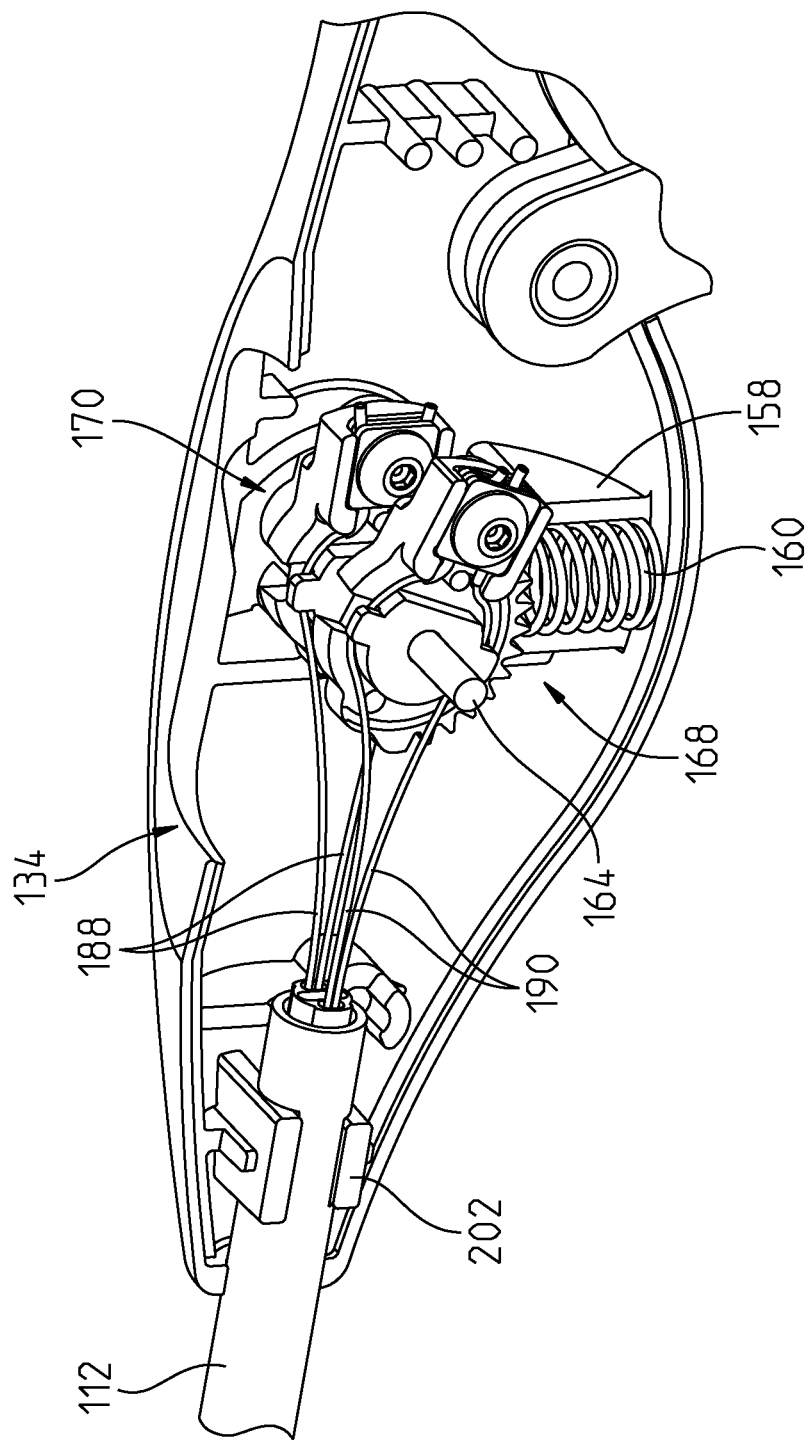
FIG. 10 is an elevated perspective view of a distal portion of the proximal end of the exemplary laparoscopic device of FIG. 2, without the left side housing, the clip release wires, the draw wires, and the control button.
Figure 11:
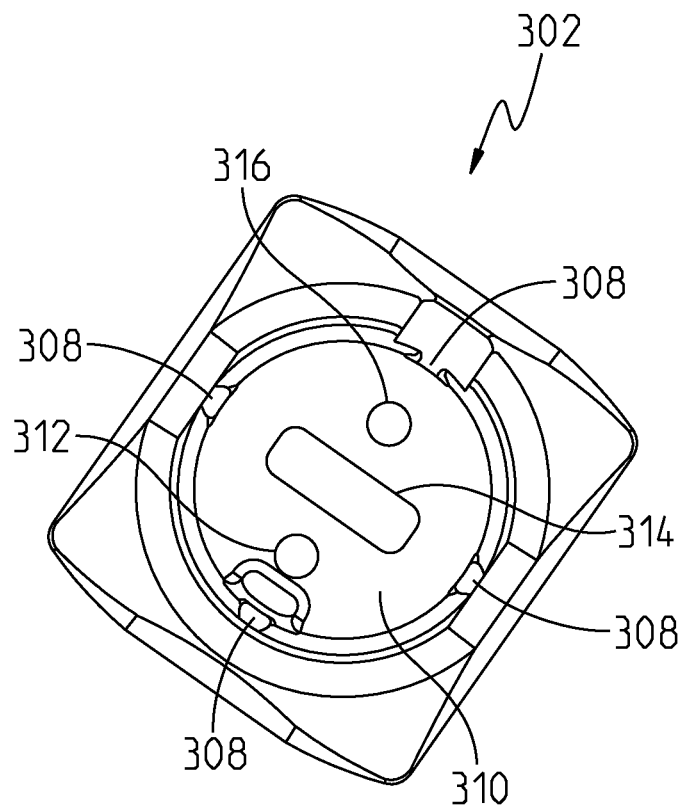
FIG. 11 is an end view, from the proximal end, of an exemplary clevis of the exemplary laparoscopic device of FIG. 1.
Figure 12:
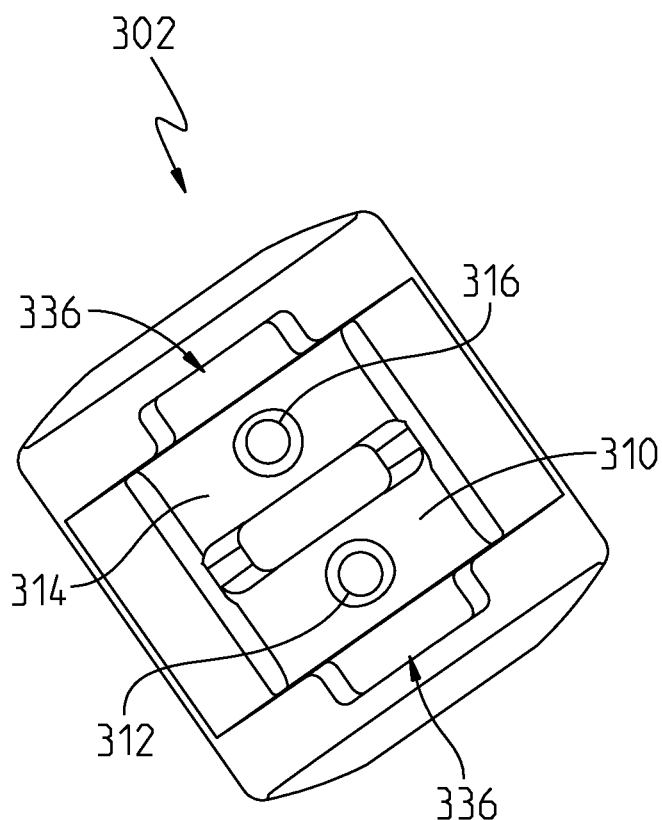
FIG. 12 is an end view, from the distal end, of the exemplary clevis of FIG. 11.
Figure 13:
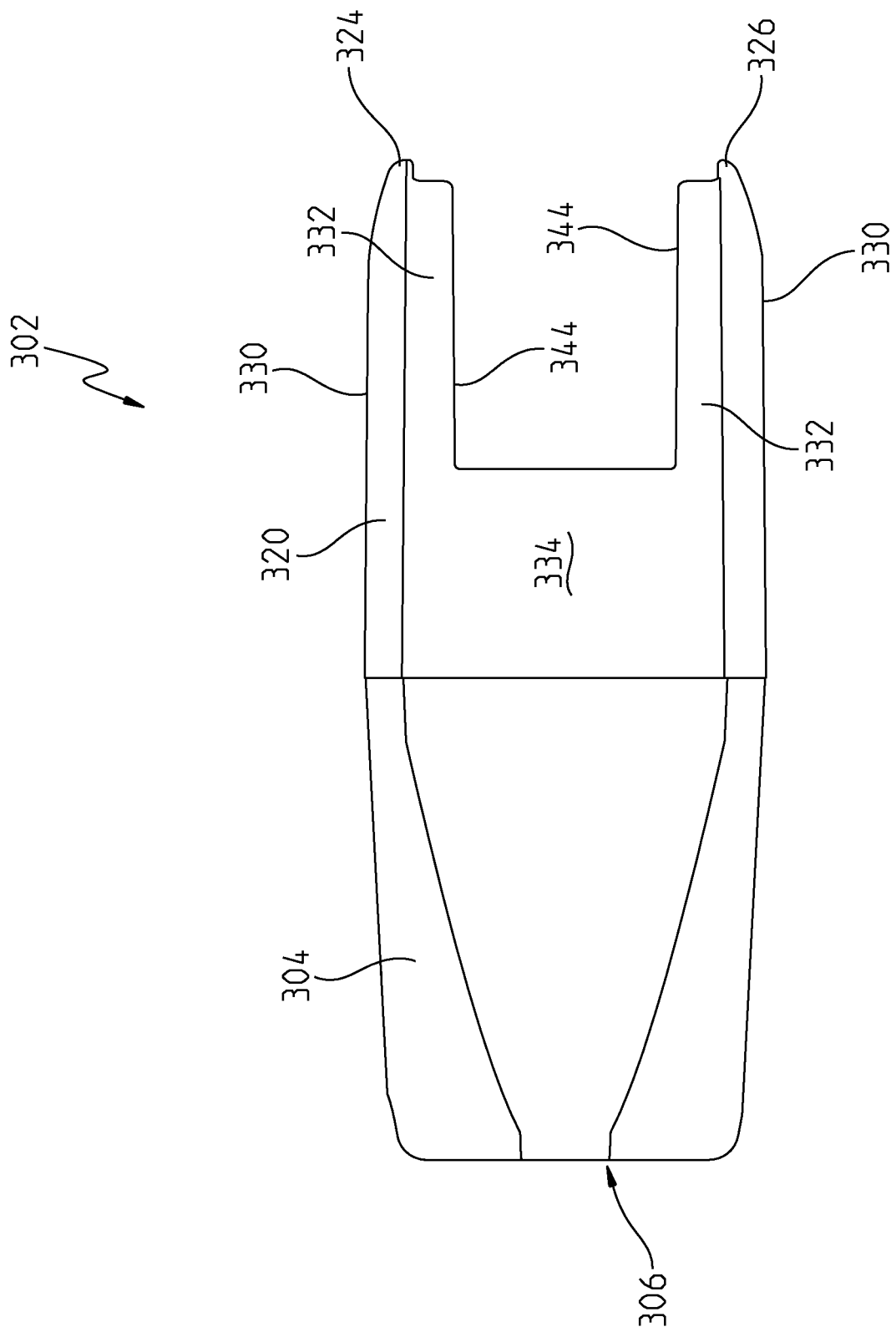
FIG. 13 is a profile view of the exemplary clevis of FIG. 11.
Figure 14:
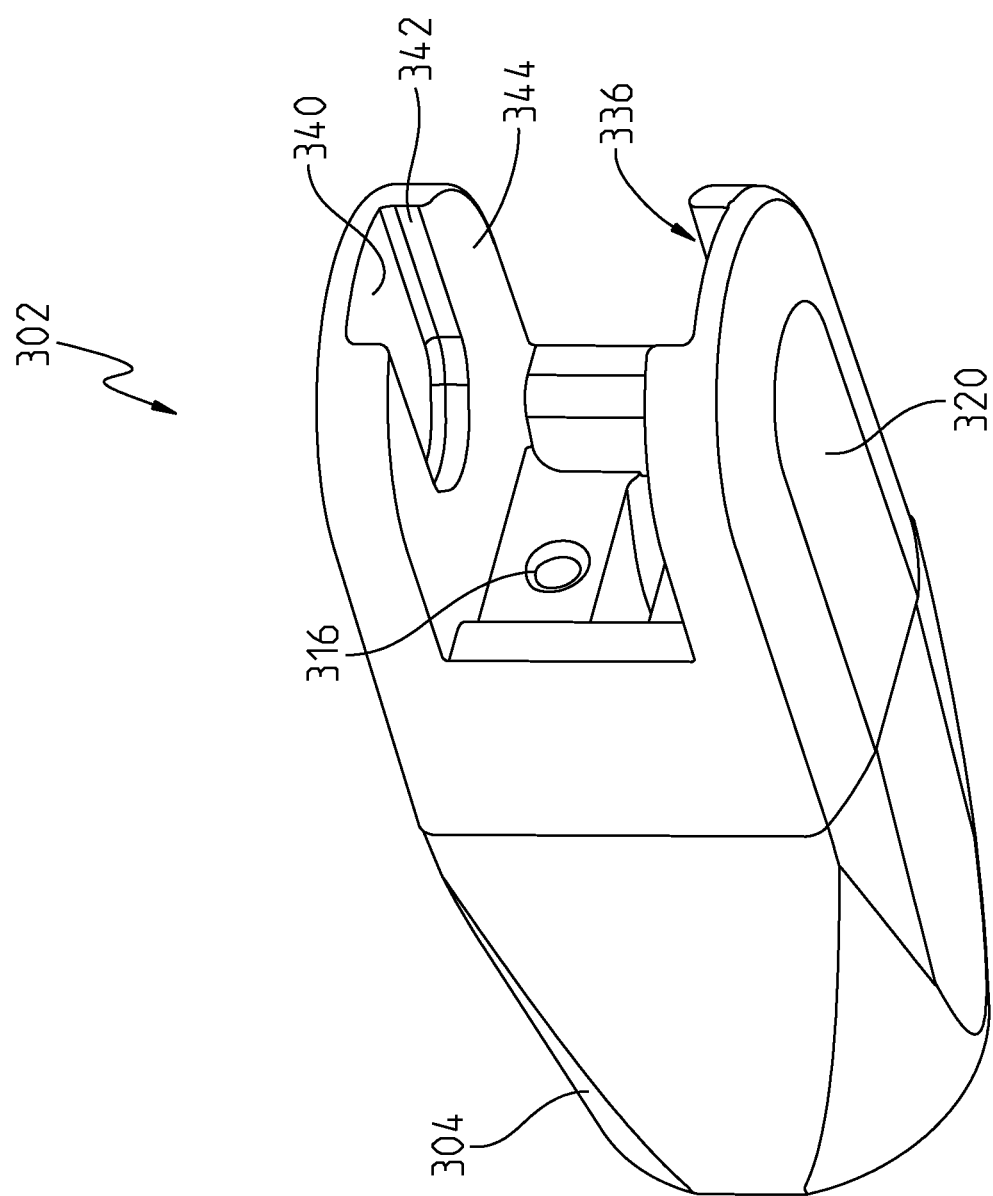
FIG. 14 is an elevated perspective view of the exemplary clevis of FIG. 11.
Figure 15:
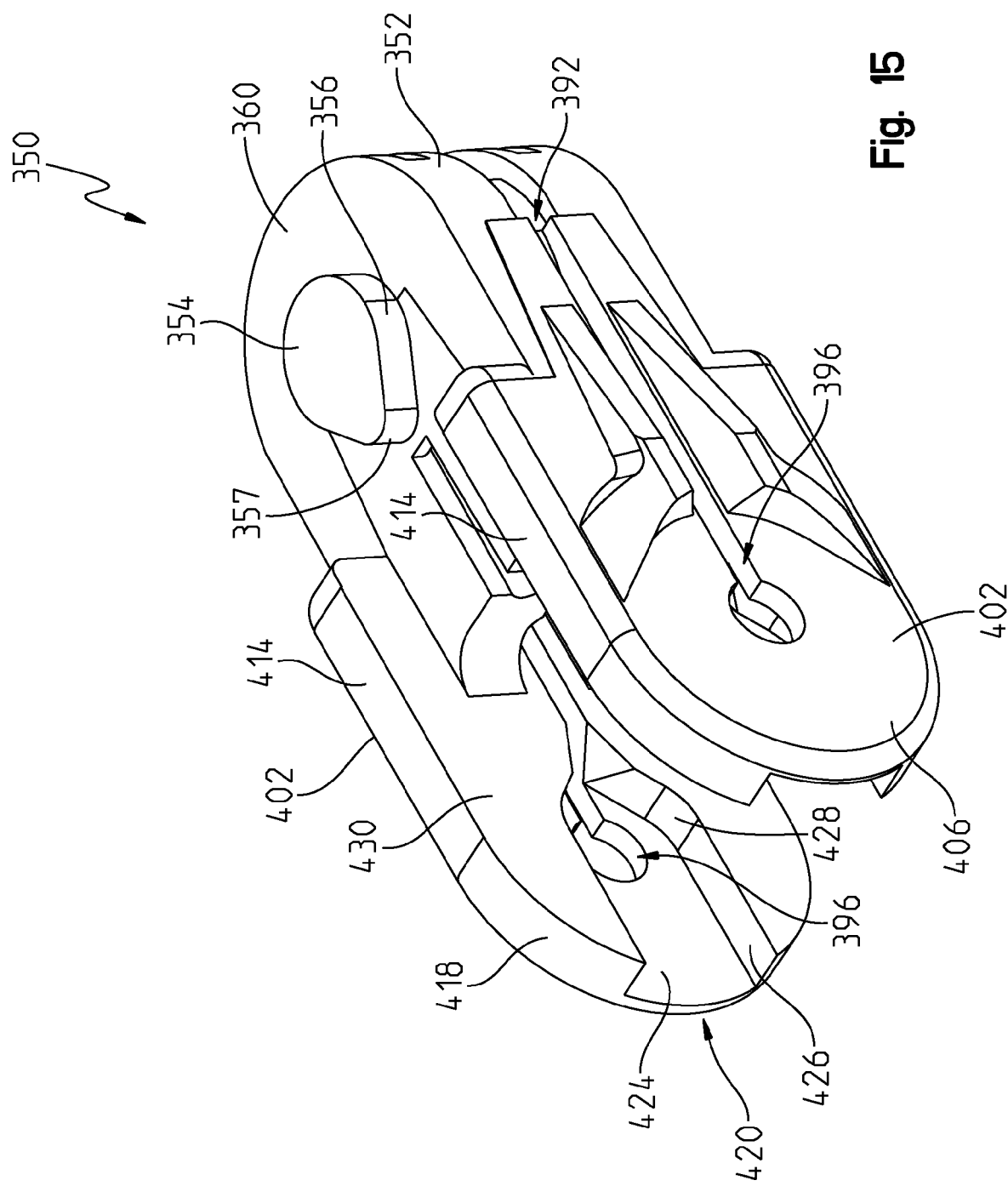
FIG. 15 is an elevated perspective view, from a distal end, of an exemplary dual pivot joint of the exemplary laparoscopic device of FIG. 1.
Figure 16:
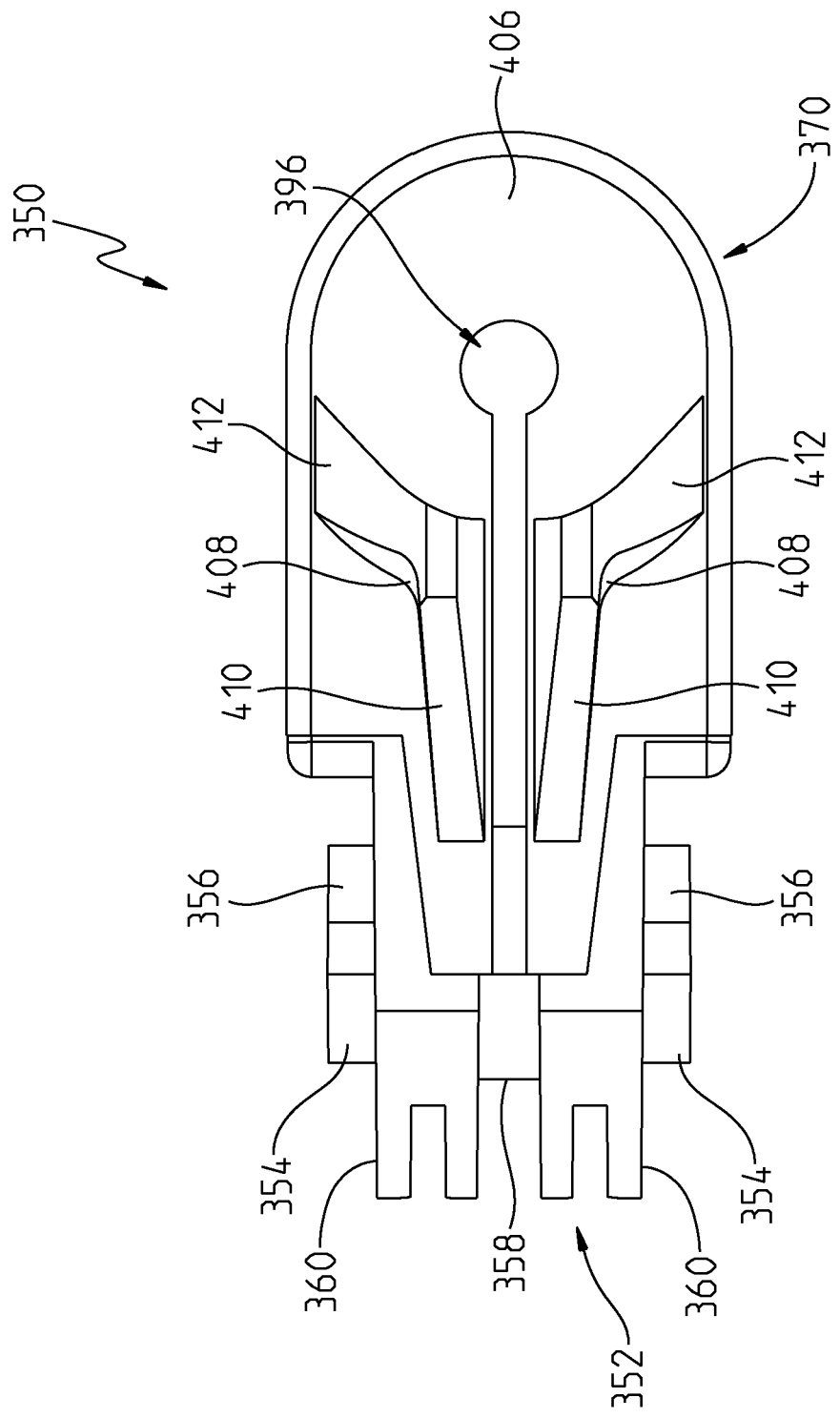
FIG. 16 is a profile view of the exemplary dual pivot joint of FIG. 15.
Figure 17:
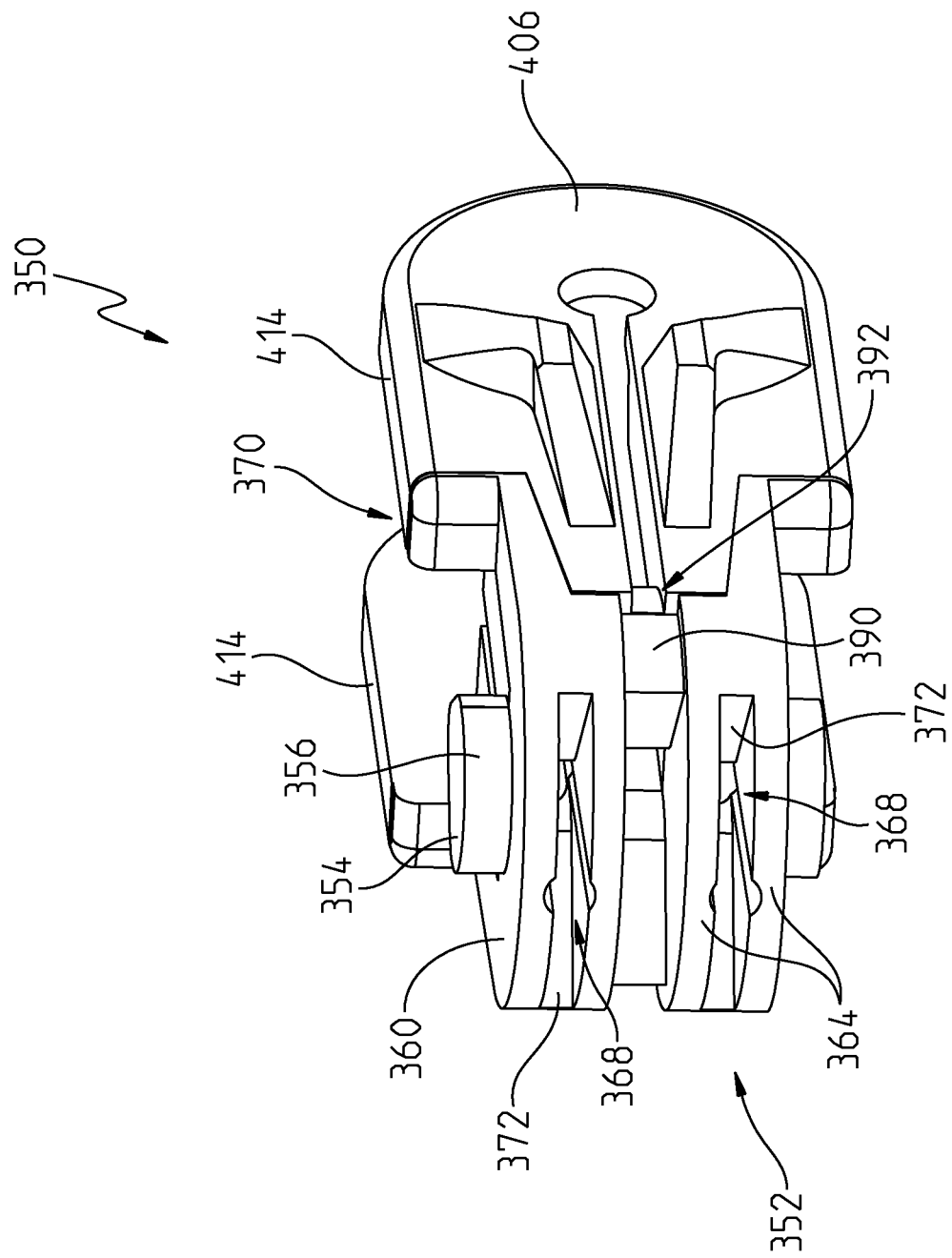
FIG. 17 is an elevated perspective view, from a proximal end, of the exemplary dual pivot joint of FIG. 15.
Figure 18:
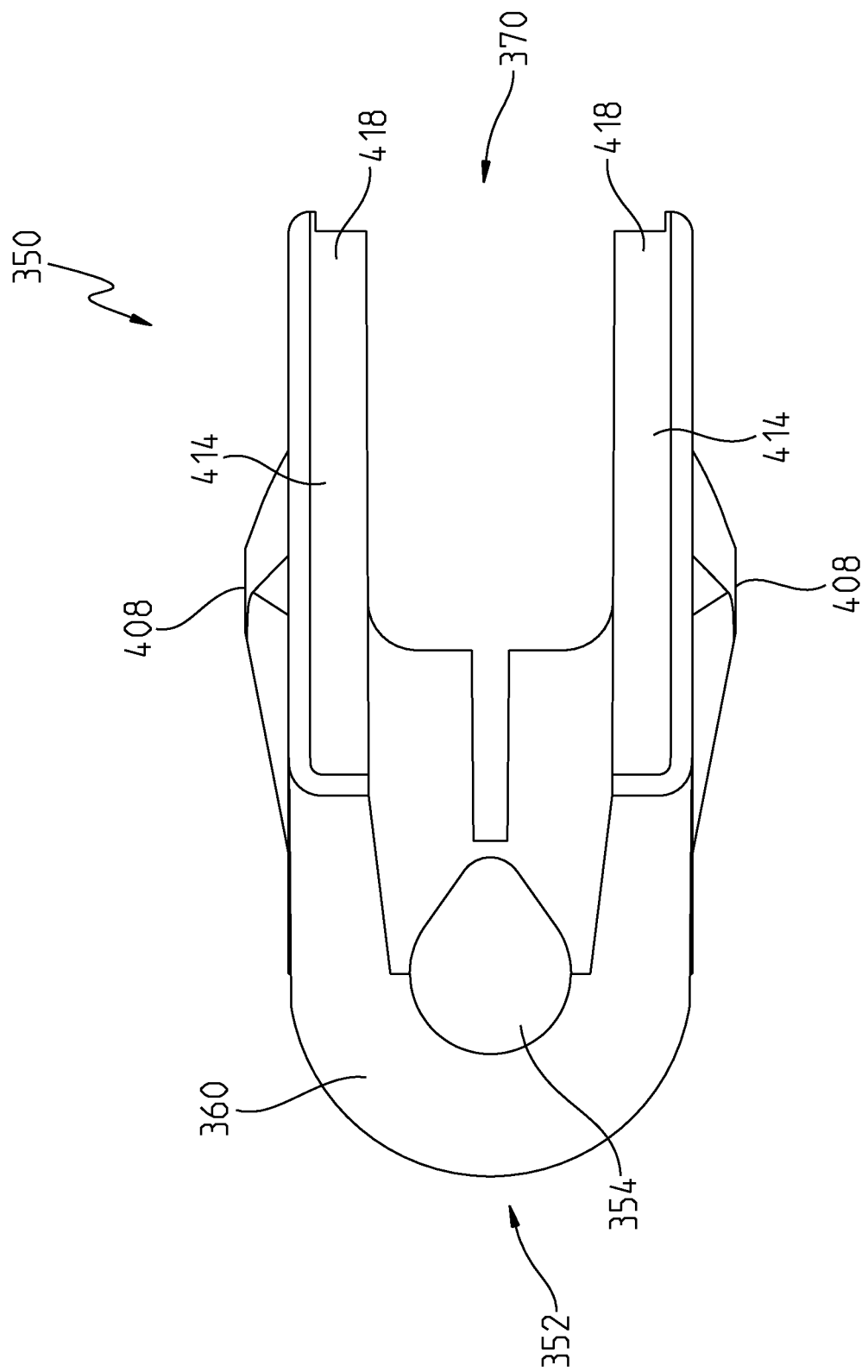
FIG. 18 is a top view of the exemplary dual pivot joint of FIG. 15.
Figure 19:
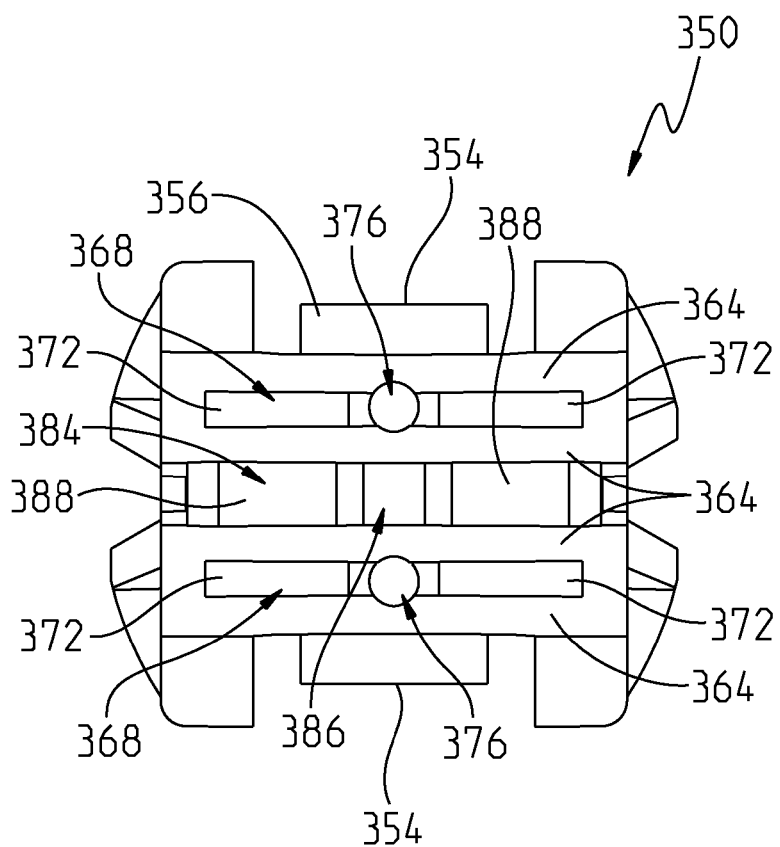
FIG. 19 is an end view, from the proximal end, of the exemplary dual pivot joint of FIG. 15.
Figure 20:
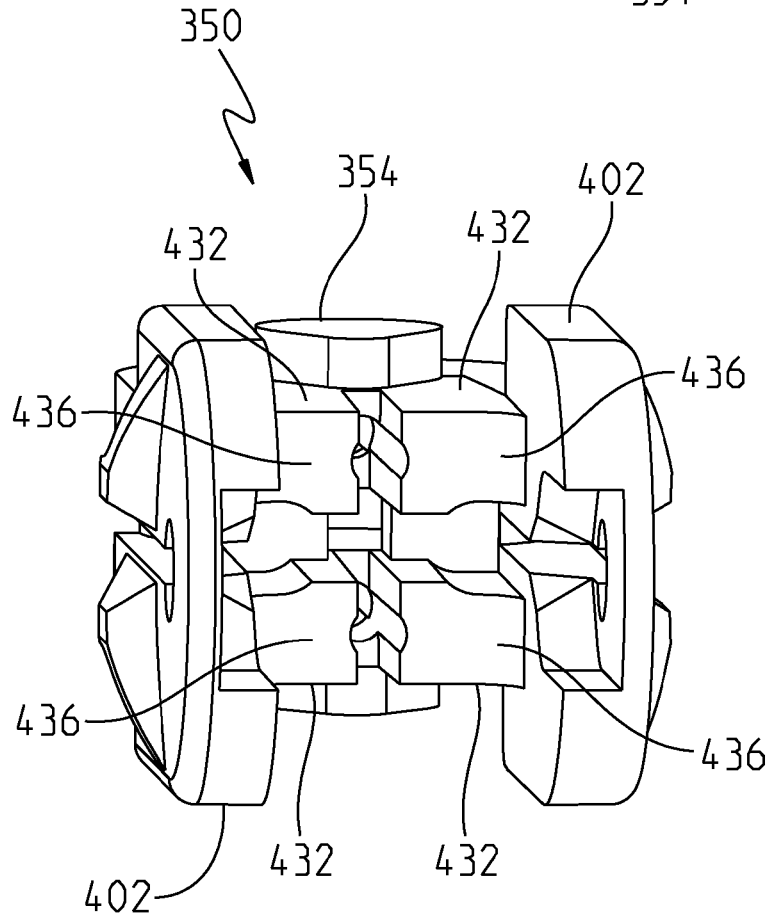
FIG. 20 is another elevated perspective view, from a distal end, of the exemplary dual pivot joint of FIG. 15.
Figure 21:
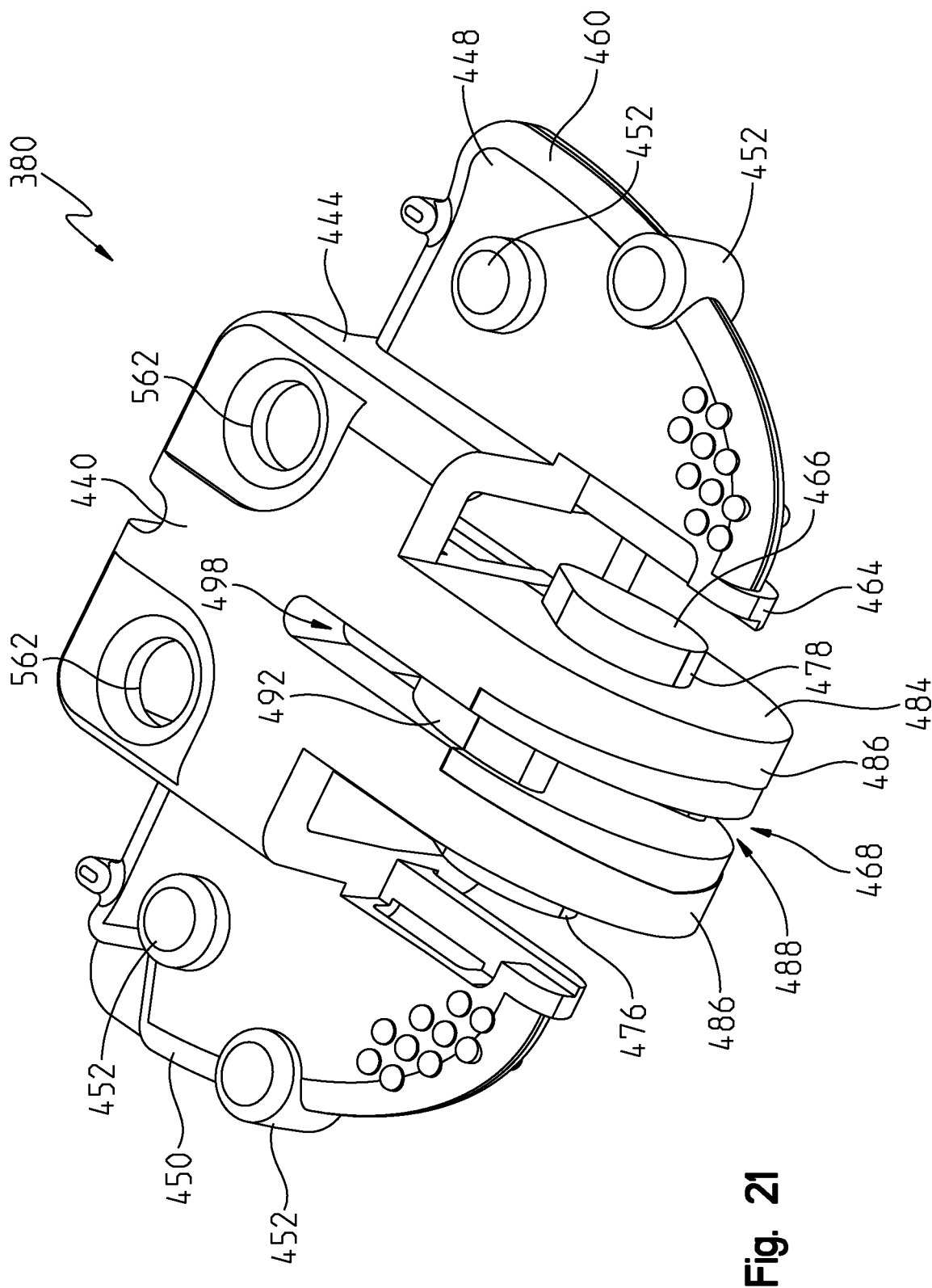
FIG. 21 is an elevated perspective view, from a proximal end, of an exemplary yoke of the exemplary laparoscopic device of FIG. 1.
Figure 22:
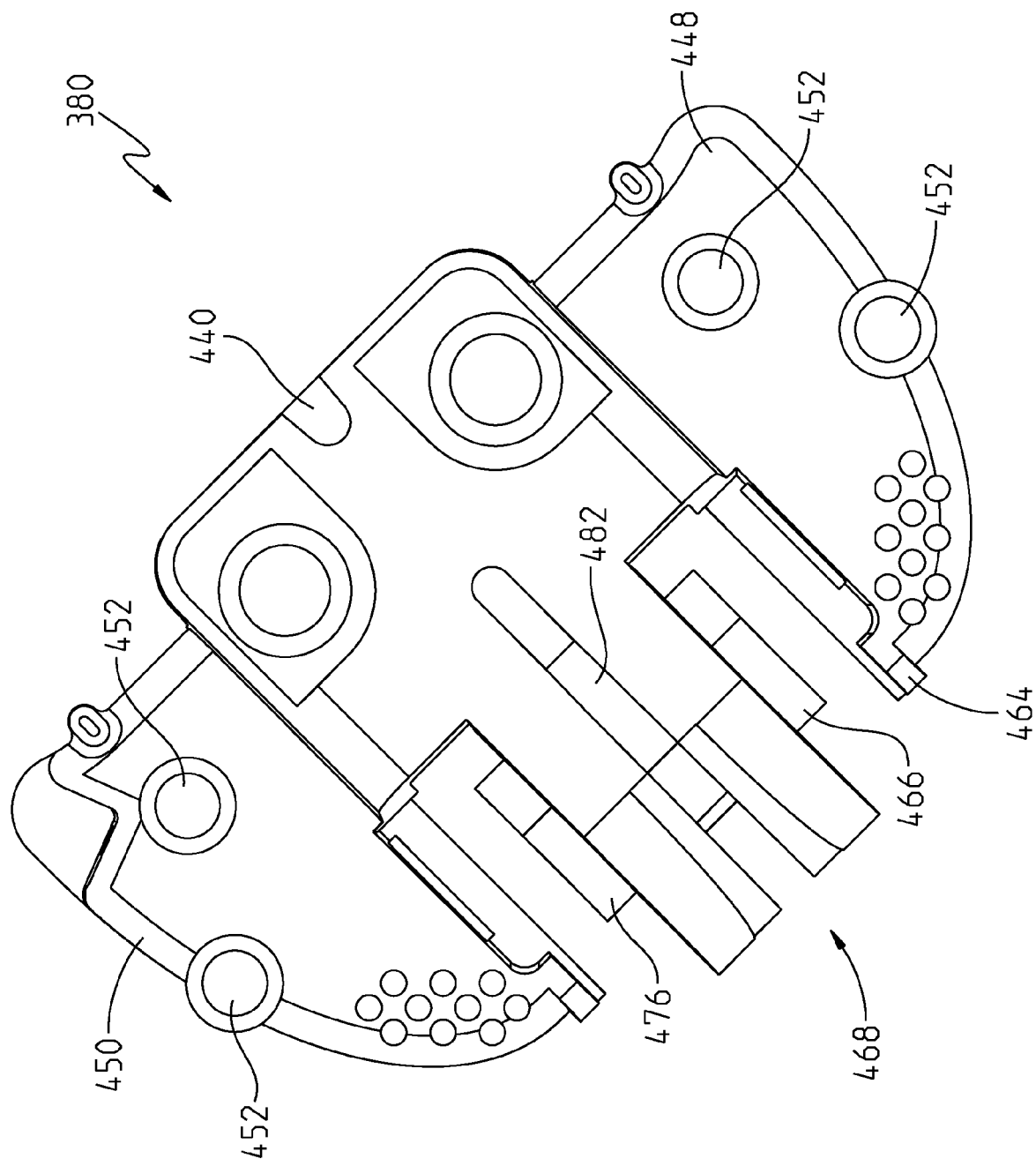
FIG. 22 is a top view of the exemplary yoke of FIG. 21.
Figure 23:
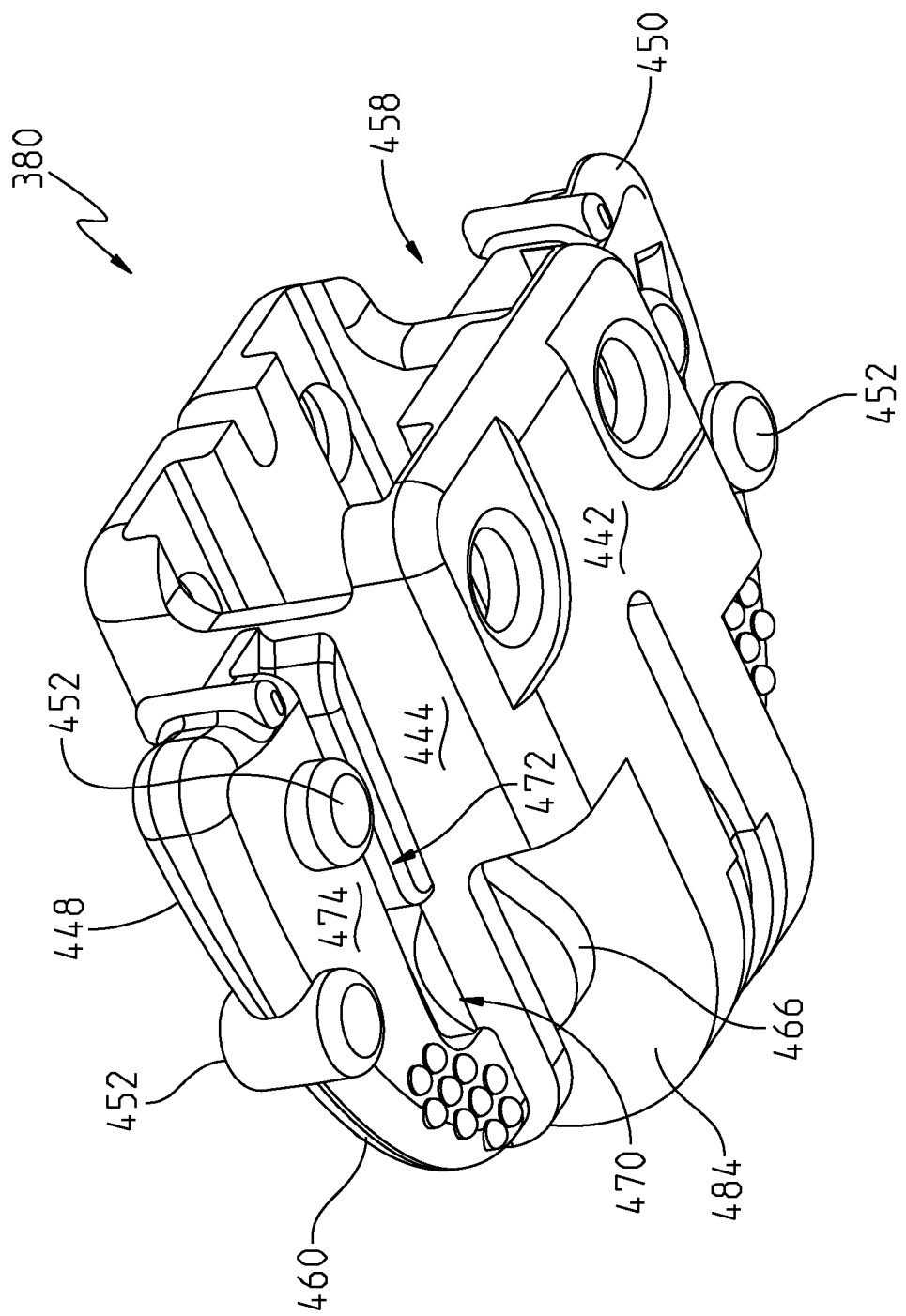
FIG. 23 is an underneath perspective view, from a lateral side, of the exemplary yoke of FIG. 21.
Figure 24:
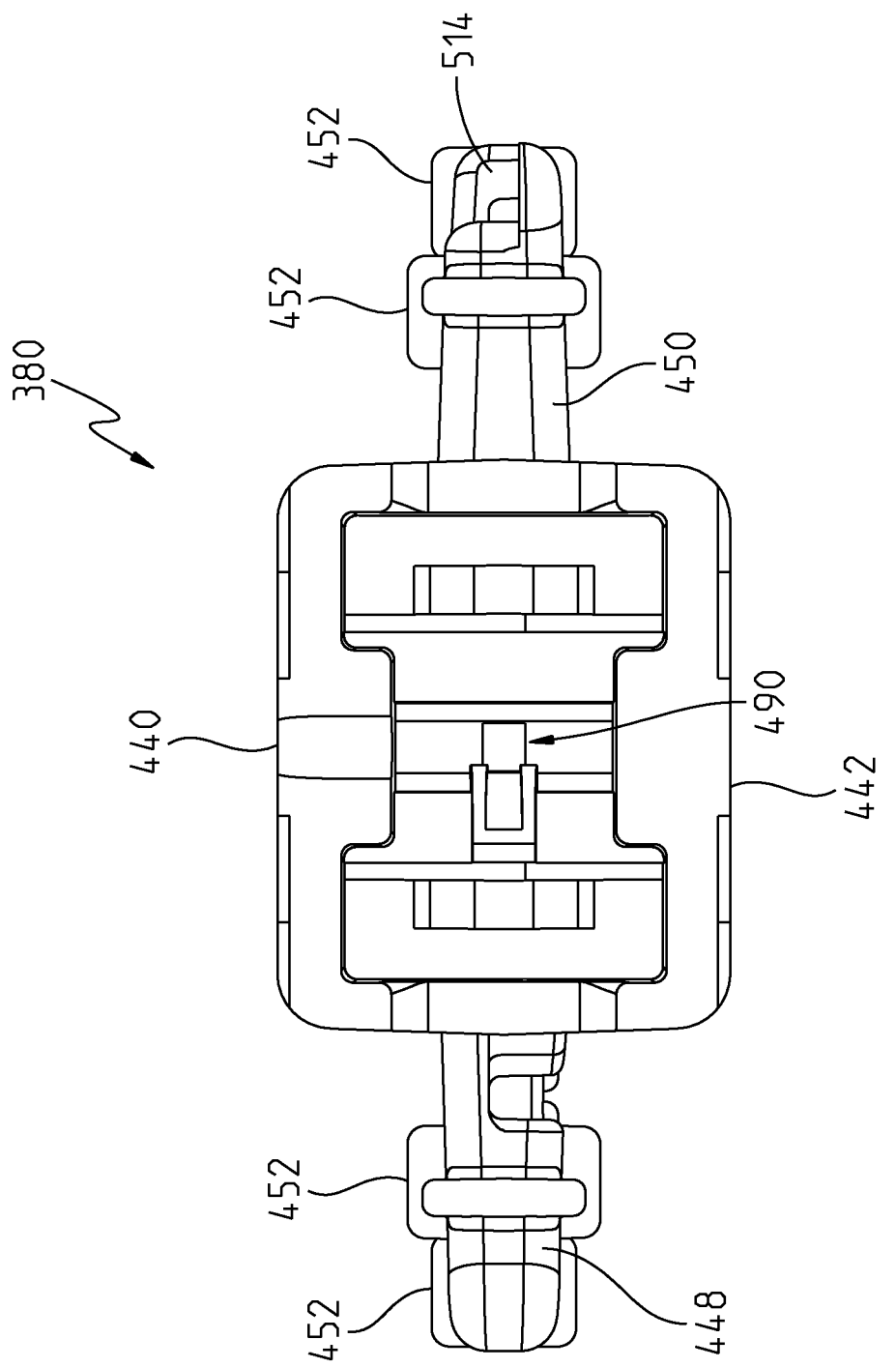
FIG. 24 is a distal view of the exemplary yoke of FIG. 21.
Figure 25:
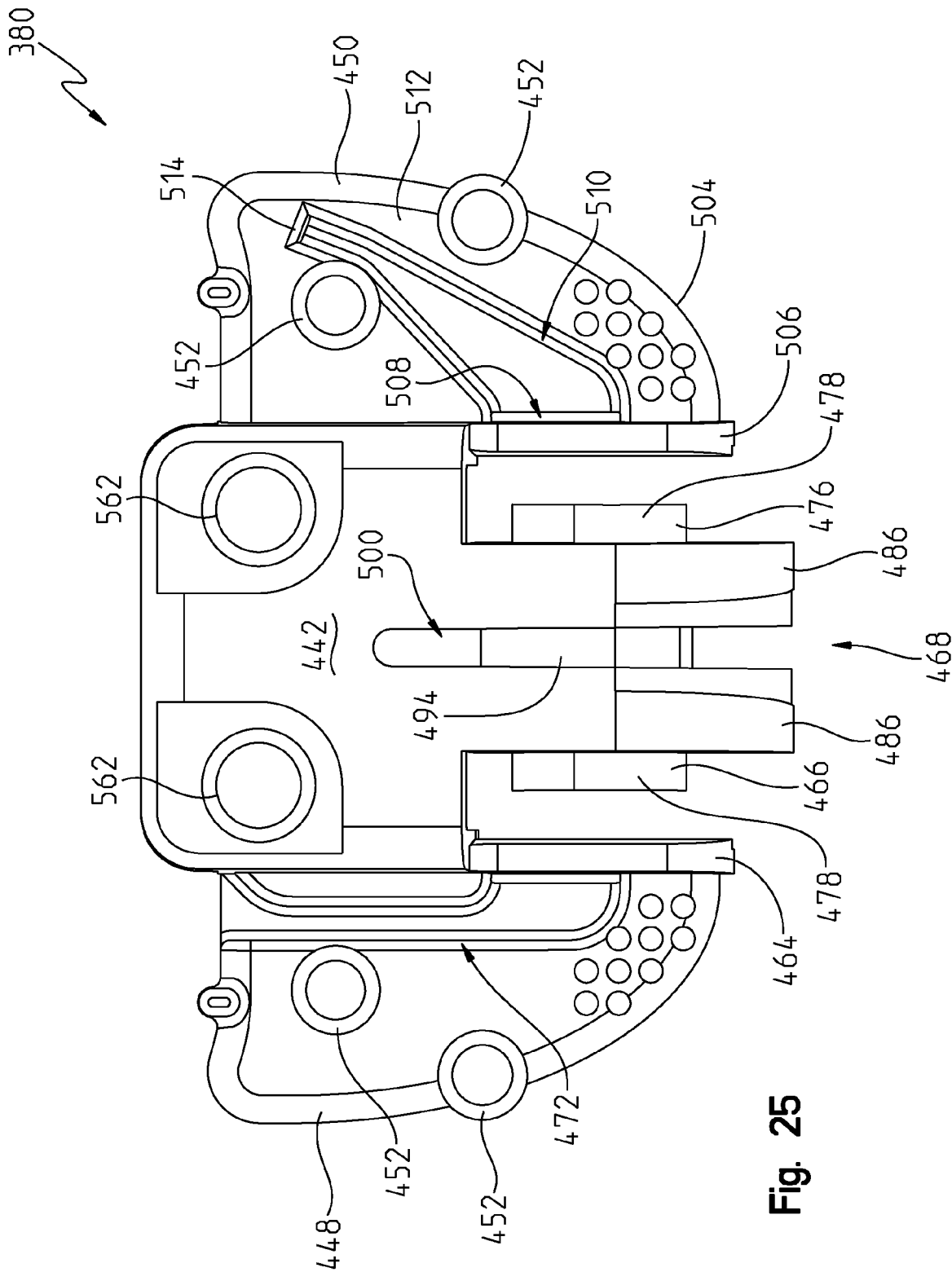
FIG. 25 is a bottom view of the exemplary yoke of FIG. 21.
Figure 26:
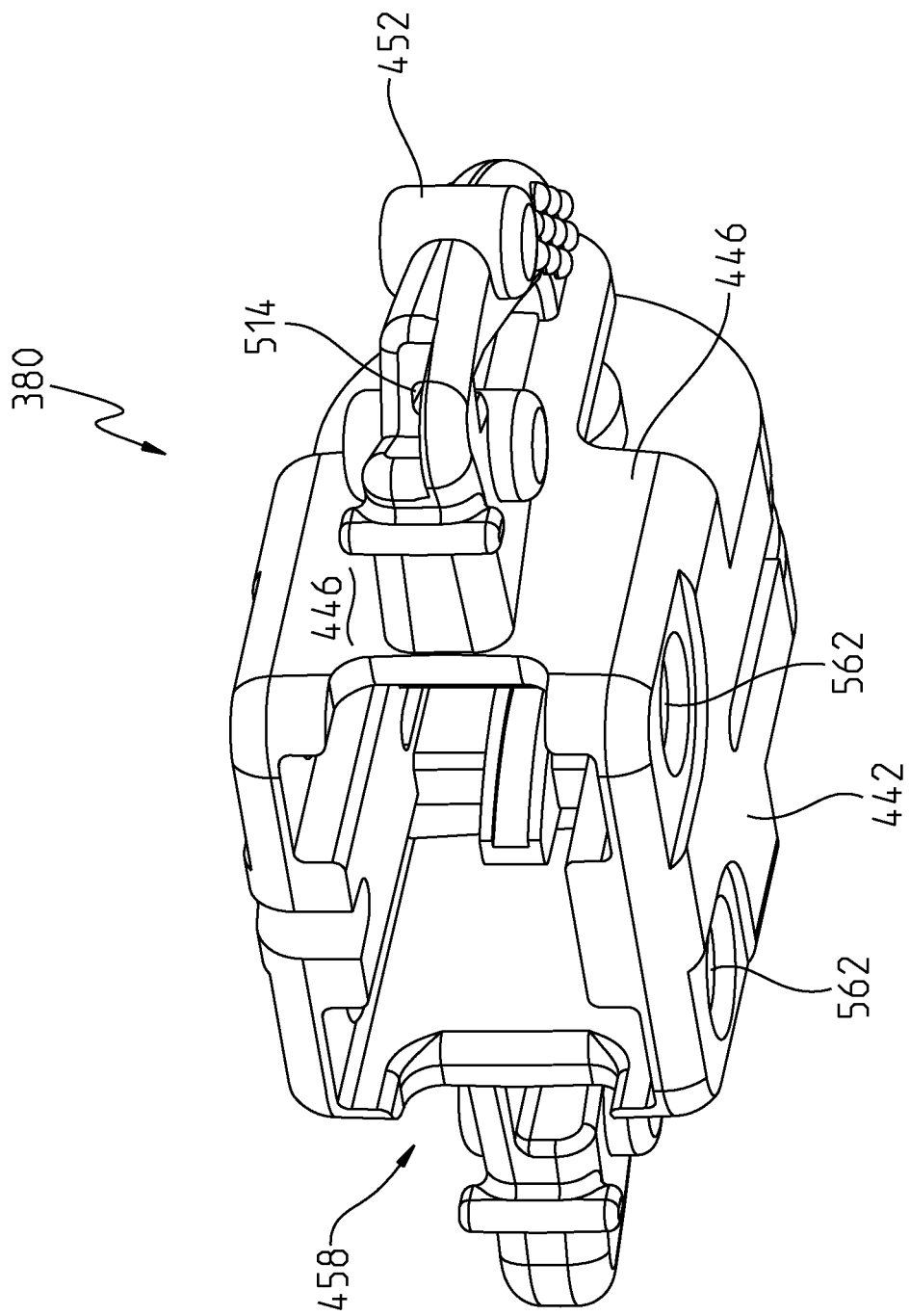
FIG. 26 is another underneath perspective view, from the opposite lateral side, of the exemplary yoke of FIG. 21.
Figure 27:
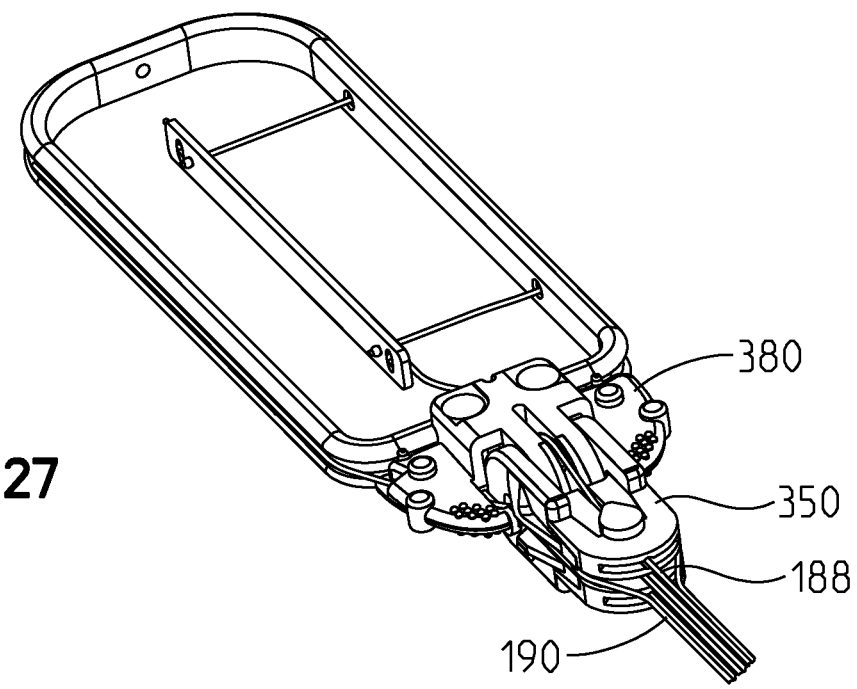
FIG. 27 is an elevated perspective view, from the proximal end, of the exemplary dual pivot joint and yoke mounted to a clip deployment device, where the view shows the both sets of connection wires, the draw wires, and the clip release wires.
Figure 28:
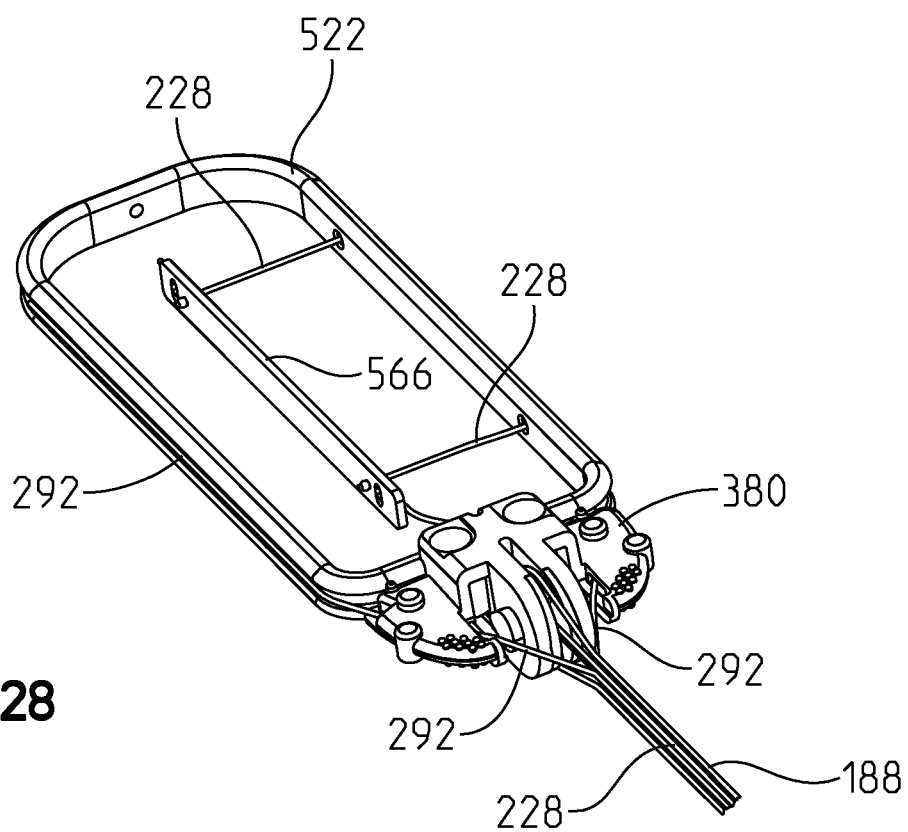
FIG. 28 is an elevated perspective view, from the proximal end, of the exemplary yoke mounted to a clip deployment device, where the view shows one set of connection wires, the draw wires, and the clip release wires.

The button 136 is biased vertically to its highest vertical position shown in FIG. 6. To achieve this bias, the housings 130, 132 include parallel walls 158 that cooperate to form medial-to-lateral trench within which at least one spring 160 is seated. The spring 160 is rated at a sufficient spring force to overcome the weight of the button 136, appendage 142, tooth receivers 146, and cylindrical projections 152 to force the button to its highest vertical position. But the spring force is not so great that it requires too great a force from a user's thumb to depress the button 136 and overcome the bias of the spring 160.

An axle 164 extends in the medial-to-lateral direction within the interior cavity cooperatively defined by the housings 130, 132. This axle 164 is cylindrical in shape and includes a constant longitudinal diameter, thereby giving the axle a circular circumference. In exemplary form, the medial and lateral ends of the axle 164 are received within corresponding cylindrical cavities (not shown) on the interior of the housings. The depth of these cavities is not so great as to cover the majority of the axle 164. The exposed cylindrical portion of the axle 164 is operative to receive a pair of toothed assemblies 168, 170 that are interposed by the appendage 142, which itself includes a vertical, oblong orifice (not shown) to accommodate throughput of the axle and vertical travel of the appendage with respect to the axle, which has a fixed orientation. In exemplary form, the toothed assemblies 168, 170 include a through cylindrical orifice 172 allowing the assemblies to rotate on the outside of the axle.

Each of the toothed assemblies 168, 170 are identical to each other. Accordingly, a redundant description of the second toothed assembly has been omitted in furtherance of brevity. The toothed assemblies 168, 170 include a wheel 176 having circumferentially distributed teeth 178 that are sized to engage a respective tooth receivers 146 and be received within the longitudinal pyramidal cavities 150 when the tooth receivers in a raised vertical position (see FIG. 6). In exemplary form, the spring rate of the spring 160 is chosen to allow the tooth receivers 146 to be depressed by forces applied to the toothed assemblies 168, 170 above a predetermined threshold. For example, a high load applied to the end effector in any one direction may result in repositioning of one or both of the toothed assemblies 168, 170, thereby causing a wheel 176 and its teeth 178 to rotate and correspondingly depress against the corresponding tooth receiver 146, which depresses against the spring 160 to compress the spring, thus allowing one or both wheels to rotate to avoid breaking any of the components.

The wheel 176 has a generally uniform width but for a pair of outgrowths 180, 182. The first outgrowth 180 is generally centered radially with respect to the wheel and partially defines the through orifice 172 that receives the axle 164. This first outgrowth 180 is semicircular in shape extends medially from the wheel 176 and includes a corresponding top and bottom arcuate surfaces 184, 186 that are radially inset with respect to the wheel. These arcuate surfaces 184, 186 act as camming surfaces for respective connection wires 188, 190 that extend from the second outgrowth 182. The first outgrowth 180 also includes a pair of vertical flanges 194 that extend from the arcuate surfaces 184, 186 and cooperate with the circumferential ends of the wheels in order to provide medial and lateral guides for the connection wires 188, 190 so that the connection wires stay therebetween. The second outgrowth 182 is proximally oriented with respect to the first outgrowth 180 and includes a rectangular profile with a pair of L-shaped walls 192 and floor 196 cooperating to define an internal cavity. An opening (not shown) extends through the floor and into the cavity. This opening receives a fastener (such as a screw) 200 around which the connection wires 188, 190 are wound and secured in place. The fastener 200 is also recessed within the cavity so that the L-shaped walls 192 extend laterally beyond the end of the fastener. Accordingly, the connection wires 188, 190 extending from the fastener are threaded through a gap between the L-shaped walls 192, with one of the wires being threaded over the top arcuate surface 184, while the second wire is threaded under the bottom arcuate surface 186. Thereafter, the wires 188, 190 extend distally and taper to extend through a respective eyelet opening at the proximal end of the conduit 112.

Each of the toothed assemblies 168, 170 is independently rotatably repositionable with respect to one another. The first toothed assembly 168 is operative provide part of a passive repositionable mechanism in order to control the pitch (i.e., up and down) of the end effector 118, while the second toothed assembly 170 is operative to provide part of a passive repositionable mechanism in order to control the yaw (i.e., side to side) of the end effector. In exemplary form, when the button 136 is not depressed, the spring 160 is operative to bias the toothed receivers 146 into engagement with the teeth 178 of the toothed assemblies 168, 170, thereby inhibiting rotation of the toothed assemblies around the axle 164. When the tooth assemblies 168, 170 are locked in position (see FIG. 6) the end effector 118 cannot be repositioned in the vertical direction (i.e., affecting pitch) or in the medial-to-lateral direction (i.e., affecting yaw). Thus, when the tooth assemblies 168, 170 are locked in position (see FIG. 6), so too is the end effector 118 locked in position.

In order to change the vertical or medial-to-lateral position of the end effector 118, a user would depress the button 136. By depressing the button 136, the toothed receivers 146 are operative to further compress the spring 160 and disengage the toothed assemblies 168, 170. More specifically, the longitudinal pyramidal shapes 148 and corresponding longitudinal pyramidal cavities 150 no longer engage the teeth 178 of the toothed assemblies 168, 170, thereby allowing rotation of the toothed assemblies around the axle 164. By allowing free rotation of the toothed assemblies 168, 170 around the axle 164, the connection wires 188, 190 linking the end effector 118 and the toothed assemblies may be repositioned, which allows the end effector to be freely repositionable in the vertical direction (i.e., affecting pitch) and in the medial-to-lateral direction (i.e., affecting yaw). After the respective vertical and medial-to-lateral position of the end effector 118 has been reached, the user would discontinue depressing the button 136 to lock in the relative vertical and medial-to-lateral positions. In order to lock in the positions, the spring 160 forces the toothed receivers 146 upward and into engagement with the toothed assemblies 168, 170. Because the toothed assemblies 168, 170 include teeth 178 that engage the longitudinal pyramidal shapes 148 of the toothed receivers 146, the spring 160 will direct the toothed receivers upward and cause the toothed assemblies to possibly rotate slightly about the axle 164 so that the teeth are fully received within the longitudinal pyramidal cavities 150. If the position of the end effector 118 is such that the teeth 178 are aligned with the longitudinal pyramidal cavities 150, then the vertical and medial-to-lateral positions will be precisely maintained because of the tension on the connection wires 188, 190. But if the position of the end effector 118 is such that the teeth 178 are slightly misaligned with the longitudinal pyramidal cavities 150, then the vertical and medial-to-lateral positions will be changed as the toothed assemblies 168, 170 rotate slightly about the axle 164 so that the teeth are fully received within the longitudinal pyramidal cavities 150. After the teeth 178 are aligned and received within the longitudinal pyramidal cavities 150, the vertical and medial-to-lateral positions will be precisely maintained because of the tension on the connection wires 188, 190.

In order to maintain the orientation of the semi-rigid conduit (which carries the connection wires 188, 190) with respect to the housings 130, 132, a distal portion of the right side housing 130 includes a pair of detents 202 that engage the conduit 112. These detents 202 inhibit longitudinal movement of the conduit 112 with respect to the controller 110. Both detents 202 extend in parallel to one another and extend from an interior circumferential surface of the right side housing 130.

Figure 29:
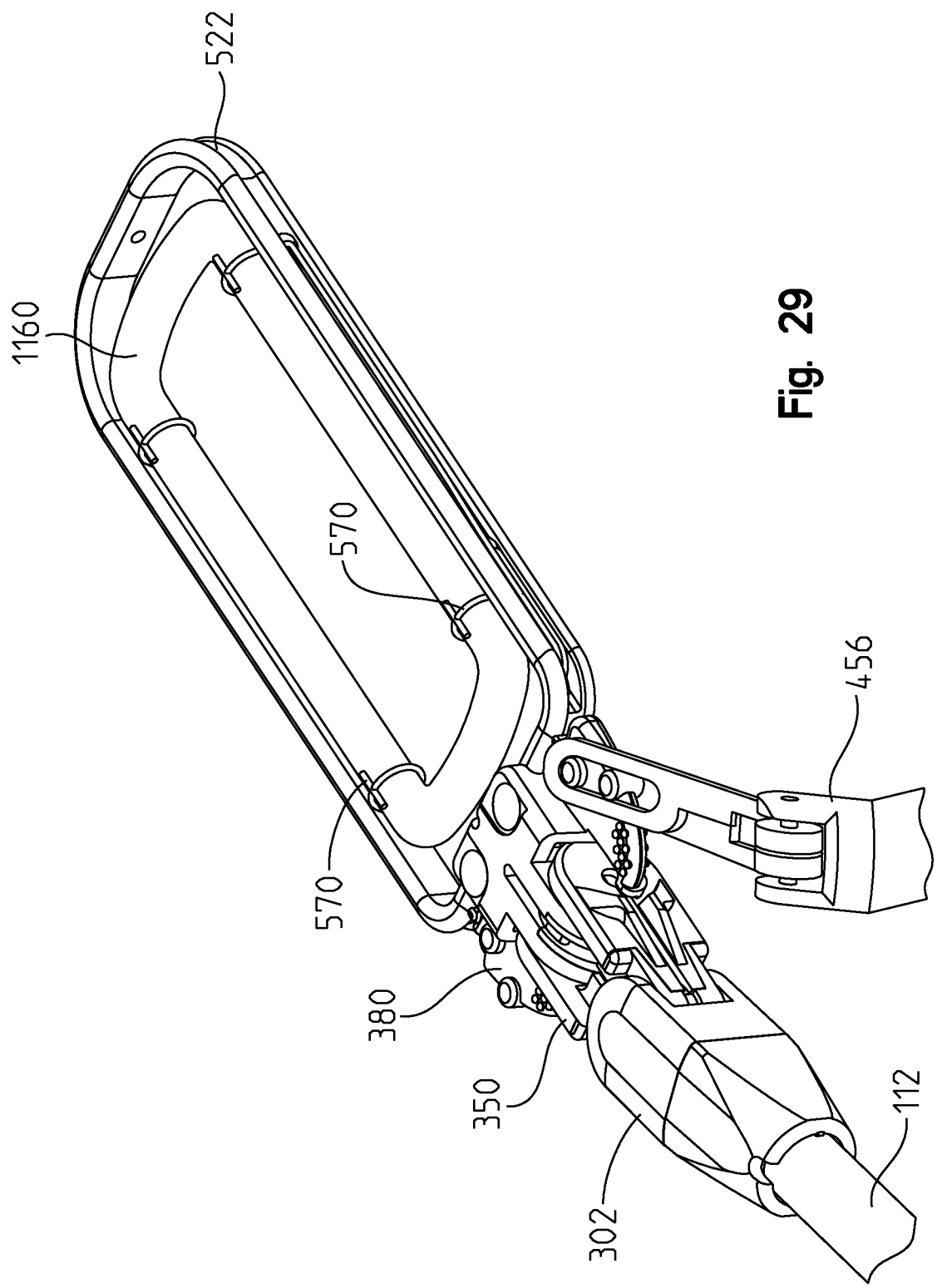
FIG. 29 is an elevated perspective view, from the proximal end, of the exemplary clevis, dual pivot joint, and yoke mounted to a clip deployment device and an occlusion clip, where the yoke is being grasped by a robotic grasper.
Figure 34:
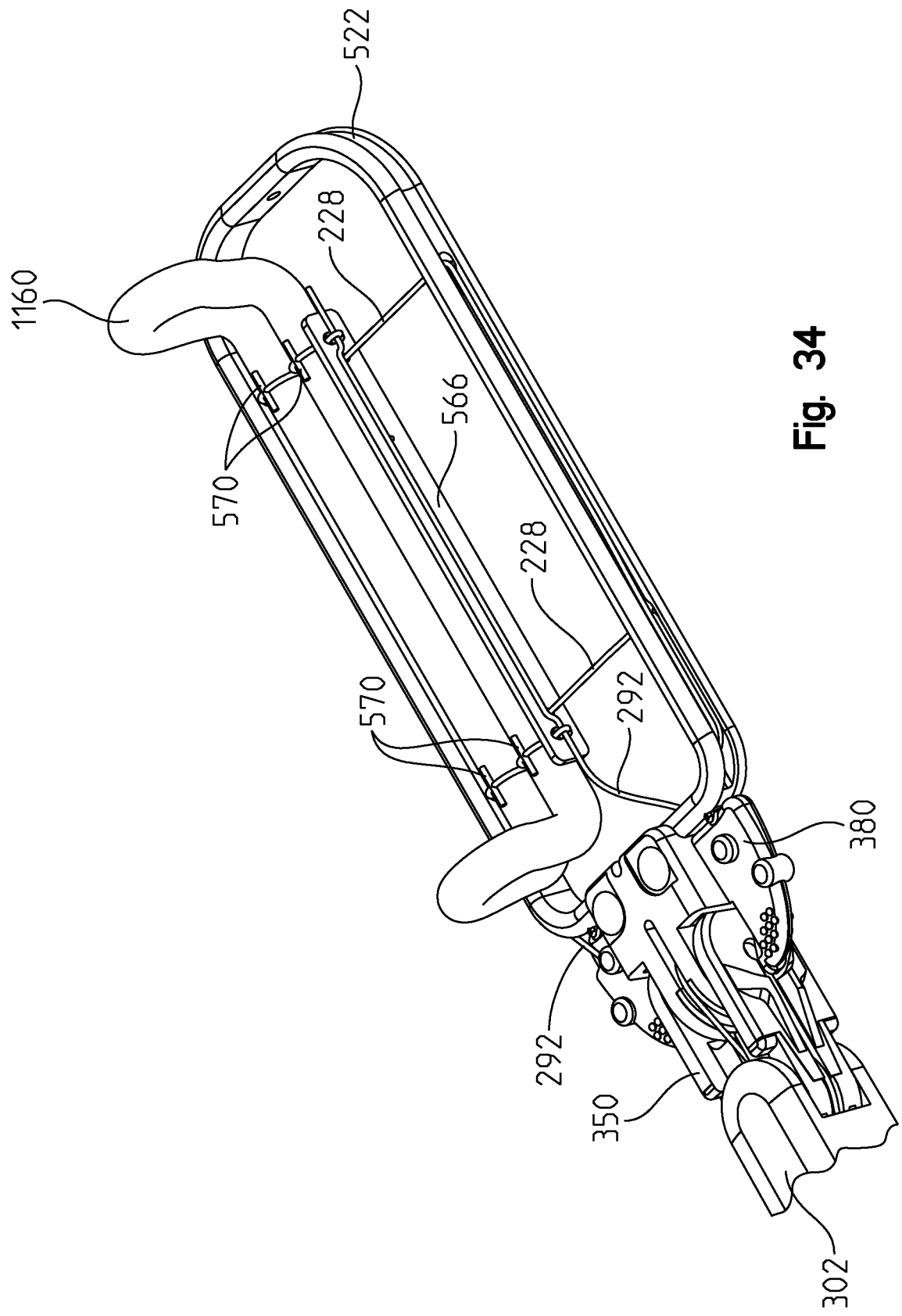
FIG. 34 is an elevated perspective view, from the proximal end and lateral side, of the exemplary clevis, dual pivot joint, and yoke mounted to a clip deployment device and an occlusion clip, where the draw wires, the clip release wires, and the suture loops are shown.
Figure 35:
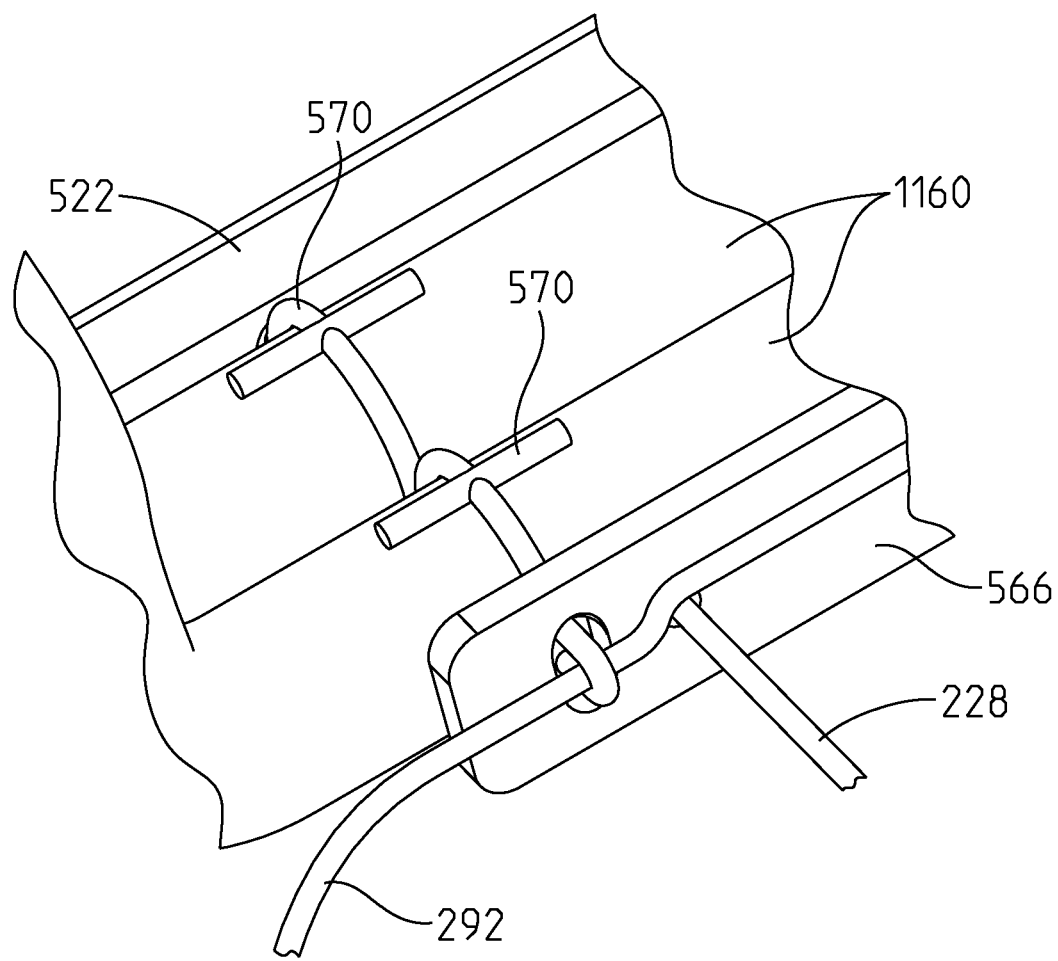
FIG. 35 is a magnified elevated perspective view showing the attachment between the occlusion clip and the clip deployment device, as well as the interaction of the draw wires and the clip release wires.

The right and left side housings 130, 132 cooperate to delineate a handle mechanism port 210 and a proximal port 212 open to the interiors of the respective housings. The handle mechanism port 210 accommodates throughput of a portion of a handle mechanism 218 that comprises a repositionable lever 220, a drive plate 222, a return spring 224, and a wire retainer 226. As will be discussed in more detail hereafter, the wire retainer 226 is concurrently coupled to draw wires 228 and the drive plate 222 so that movement of the lever 220 is operative to open and close an occlusion clip 1160 (compare FIGS. 29 and 34), such as during an atrial appendage occlusion clip deployment surgical procedure. A more detailed explanation of the respective components of the handle mechanism 218 follows.

The repositionable lever 220 includes an arcuate, ventral gripping surface that may include a series of convex bumps longitudinally spaced apart to facilitate gripping by a user. Opposite the ventral gripping surface is a corresponding interior surface from which a pair of spaced apart, parallel vertical walls 230, 232 extend. The vertical walls 230, 232 are also connected to one another via a plurality of cross walls 234. The vertical walls 230, 232 each include a distal upstanding loop 238 that provides a through opening in the medial-to-lateral direction to receive a axle 240 extending from the right side housing 130 around which the lever 220 rotates. Extending distally from the loop 238, the walls 230, 232 include a circular opening extending in the medial-to-lateral direction that receives a pin 244 in order to repositionably mount the drive plate 222 to the lever 220.

The exemplary drive plate 222 comprises an arcuate, flat plate sized to fit between the walls 230, 232 of the lever 220. A distal end of the plate 222 includes an opening to receive the pin 244. Extending proximally from the opening is an elongated, arcuate opening 246 adapted to receive a dowel 248 extending from the interior of the right side housing 130. In this manner, the dowel 248 is repositioned with respect to the opening 246 as the lever 220 repositions the drive plate 222. In exemplary form, the opening is partially defined by a lip 250 that acts to retain the dowel 248 in a static position after the lever 220 is fully closed. At the same time, the proximal end of the drive plate 222 includes an orifice 252 that receives a portion of the spring 224 in order to bias the lever 220 to the open position shown in FIG. 3. The opposing end of the spring 224 is mounted to a dowel 254 that extends from the interior of the right side housing 220.

The controller 110 also includes a removable stem 260 that is seated within the proximal port 212 of the housings 130, 132. The removable stem 260 is coupled to one or more clip release wires 292 (in this case, two clip release wires) that act to disconnect an occlusion clip from the clip deployment device 118. In this manner, the stem 260 may be removed from the proximal end of the controller 110, thereby drawing the release wire(s) proximally and disconnecting the occlusion clip from the clip deployment device 118. In this exemplary embodiment, the stem 260 is secured within the proximal port 212 via a friction fit that may be overcome by the user applying pressure to the stem to move it proximally with respect to the controller 110. But it is also within the scope of the disclosure to use detents or other affirmative release mechanisms to release the stem 260 from the controller 110.

The controller 110 is mounted to a rigid or semi-rigid conduit 112 that is relatively linear and has a relatively constant circular cross section. In this exemplary embodiment, the conduit 112 is fabricated from stainless steel and includes a proximal circular opening and a distal circular opening. The proximal circular opening provides access between the interior of the conduit 112 and the interior of the controller 110. More specifically, the hollow interior of the conduit 112 accommodates throughput of the connection wires 188, 190 and the clip release wires 292. The conduit 112 includes a proximal section having a pair of rectangular, arcuate cut-outs providing respective recesses for the detents 202 of the right side housing 130 to occupy and mount the conduit 112 to the housings 130, 132.

In addition, the conduit 112 may be relatively linear but include two additional orifices that accommodate a separate conduit (not shown) adapted to provide a separate avenue for an exploratory tool. Exemplary exploratory tools for use with the instant semi-rigid conduit include, without limitation, forceps, ablation rails, jaws, linear cutters, ablation pens, ablation clamps, illuminated dissectors, and non-illuminated dissectors. The exemplary exploratory tool may be used in combination with the end effector, which is manipulated by the repositionable mechanism.

Referring to FIGS. 11-14, a distal portion of the exemplary repositionable mechanism comprises a clevis 302 having a partially enclosed proximal section 304 that delineates a cavity 306 receives a distal section of the conduit 112 to mount the clevis to the conduit. On the interior of the cavity 306 are four equidistantly, radially spaced apart ribs 308 that extend longitudinally and in parallel to one another. The ribs 308 operate to decrease the diameter of the cavity 306 so that the ribs contact the exterior, circumferential surface of the conduit 112 to mount the conduit to the clevis 302 via a friction fit. Each of the ribs 308 terminates distally at a wall 310 extending normal to the longitudinal direction of the ribs. The wall 310 includes a series of orifices 312, 314, 316 that accommodate throughput of the connection wires 188, 190 and the clip release wires 292. In exemplary form, the first orifice 312 accommodates throughput of the first connection wire 188, while the second orifice 314 accommodates throughput of the clip release wires 292, while the third orifice 316 accommodates throughput of the second connection wire 190. The wall 310 also bridges the proximal section 304 and a distal section 320 of the clevis 302.

Te distal section 320 of the clevis 302 includes a pair of distal projections 324, 326 extending away from the wall 310 to create a ceiling and floor. The projections 324, 326 are oriented to provide a gap therebetween extending in proximal-to-distal direction and in a medial-to-lateral direction. Each projection 324, 326 includes a mildly convex outer surface 330 that is jointed by a peripheral surface 332 that is rounded to at the distal tip. The peripheral surfaces 332 are jointed by respective exterior side surfaces 334. Each projection 324, 326 includes a depression 336 that originates at the distal tip of the clevis 302 and extends proximally. The bounds of the depression 336 are delineated by a planar bottom surface 340, a horseshoe (i.e., semicircular) peripheral surface 342, and a planar base surface 344. The arcuate contour of the peripheral surface 342 is operative to allow a dual pivot joint to 350 to pivot in a single plane with respect to the clevis 302.

Referring to FIGS. 15-20, the dual pivot joint 350 comprises a proximal section 352 having a pair of plateaus 354 that extend in opposite directions from one another. Each plateau 354 includes a teardrop shaped circumferential surface 356 with the rounded portion of the surface adapted to have an arcuate curvature that approximates the arcuate curvature of the peripheral surface 342 of the clevis 302. The plateaus 354 are interposed by a platform 358 having opposed, generally planar parallel surfaces 360. Accordingly, the dual pivot joint 350 may pivot with respect to the clevis 302 by the plateaus 354 pivoting or rotating with respect to the peripheral surface 342, while the planar surfaces 360 contact the planar base surfaces 344 of the clevis to limit significant vertical play between the clevis and dual pivot joint. The pointed aspect of each circumferential surface 356 cooperates with the straight walls of the peripheral surface 342 of the clevis 302 to provide stops that limit the pivotal motion of the dual pivot joint 350 with respect to the clevis 302 to no more than fifty-five degrees from center (total range of motion of approximately 110 degrees). As will be understood by those skilled in the art, the range of travel may be increased by increasing the angle of the pointed aspect of the circumferential surfaces. Conversely, the range of travel may be decreased by decreasing the angle of the pointed aspect of the circumferential surfaces.

A proximal aspect of the platform 358 is rounded and includes two pair of arcuate walls 364 that are spaced apart from one another to create a gap 368 that tapers distally to create a cylindrical through hole 376 extending into the interior of a distal aspect 370 of the dual pivot joint. The tapered feature of each gap 368 is partially defined by a pair of angled faces 372 that operate to allow the connection wires 188 to be fed in between the walls 364, through the cylindrical hole 376 and into the interior of the distal aspect, where the wires are ultimately connected to a yoke 380. The tapered nature of each gap 368 ensures that the connection wires 188 do not become bound up by pivoting action of the dual pivot joint 350 with respect to the clevis 302. But for the tapered nature of the gap 368, pivoting action beyond center of the dual pivot joint 350 with respect to the clevis 302 would cause the path of the connection wires 188 to be lengthened, thereby resulting in pivoting of the yoke 380 with respect to the dual pivot joint.

Interposing the two pair of arcuate walls 364 and respective gaps 368 is a centered gap 384 that also tapers distally to create a through hole 386 having a rectangular, rounded cross-section that extends into the interior of the distal aspect 370 of the dual pivot joint. The tapered feature of this centered gap 384 is partially defined by a pair of angled faces 388 that operate to allow the draw wire 228 and clip release wires 292 to be fed in between the walls 364, through the hole 386, and into the interior of the distal aspect, where the wires are ultimately fed through a clip deployment frame 520. The tapered nature of this gap 384 ensures that the draw wire 228 and clip release wires 292 do not become bound up by pivoting action of the dual pivot joint 350 with respect to the clevis 302. But for the tapered nature of the gap 384, pivoting action beyond center of the dual pivot joint 350 with respect to the clevis 302 would cause the path of the draw wire 228 and clip release wires 292 to be lengthened, thereby potentially resulting in premature release of the clip 1160 and opening of the clip.

Adjoining the angled faces 388 is an arcuate wall 390 that curves around a lateral edge of the proximal section 352 and extends into the interior of the distal section 370. The arcuate wall 390 is inset within the proximal section 352 to create a lateral trench 392 on the right and left sides. Each lateral trench 392 ends distally proximate a lateral, longitudinal opening 396 extending through right and left side paddles 402. This pair of lateral trenches 390 respectively receives one of the connection wires 190 so that the ends of each connection wire extend into the interior of the distal section 370. Each end of the connection wire 190 is enlarged to prohibit the end from passing through the longitudinal opening 396. In other words, the longitudinal opening 396 is sized to allow throughput of the connection wire 190 along the longitudinal length of the connection wire, but is sized to prohibit throughput of the enlarged end of the connection wire. In this manner, tension can be applied the connection wires 190 in order to cause the dual pivot joint 350 to pivot with respect to the clevis 302. By applying tension to the right side connection wire 190, the dual pivot joint pivots to the right side. Conversely, by applying tension to the left side connection wire 190, the dual pivot joint pivots to the left side.

The right side paddle 402 is a mirror image of the left side paddle. Accordingly, for purposes of explanation, only a single paddle will be described. Each paddle 402 includes a lateral exterior surface 406 that is substantially planar but for a pair of projections 408 that are spaced apart from one another by the longitudinal opening 396 extending therebetween. Each projection 408 includes a linear aspect 410 that extends in parallel with the longitudinal opening 396 and a curved aspect 412. As will be discussed in more detail hereafter, the curved aspect 412 has a curvature that mirrors the arcuate motion of the yoke 380. The paddle 402 includes a vertical height extending above and below the proximal section 352. The top and bottom surfaces 414 of the paddle 402 are generally planar and are bridged by a curved circumferential surface 418. The lateral or widthwise dimension of the paddle 402 is substantially uniform, from proximal to distal, but for an interior depression 420 that is open on the distal end of the paddle and extends proximally to intersect the longitudinal opening 396. The depression 420 is partially defined by a planar wall 424 that is perpendicular to a second planar wall 426 with an arcuate transition therebetween. At the same time, a third wall 428 is also perpendicular to the planar wall 424 and includes an arcuate profile that corresponds to the arcuate profile of a plateau of the yoke 380. An interior planar wall 430 of each paddle 402 intersects a pair of rectangular projections 432. Each rectangular projection 432 includes a distal wall 436 that is arcuate from right to left. The arcuate curvature of the distal wall generally tracks the arcuate profile of a portion of the yoke 380.

Referring to FIGS. 21-26, the yoke 380 comprises a hollow box having a roof 440, a floor, 442, a right side wall 444, and a left side wall 446. The front of the box is open and reveals the interior cavity. Extending laterally outward from the right and left side walls 444, 446 are respective right and left wings 448, 450.

Each wing 448, 450 includes a pair of circumferential projections 452 that extend vertically therethrough to protrude above and below the wing. In this exemplary embodiment, the projections are sized and spaced apart to facilitate grasping of the yoke 380 by a robotic grasper 456 (see FIG. 29). A distal portion of the each wing 448, 450 is generally flush with walls defining a distal recess 458 within the respective right and right and left side walls 444, 446. As will be discussed in more detail hereafter, the distal recess is sized to accommodate partial insertion of the clip deployment frame 520.

The right wing 448 is laterally widest at its distal end and tapers in a widthwise dimension, bounded by an arcuate peripheral surface 460. The proximal portion of the right wing 448 extends proximally beyond the hollow box and includes a planar guide 464 that is parallel to a right side plateau 466 extending from a proximal section 468 of the yoke 380. A hole 470 extends through the planar guide 464 and extends into communication with an underneath trench 472 formed into the bottom surface 474 of the right wing. This underneath trench 472 terminates distally at the distal end of the right wing 448. In particular, one of the clip deployment wires 292 is fed past the proximal section 468, through the hole 470, and along this underneath trench 472 to exit and extend distally from the trench.

The proximal section 468 includes right and left side plateaus 466, 476 that extend in opposite directions from one another. Each plateau 466, 476 includes a teardrop shaped circumferential surface 478 with the rounded portion of the surface adapted to have an arcuate curvature that approximates the arcuate curvature of the third wall 428 of the dual pivot joint 350. The plateaus 466, 476 are interposed by a platform. 482 having opposed, generally planar parallel surfaces 484. Accordingly, the yoke 380 may pivot with respect to the dual pivot joint 350 by the plateaus 466, 476 pivoting or rotating with respect to the third wall 428. The pointed aspect of each circumferential surface 478 cooperates with the straight walls of the second planar wall 426 of the dual pivot joint 350 to provide stops that limit the pivotal motion of the dual pivot joint with respect to the yoke to no more than fifty-five degrees from center (total range of motion of approximately 110 degrees). As will be understood by those skilled in the art, the range of travel may be increased by increasing the angle of the pointed aspect of the circumferential surfaces. Conversely, the range of travel may be decreased by decreasing the angle of the pointed aspect of the circumferential surfaces.

Figure 30:
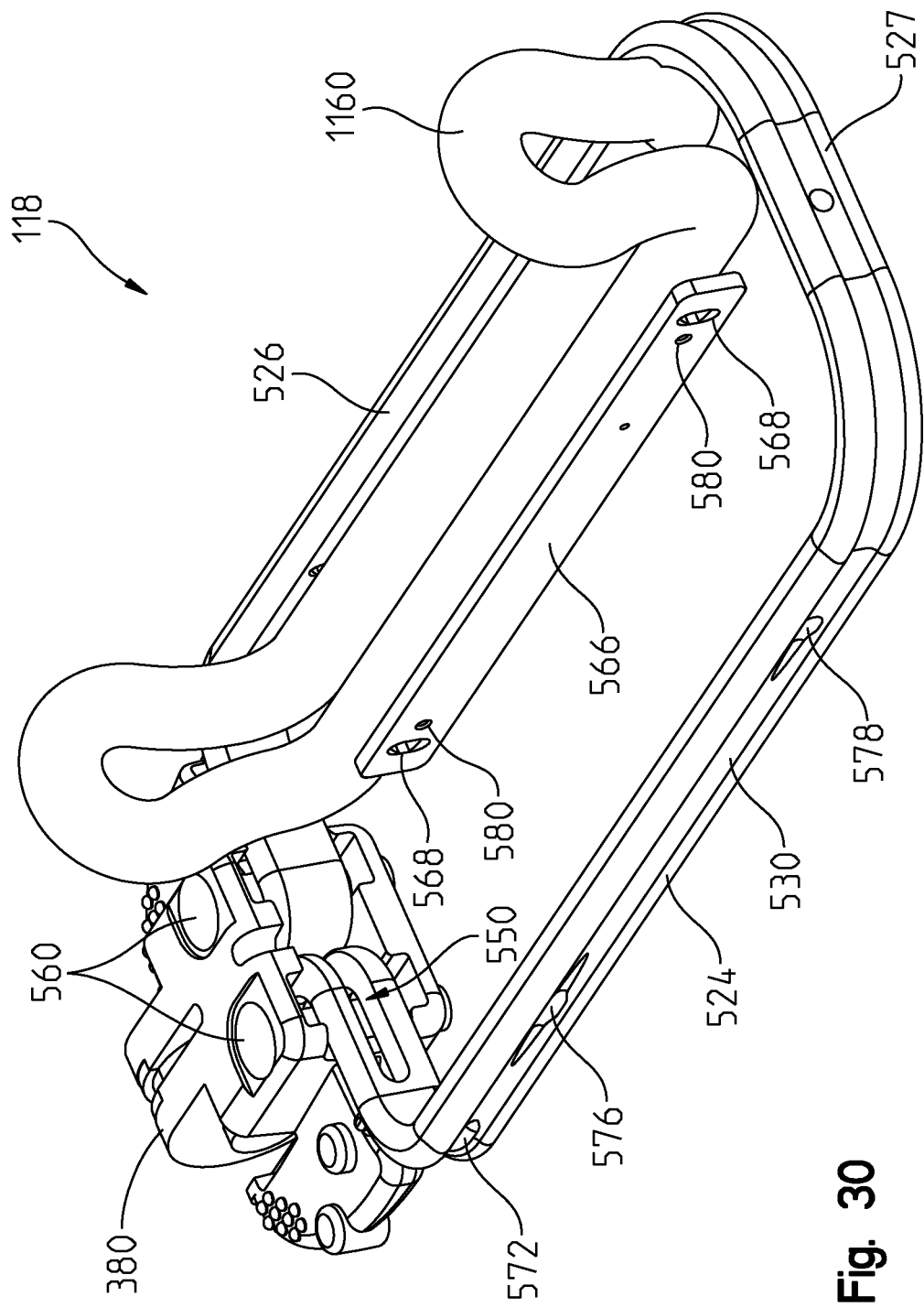
FIG. 30 is an elevated perspective view, from the distal end, of the exemplary yoke mounted to a clip deployment device, where the view is devoid of the draw wires and the clip release wires.
Figure 31:
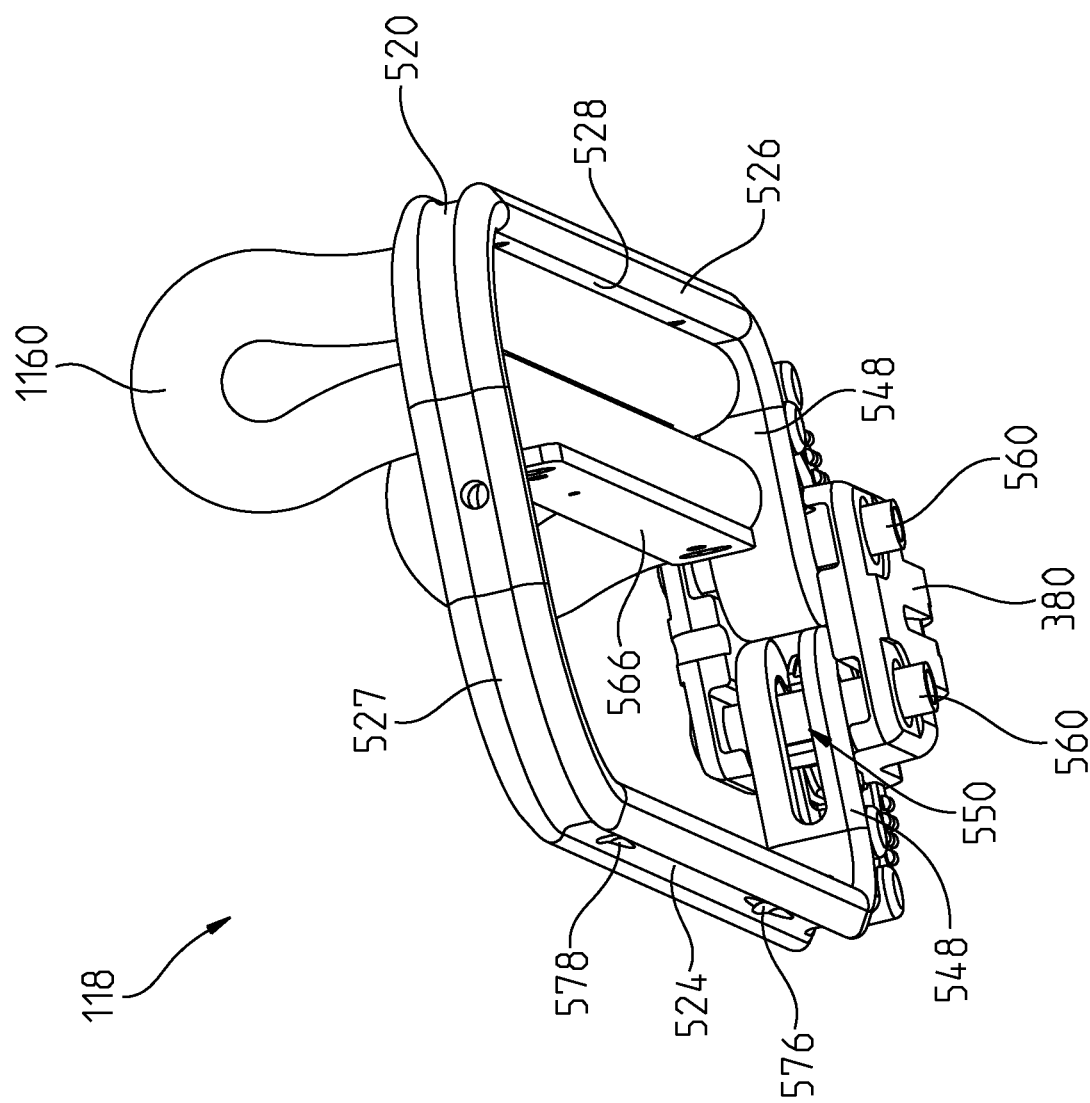
FIG. 31 is an underneath perspective view, from the distal end, of the exemplary yoke mounted to a clip deployment device, where the view is devoid of the draw wires and the clip release wires.
Figure 32:
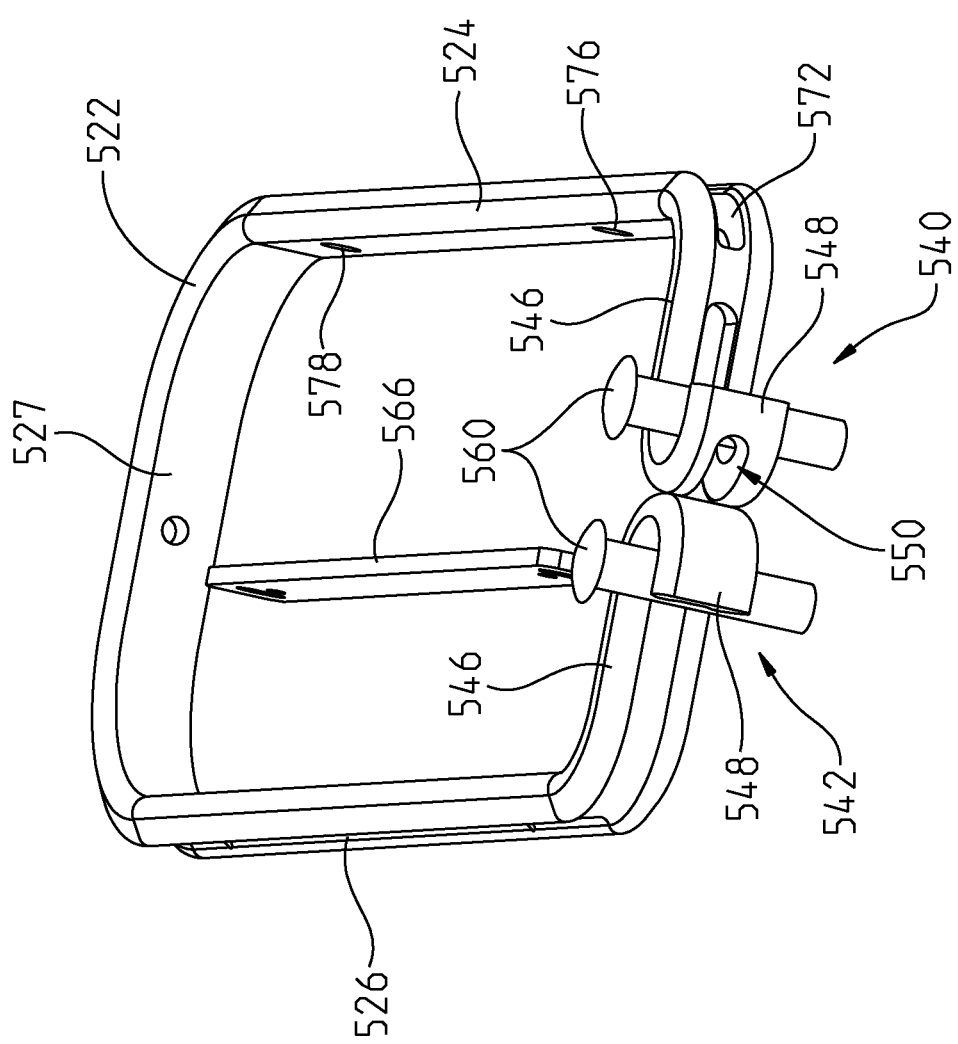
FIG. 32 is an elevated perspective view, from the proximal end, of the exemplary clip deployment device and retention dowels, where the view is devoid of the draw wires and the clip release wires.
Figure 33:
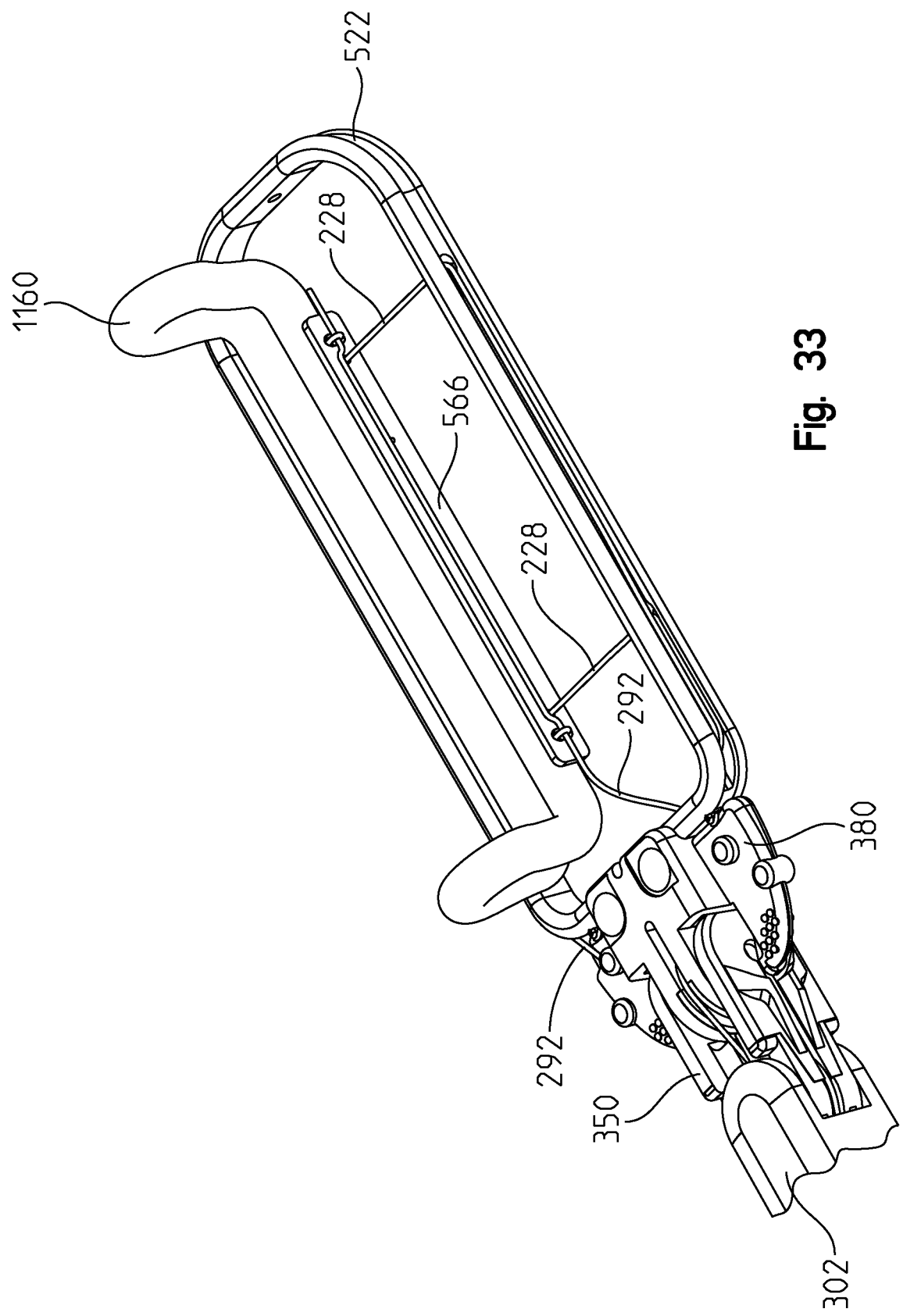
FIG. 33 is an elevated perspective view, from the proximal end and lateral side, of the exemplary clevis, dual pivot joint, and yoke mounted to a clip deployment device and an occlusion clip, where the draw wires and the clip release wires are shown.

A proximal aspect of the platform 482 is rounded and includes two pair of arcuate, solid walls 486 that are spaced apart from one another to create a gap 488 that tapers distally to create a through hole 490 extending into the interior of the hollow box. The tapered feature of this gap 488 is partially defined by a pair of angled faces that operate to allow the draw wires 228 to be fed in between the walls 486, through the hole 490 and fed through the clip deployment frame 520, where the wires are ultimately connected to an occlusion clip 1160 (see FIG. 30). The tapered nature of this gap 488 ensures that the draw wires 228 do not become bound up by pivoting action of the yoke 380 with respect to the dual pivot joint 350. But for the tapered nature of the gap 488, pivoting action beyond center of the yoke 380 with respect to the dual pivot joint 350 would cause the path of the draw wires 228 to be lengthened, thereby resulting in potentially premature opening of the occlusion clip 1160.

Interposing the solid walls 486 and inset therein are top and bottom arcuate walls 492, 494. The arcuate nature of these walls 492, 494, teamed with being inset in between the solid walls 486 creates a groove that feeds respective top and bottom holes 498, 500 that are open to the interior of the hollow box. In exemplary form, each connection wire 188 is received within the respective grooves so that the distal ends of the connection wires extend into the interior of the hollow box. Each end of the connection wires 188 is enlarged to prohibit the end from passing through the top and bottom holes 498, 500. In other words, the holes 498, 500 are sized to allow throughput of the connection wires 188, but are sized to prohibit throughput of the enlarged end of the connection wires. In this manner, tension can be applied the connection wires 188 in order to cause the yoke 380 to pivot with respect to the dual pivot joint 350. By applying tension to the top side connection wire 188, the yoke pivots upward with respect to the dual pivot joint 350. Conversely, by applying tension to the bottom connection wire 188, the yoke pivots downward with respect to the dual pivot joint 350.

Adjacent the platform 482, on the left side, is the left wing 450. The left wing 450 is laterally widest at its distal end and tapers in a widthwise dimension, bounded by an arcuate peripheral surface 504. The proximal portion of the left wing 450 extends proximally beyond the hollow box and includes a planar guide 506 that is parallel to the left side plateau 476. A hole 508 extends through the planar guide 506 and extends into communication with an underneath trench 510 formed into the bottom surface 512 of the left wing. This underneath trench 510 terminates prior to reaching the distal end of the left wing 450. In particular, the trench 510 terminates and feeds into a distal tunnel 514 that extends through a distal portion of the left wing 450. In this exemplary embodiment, a second of the clip deployment wires 292 is fed past the proximal section 468, through the hole 508, along this underneath trench 510, through the tunnel 514 and exits distally from the tunnel.

Referring to FIGS. 27-35, the clip deployment device 118 is partially received within the interior of the hollow box. In exemplary form, the clip deployment device 118 includes a rectangular frame 520 having parallel longitudinal sides 524, 526 that are connected to one another via a distal cross-member 527 with rounded corners therebetween. In this exemplary embodiment, each parallel side 524, 526 includes a substantially planar interior wall 528 and a concave exterior wall 530, opposite the interior wall. The concave nature of the exterior wall 530 creates a longitudinal channel, with one exterior channel receiving a first of the clip deployment wires 292. In addition, the parallel sides 524, 526 may include one or more through orifices extending through the interior and exterior walls 528, 530.

The proximal end of the rectangular frame 522 includes a pair of rounded corners that extend from the parallel sides 524, 526. Each rounded corner on the proximal end forms part of an S-shaped retainer 540, 542 that is partially received within the hollow box interior of the yoke 380. More specifically, both S-shaped retainers 540, 542 comprise a first rounded corner that transitions into a straight segment 546, which transitions into a semicircular segment 548. The S-shaped retainers 540, 542 are mirror images of one another, except that the one retainer 540 includes an orifice 550 that extends through the interior and exterior surfaces and along the majority of the straight and semicircular segments 546, 548.

In order to secure the clip deployment device 118 to the yoke 380, two dowels 560 are inserted through corresponding holes 562 in the top and bottom surfaces 440, 442 of the yoke. The holes 562 are sized to retain the dowels 560 in position. But before the dowels 560 are inserted into the holes 562, the S-shaped retainers 540, 542 are inserted into the interior of the yoke 380. In exemplary form, the vertical dimension of the S-shaped retainers 540, 542 is such that the retainers are wedged in between the top and bottom walls 440, 442 of the yoke 380. Moreover, the collective lengthwise dimension of the S-shaped retainers 540, 542 is such that the retainers are wedged in between the right and left side walls 444, 446. In this manner, even absent the dowels 560, there is not significant play between the clip deployment device 118 to the yoke 380 in the vertical and lateral directions. In order to reduce play in the proximal-to-distal direction, the dowels 560 are inserted through the holes 562 after the semicircular segment 548 of each S-shaped retainers 540, 542 is positioned to partially outline an imaginary cylinder extending through the holes. This locks the S-shaped retainers 540, 542 in position with respect to the yoke 380, thereby mounting the clip deployment device 118 to the yoke.

The orifice 550 of the one retainer 540 provides an egress hole through which a second of the clip deployment wires 292 passes through. The second of the clip deployment wires 292 extends into the interior of the rectangular frame 522 and passes longitudinally along the exterior of an elongated deployment plate 566. The deployment plate 566 includes a pair of orifices 568 near the proximal and distal ends of the plate. As will be discussed in more detail hereafter, the orifices 568 receive suture loops 570 that are captured by the clip deployment wire 292 passing therethrough.

The orifice 550 also provides an egress hole through which the draw wires 228 pass through. The draw wires 228 are initially routed into the interior of the rectangular frame 522 to pass through an orifice 572 in one of the proximal rounded corners. Both wires 228 extend along the longitudinal channel of one of the parallel sides 524 created by the concave exterior wall 530. One of the wires passes through a first proximal orifice 576 in the first parallel side 524, while the second wire continues to extend along the longitudinal channel until reaching a second distal orifice 578. Both wires 228 then extend into the interior of the rectangular frame 522 and pass perpendicularly through a second set of orifices 580 of the elongated deployment plate 566. This second set of orifices 580 are inset with respect to the pair of orifices 568 near the proximal and distal ends of the plate. The wires are joined and create a closed loop coupled to the deployment plate 566.

Figure 36:
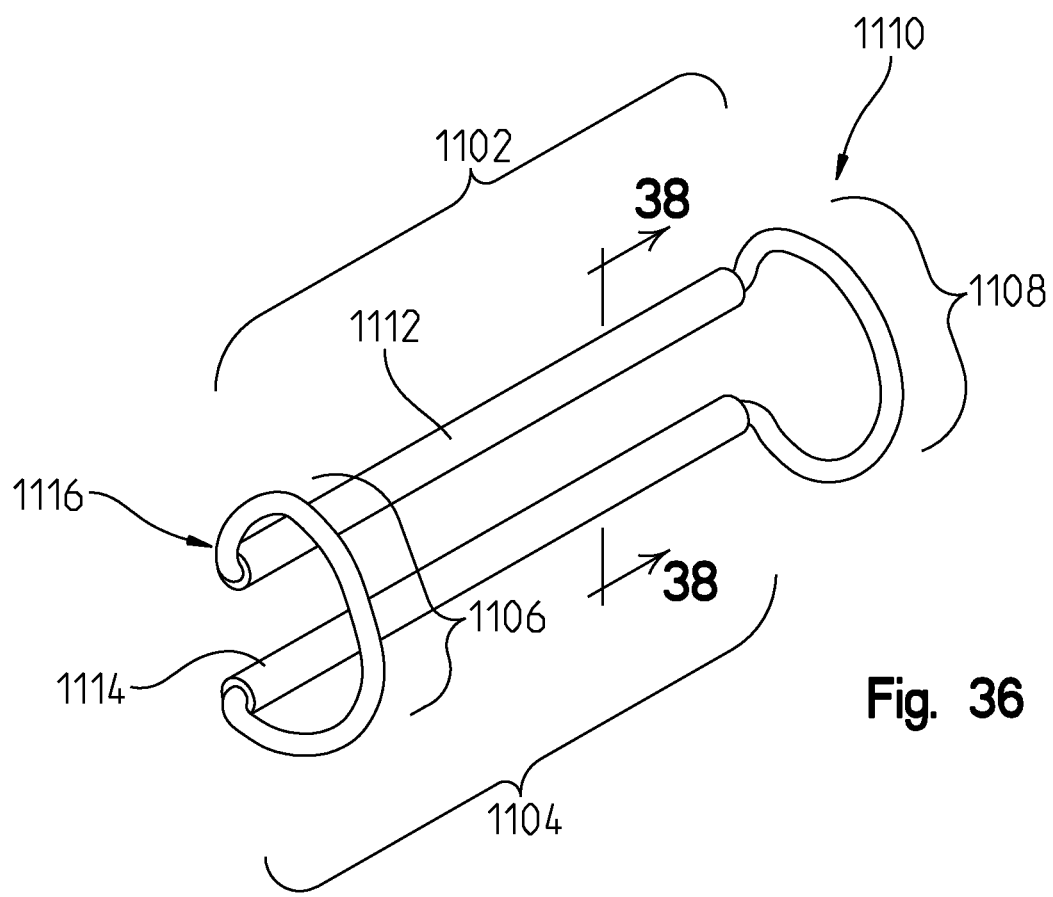
FIG. 36 is a perspective view of an exemplary clamp in an open position that may be used with the exemplary laparoscopic device of FIG. 1.
Figure 37:
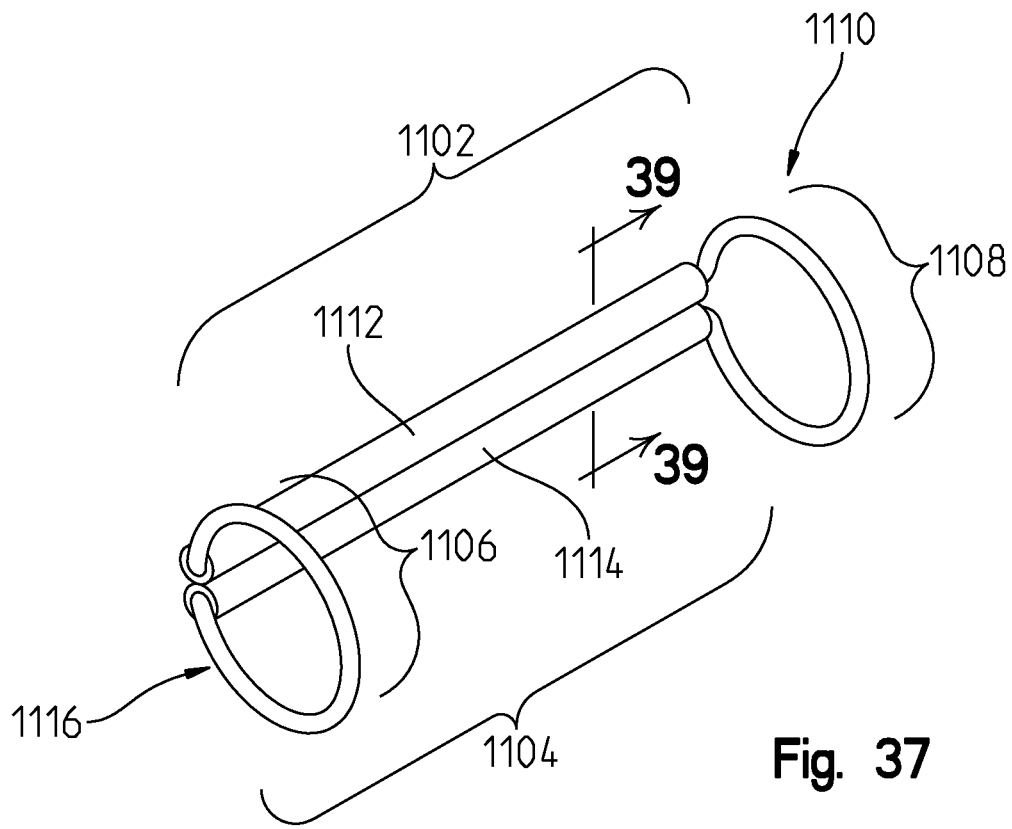
FIG. 37 is a perspective view of the exemplary clamp of FIG. 36 in a closed position.
Figure 38:
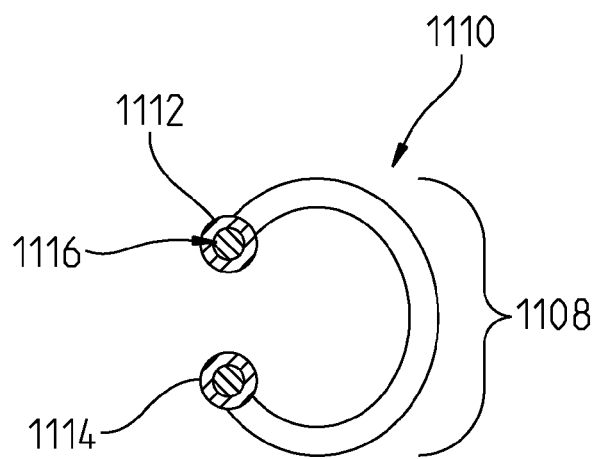
FIG. 38 is a cross-sectional view of the exemplary clamp of FIG. 36 in its open configuration, showing the wire member, rigid tubular members, and the urging members.

Referring to FIGS. 36-38 show one embodiment of a left atrial appendage occlusion clamp 1110 in an open position with spaced apart rigid clamping portions 1102, 1104 and resilient or elastic urging members 1106, 1108 at opposite ends of each clamping portion 1102, 1104. Clamping portions 1102, 1104 may be tubular, and both clamping portions 1102, 1104 may be at least substantially parallel to each other when arrest, i.e., when they are not being used to clamp tissue. Clamping portions 1102, 1104 may also be of substantially equal length or of different length, and each may be of larger outer diameter than the wire that may be used to form each of the urging members 1106, 1108. In this regard, the wire forming urging members 1106, 1108 can extend through the hollow interiors of the clamping portions 1102, 1104. In this illustrative example, the urging members 1106, 1108 are each shaped as a loop. The planes defined by the looped configuration of each of the urging members 1106, 1108 may be substantially parallel to each other and, in turn, substantially perpendicular to each of the clamping portions 1102, 1104. Of course, other angular orientations are possible as well.

Figure 39:
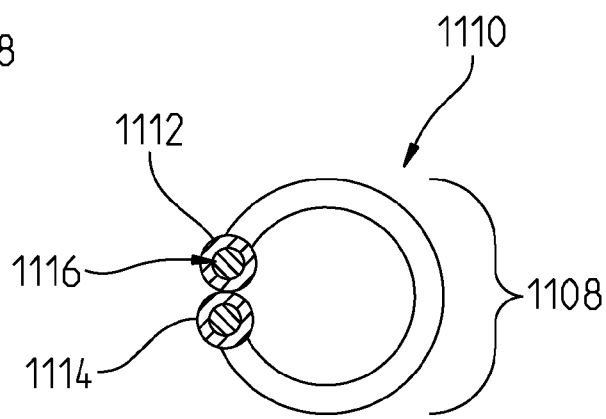
FIG. 39 is a cross-sectional view of the exemplary clamp of FIG. 37 in its closed configuration, showing the wire member, rigid tubular members, and the urging members.
Figure 40:
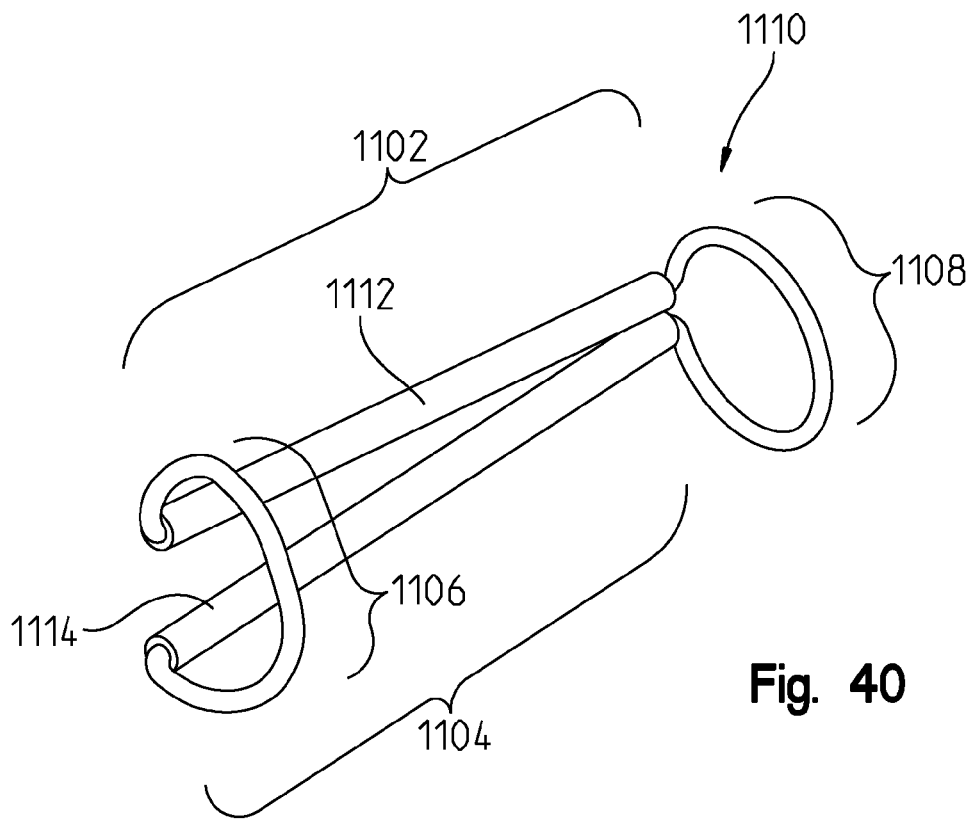
FIG. 40 is a perspective view of the exemplary clamps of FIGS. 36-39 and showing the ability to close in a non-parallel fashion.
Figure 41:
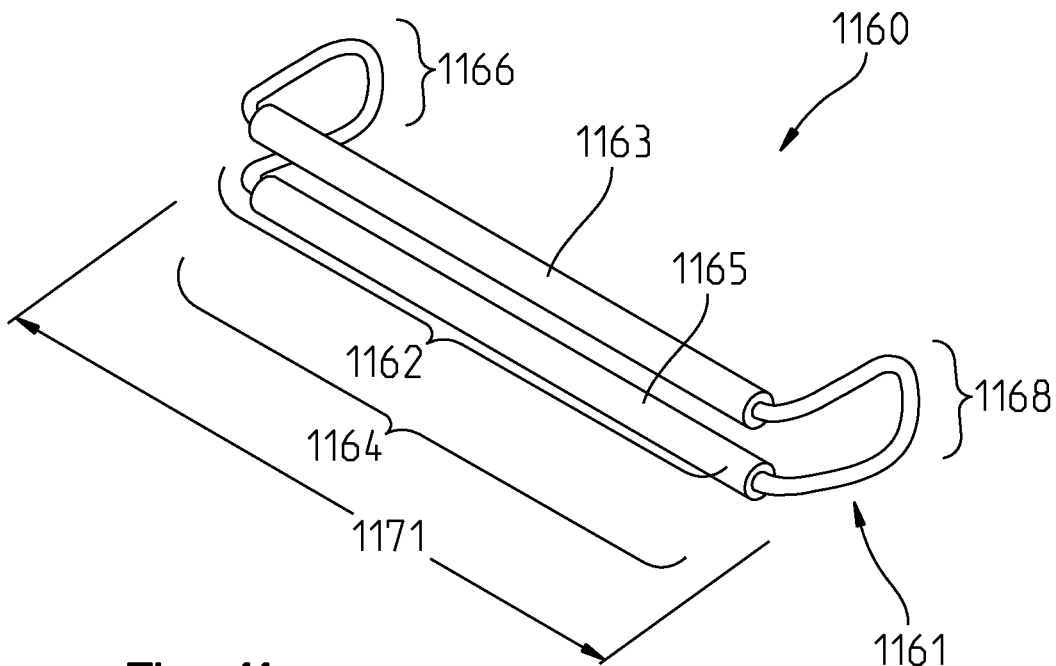
FIG. 41 is a perspective view of the first stage of assembly of an alternate embodiment of a clamp, showing a wire member surrounded by rigid tubular members.
Figure 42:
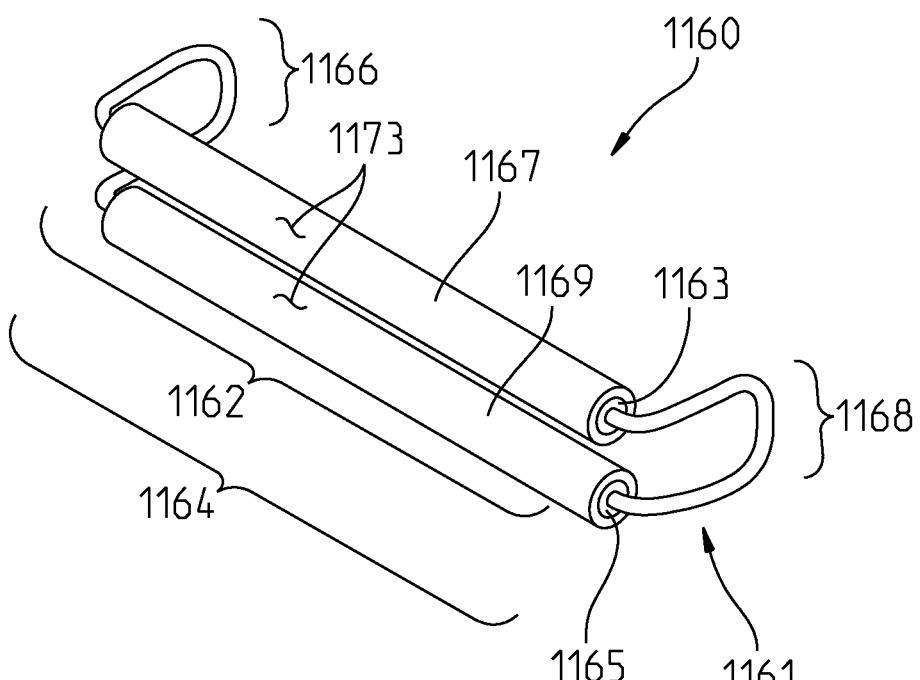
FIG. 42 is a perspective view of the second stage of assembly of the clamp of FIG. 41, in which platens have been added over the rigid tubular members.

FIGS. 37-39 show the same clamp 1110 of FIGS. 36-38 with the clamping portions 1102, 1104 in their normally biased together positions. Contact between the clamping portions 1102, 1104 may occur initially along their entire parallel lengths as shown. Of course, when clamping portions 1102, 1104 are covered in fabric or other material as later described, contact may occur between the fabric or other material instead. In FIGS. 36-39, only the structure and relative positions of the rigid members 1102, 1104 and urging members 1106, 1108 are shown. The final assembly is depicted in FIGS. 40-42 which, although describing a slightly different embodiment, show the general steps in the construction of each embodiment. The clamping portions 1102, 1104 may be made from rigid tubes 1112, 1114 of a rigid metal such as titanium disposed over a wire member 1116. In this embodiment, titanium is used for its compatibility with MRI imaging, its biocompatibility and its galvanic compatibility with the wire member 1116 when the wire member 1116 is formed from superelastic materials such as a nickel titanium alloy. This embodiment and the other embodiments disclosed herein may use a superelastic material such as a nickel titanium alloy to form the urging members 1106, 1108. Superelastic properties will allow the material to be greatly extended to open the clamping portions 1106, 1108 of the clamp 1110 without permanently deforming the material. These superelastic materials can also be compatible with MRI imaging and easily tolerated as an implant material in the body. The rigid tubular members 1112, 1114 of this embodiment are mechanically fastened to the underlying wire member 1116 preferably by mechanically swaging the titanium tubes 1112, 1114 to the wire members 1116. Although a single, continuous wire member is shown directed through both clamping portions 1102, 1104 and urging members 1106, 1108, the clamp 1110 of this embodiment may also be made with two or more wires, or with any other suitable components.

As shown in FIG. 40, in addition to being able to close on tissue or anatomical structure in a parallel fashion, the clamp 1110 can also apply force to the anatomical structure in a nonparallel clamping fashion. This allows the clamp 1110 to accommodate non-uniform tissue thickness over the length of the clamping portions 1102, 1104. In addition, with separate urging members 1106, 1108 at opposite ends of the clamping portions 1102, 1104 the nonparallel clamping can originate from either side of the clamp 1110. The non-parallel clamping feature of this embodiment allows the clamp 1110 to accommodate a wide range of hollow anatomical structures with varying wall thicknesses throughout its length and breadth. For example, some anatomical structures such as atrial appendages of the heart have internal structures called trabeculae, which are non-uniform and very often cause variable thicknesses across one or more of their dimensions. Nonuniform clamping, therefore, can be advantageous in this application for this reason or for other reasons.

FIG. 41 shows an alternate embodiment of a clamp 1160 including two urging members 1166, 1168 shaped to resemble a letter "U" instead of the more circular loop configuration of the embodiment of FIGS. 36-39. As is the case with the first clamp 1110, the U-shaped urging members 1166, 1168 of clamp 1160 may also lie in planes generally parallel to each other and perpendicular to the axes of the clamping portions 1162, 1164. A potential use of the embodiment of FIG. 41 may lie in the lesser force exerted by U-shape urging members 1166, 1168 on the clamping portions 1162, 1164 with respect to the force exerted by the loop-shape urging members 1106, 1108 of clamp 1110 in FIGS. 36-39, making it more suitable for clamping of anatomical structures not requiring a relatively high clamping force. The U-shape configuration of the urging members 1166, 1168 generally requires less space in the direction perpendicular to the axes of the clamping portions 1162, 1164. FIG. 41 shows a first stage of assembly of the clamp 1160, where the rigid tubular members 1163, 1165 are joined with the superelastic wire member 1161. In this embodiment, mechanical swaging is used to join the tubular members 1163, 1165 to the wire 1161. However, adhesives or laser welding or other methods of attachment could be easily used instead. Similarly, it will be appreciated that rigid tubular members 1163, 1165 may not necessarily need to be bonded to wire member 1161 at all. One may rely, for example, on designing the rigid tubular members 1163, 1165 so that their inside diameters simply closely fit over the wire 1161. In addition, the rigid tubular members 1163, 1165 could take on many different cross sectional shapes. Cross-sectional shapes such as ovals, triangles or rectangles with rounded edges could be preferable and may eliminate the addition of the load spreading platens 1167, 1169 shown in FIG. 42, as these alternate shapes may provide a larger area of contact against the anatomical structure to be engaged by the clamp 1150. Since different anatomical structures greatly vary from subject to subject, it is advantageous to have a manufacturing method in which the length 1171 of the clamp 1160 can be easily varied. By cutting rigid members 1163, 1165 to various different lengths, different size assemblies can be configured.

FIG. 42 shows the next step in the assembly of the clamp. Load spreading platens 1167, 1169 made of plastic or other biocompatible material such as urethane, may be slipped over the titanium or other suitable material tubing that forms rigid tubular members 1163, 1165, to provide a resilient surface 1173 to spread the load out onto a larger surface area, thereby preventing point source loading of the tissue which might otherwise result in cutting of the tissue before it has had a chance to become internally fused. The platens 1167, 1169 can be assembled and applied over the rigid tubular members 1163, 1165 prior to the swaging step or platens 1167, 1169 can alternatively be manufactured in such a way so as to have a longitudinal split which allows the material to be opened and forced onto the rigid tubular members 1163, 1165.

Figure 43:
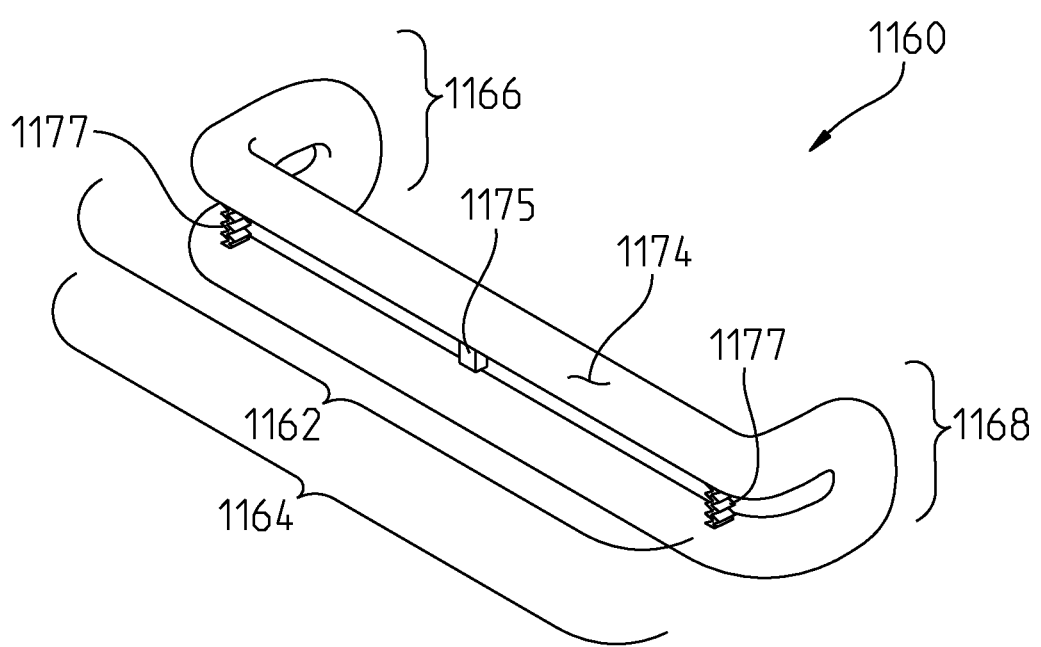
FIG. 43 is a perspective view of the claim of FIGS. 41 and 42, once an outer fabric covering has been disposed over the entire surface of the clamp.

FIG. 43 shows the clamp 1160 after a fabric cover material 1174 made of material such as polyester has been sewn around the clamping portions 1162, 1164 and urging members 1166, 1168. It will be appreciated that this material or any other similar materials may be used as a full or partial covering in any of the disclosed embodiments. Such a material is preferably suitable to engage the tissue of the anatomical structure being clamped as well as that of surrounding areas. Preferably, the material 1174 is circular warp knit fabric tube, with a diameter of approximately 4 to 5 mm and made from a combination of 4/100, 2/100 and 1/100 textured polyester. The material 1174 may also be heat-treated to cause a velour effect. The fabric or other material 1174 is furthermore sewn or otherwise applied over the urging members 1166, 1168. In addition, fabric pieces 1177 may be attached at opposite respective ends of clamping portions 1162, 1164 to prevent any part of the engaged anatomical structure from escaping the annular occlusion area between the clamping portions 1162, 1164. In other words, fabric pieces 1177 act as tissue blocking members or dams at opposite ends of the clamp. This or another tissue blocking feature may also be implemented into any other embodiment. This is desirable as it minimizes the probability of unintentionally leaving any part of the engaged anatomical structure unclamped. The material 1177, like material 1174, can also promote tissue in-growth.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A surgical device comprising:
   a housing operatively coupled to a first control and a second control;
   an end effector operatively coupled to the first control, the end effector comprising a first component and a second component selectively repositionable with respect to one another within an X-Y plane, the end effector also including a third component selectively repositionable with respect to the second component within an Y-Z plane;
   an occlusion clip deployment device operatively coupled to the end effector and the second control;
   a third control operatively coupled to the housing, wherein the third control is operatively coupled to a first connection line operatively coupled to the occlusion clip deployment device so that movement of the third control is operative to reposition at least a portion of the first connection line with respect to the occlusion clip deployment device; and
   a conduit extending between the housing and the end effector;
   wherein:
   the first control includes a first passive constraint and a second passive constraint;

the first passive constraint in an unlocked position allows free motion between the first component and the second component within the X-Y plane;
the first passive constraint in a locked position retards free motion between the first component and the second component within the X-Y plane;
the second passive constraint in an unlocked position allows free motion between the second component and the third component within the Y-Z plane; and,
the second passive constraint in a locked position retards free motion between the second component and the third component within the Y-Z plane;
the third control includes a plug detachable from the housing;
the plug is repositionable from an attached position coupled to the housing to a detached position decoupled from the housing; and,
repositioning the plug from the attached position to the detached position causes more of the first connection line to be drawn into the housing and further away from the occlusion clip deployment device.

2. The surgical device of claim 1, further comprising an occlusion clip operatively coupled to the clip deployment device using the first connection line.

3. The surgical device of claim 1, wherein the end effector includes a robotic grasping feature to facilitate grasping and repositioning of the end effector by a robotic grasper.

4. The surgical device of claim 1, wherein:
the first passive constraint includes at least one connection wire in tension that is operatively coupled to the second component and to the housing; and,
the second passive constraint includes at least one connection wire in tension that is operatively coupled to the third component and to the housing.

5. The surgical device of claim 1, wherein:
the first passive constraint includes a repositionable button selectively coupled to a first reel, where the button is repositionable between a locked and an unlocked position, where the locked position retards rotation of the first reel, and where the unlocked position allows rotation of the first reel;
the first reel is operatively coupled to a first connection line operatively coupled to the first component;
the second passive constraint includes the repositionable button selectively coupled to a second reel, where the locked position retards rotation of the second reel, and where the unlocked position allows rotation of the second reel;
the second reel is operatively coupled to a second connection line operatively coupled to the second component; and,
the first reel is independently repositionable with respect to the second reel.

6. The surgical device of claim 1, wherein:
the second control includes a lever operatively coupled and selectively repositionable with respect to the housing, the lever being operatively coupled to a first connection line operatively coupled to the occlusion clip deployment device so that movement of the lever is operative to reposition at least a portion of the occlusion clip deployment device;
the lever is repositionable between a locked and an unlocked position;
the unlocked position allows the lever to be repositioned; and,
the locked position retards the lever from being repositioned.

7. A surgical device comprising:
a housing operatively coupled to a first control;
an end effector operatively coupled to the first control, the end effector comprising a clevis selectively repositionable with respect to a dual pivot joint within an X-Y plane, the dual pivot joint selectively repositionable with respect to a yoke within an Y-Z plane;
a surgical conduit extending between the housing and the end effector; and,
a deployment control operatively coupled to the housing, the deployment control including a deployment line extending along the conduit and concurrently mounted to a deployment plug removably fastened to the housing;
wherein:
the first control includes a first line and a second line extending along the conduit concurrently coupled to the dual pivot joint, the first line impacting movement of the dual pivot joint with respect to the clevis in a first direction within the X-Y plane, the second line impacting movement of the dual pivot joint with respect to the clevis in a second direction, generally opposite the first direction, within the X-Y plane; and,
the first control includes a third line and a fourth line extending along the conduit concurrently coupled to the yoke, the third line impacting movement of the yoke with respect to the dual pivot joint in a third direction within the Y-Z plane, the fourth line impacting movement of the yoke with respect to the dual pivot joint in a fourth direction, generally opposite the third direction, within the Y-Z plane.

8. The surgical device of claim 7, further comprising an occlusion clip operatively coupled to the occlusion clip deployment device using the deployment line.

9. The surgical device of claim 8, wherein:
the occlusion clip includes a first jaw opposing a second jaw;
a first retainer loop at least partially circumscribes the first jaw, at least a portion of the occlusion clip deployment device, and at least a portion of the deployment line;
a second retainer loop at least partially circumscribes the second jaw, at least a portion of the occlusion clip deployment device, and at least a portion of the deployment line.

10. The surgical device of claim 7, wherein the end effector includes a robotic grasping feature to facilitate grasping and repositioning of the end effector by a robotic grasper.

11. The surgical device of claim 7, wherein:
the first line and the second line are coupled to a first actuator mounted to the housing;
the first actuator is repositionable and operative to reposition the first line and the second line in order to create movement between the clevis and dual pivot joint;
the third line and the fourth line are coupled to a second actuator mounted to the housing;
the second actuator is repositionable and operative to reposition the third line and the fourth line in order to create movement between the yoke and dual pivot joint.

12. The surgical device of claim 11, wherein:
the first actuator comprises a first reel upon which at least a portion of the first line and the second line are wound;
the second actuator comprises a second reel upon which at least a portion of the third line and the fourth line are wound;
repositioning of the first reel is operative to distally reposition one of the first line and the second line, while repositioning of the first reel is operative to proximally reposition the other of the first line and the second line;

repositioning of the second reel is operative to distally reposition one of the third line and the fourth line, while repositioning of the second reel is operative to proximally reposition the other of the third line and the fourth line.

13. The surgical device of claim 12, wherein the first control includes a brake that may be selectively applied to the first actuator and the second actuator to retard movement of the dual pivot joint with respect to the clevis within the X-Y plane and movement of the yoke with respect to the dual pivot joint within the Y-Z plane.

14. The surgical device of claim 13, wherein:
the brake comprises a spring biased button operatively coupled to a series of teeth;
the first reel includes a series of teeth;
the second reel includes a series of teeth; and
engagement between at least one of the series of teeth operatively coupled to the spring biased button and at least one of the series of teeth of the first reel and least one of the series of teeth of the second reel is operative to retard movement of the dual pivot joint with respect to the clevis within the X-Y plane and movement of the yoke with respect to the dual pivot joint within the Y-Z plane.

15. The surgical device of claim 7, further comprising an occlusion clip deployment device operatively coupled to the end effector and to a second control, wherein:
the housing is operatively coupled to the second control; and,
the second control includes a clip repositioning line extending along the conduit, the clip repositioning line impacting movement of the occlusion clip deployment device between a first position and a second position.

16. The surgical device of claim 15, wherein:
the second control includes a lever operatively coupled and selectively repositionable with respect to the housing, the lever being operatively coupled to the clip repositioning line so that movement of the lever is operative to reposition the occlusion clip deployment device;
the lever is repositionable between a locked and an unlocked position;
the unlocked position allows the lever to be repositioned; and,
the locked position retards the lever from being repositioned.

17. A surgical device comprising:
a housing operatively coupled to a first control;
an end effector operatively coupled to the first control, the end effector comprising a clevis selectively repositionable with respect to a dual pivot joint within an X-Y plane, the dual pivot joint selectively repositionable with respect to a yoke within an Y-Z plane;
a surgical conduit extending between the housing and the end effector;
an occlusion clip deployment device operatively coupled to the end effector and configured to deploy an occlusion clip comprising opposing parallel beams biased toward one another;
a deployment control operatively coupled to the housing, the deployment control including a deployment line extending along the conduit and concurrently mounted to a deployment plug removably fastened to the housing; and,
an occlusion clip operatively coupled to the occlusion clip deployment device using the deployment line, wherein:
the occlusion clip includes a first jaw opposing a second jaw;
a first retainer loop at least partially circumscribes the first jaw, at least a portion of the occlusion clip deployment device, and at least a portion of the deployment line;
a second retainer loop at least partially circumscribes the second jaw, at least a portion of the occlusion clip deployment device, and at least a portion of the deployment line.

18. The surgical device of claim 17, wherein the end effector includes a robotic grasping feature to facilitate grasping and repositioning of the end effector by a robotic grasper.

* * * * *